United States Patent
Schrock et al.

(10) Patent No.: US 8,362,311 B2
(45) Date of Patent: Jan. 29, 2013

(54) HIGHLY Z-SELECTIVE OLEFINS METATHESIS

(75) Inventors: Richard R. Schrock, Winchester, MA (US); Annie J. King, Cambridge, MA (US); Yu Zhao, Brighton, MA (US); Margaret M. Flook, Cambridge, MA (US); Amir H. Hoveyda, Lincoln, MA (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 631 days.

(21) Appl. No.: 12/571,036

(22) Filed: Sep. 30, 2009

(65) Prior Publication Data

US 2011/0077421 A1 Mar. 31, 2011

(51) Int. Cl.
C07C 6/00 (2006.01)
C07F 11/00 (2006.01)
(52) U.S. Cl. ............ 585/646; 556/63; 556/413
(58) Field of Classification Search .......... 556/63, 556/413; 585/646
See application file for complete search history.

(56) References Cited

U.S. PATENT DOCUMENTS

| | | |
|---|---|---|
| 5,055,628 A | 10/1991 | Lin et al. |
| 5,889,128 A | 3/1999 | Schrock et al. |
| 6,121,473 A | 9/2000 | Schrock et al. |
| 6,271,325 B1 | 8/2001 | McConville et al. |
| 6,316,555 B1 | 11/2001 | Schrock et al. |
| 6,346,652 B1 | 2/2002 | Schrock et al. |
| 6,610,806 B2 | 8/2003 | Schrock et al. |
| 6,855,839 B2 | 2/2005 | McConville et al. |
| 7,135,544 B2 | 11/2006 | Schrock et al. |
| 2008/0119678 A1 | 5/2008 | Hock et al. |

FOREIGN PATENT DOCUMENTS

| | | | |
|---|---|---|---|
| WO | WO 96/04289 | * | 2/1996 |
| WO | WO 2008/040332 A1 | * | 4/2008 |
| WO | WO 2008/155506 A1 | * | 12/2008 |

OTHER PUBLICATIONS

Vlnokurov et al., Organometallics, vol. 27, No. 8, pp. 1878-1886 (2008).*
Begantsova et al., Russian Chemical Bulletin, vol. 56, No. 2, pp. 255-260 (2007).*
[No Author Listed] New catalysts promise faster, cleaner, and more efficient research platform. Science Daily. Nov. 16, 2008. 2 pages.
Aeilts et al., A readily available and user-friendly chrial catalyst for efficient enantioselective olefin metathesis. Angew Chem Int Ed. 2001;40(8):1452-6.
Agbossou et al., Synthesis and Reactivity of Chiral Rhenium Alcohol Complexes of the Formula $[(\eta^5-C_5H_5)Re(NO)(PPh_3)(ROH)]\oplus BF_4\ominus$. Chem Berichte. 1990;123(6):1293-9.

(Continued)

*Primary Examiner* — Porfirio Nazario Gonzalez
(74) *Attorney, Agent, or Firm* — Choate, Hall & Stewart LLP; Andrea L. C. Robidoux; Xiaodong Li

(57) ABSTRACT

The present invention relates generally to catalysts and processes for the Z-selective formation of internal olefin(s) from terminal olefin(s) via homo-metathesis reactions.

37 Claims, 3 Drawing Sheets

Trip = $2,4,6-i-Pr_3C_6H_2$

OTHER PUBLICATIONS

Al Obaidi et al., Steric and electronic effects on the chemistry of molybdenum octahedrally co-ordinated by six nitrogen atoms. The molecular structure of [Mo{HB(3,5-Me$_2$C$_3$N$_2$H)$_3$}(NO)(Pyrollide)$_2$]. J Chem Soc Chem Commun. 1984;(11): 690-2.

Anderson et al., Kinetic selectivity of olefin metathesis catalysts bearing cyclic (alkyl)(amino)carbenes. Organometallics. 2008;27(4):563-6.

Ascenso et al., Synthesis and characterization of [W(NC$_4$Me$_4$)$_2$Cl$_2$] and [W(NC$_4$Me$_4$)$_2$(CH$_3$)$_2$], the first azametallocene tungsten complexes with pyrrolyl ligands. Electronic structure and bonding of tungsten bispyrrolyl complexes. Inorg Chem Acta. 2003; 356: 249-58.

Bailey et al., Evaluation of molybdenum and tungsten metathesis catalysts for homogeneous tandem alkane metathesisorganometallics. 2009;28(1):355-60.

Bazan et al., Living ring-opening metathesis polymerization of 2,3-difunctionalized 7-oxanorbornenes and 7-oxanorbornadienes by Mo(CHCMe2R)(NC6H3-iso-Pr2-2,6)(O-tert-Bu)2 and Mo(CHCMe2R)(NC6H3-iso-Pr2-2,6)(OCMe2CF3)2. J Am Chem Sco. 1991;113(18):6899-907.

Bei et al., Highly efficient olefin-metathesis catalysts. Pharm Technol. 2008:s18.

Blackwell et al., Enediynes via sequential acetylide reductive coupling and alkyne metathesis: Easy access to well-defined molybdenum initiators for alkyne metathesis. Organometallics. 2003;22: 3351-53.

Blackwell et al., New approaches to olefin cross-metathesis. J Am Chem Soc. 2000;122:58-71.

Blanc et al., Dramatic improvements of well-defined silica supported mo-based olefin metathesis catalysts by tuning the n-containing ligands. J Am Chem Soc. 2007;129(27):8434-5.

Blanc et al., Highly active, stable, and selective well-defined silica supported mo imido olefin metathesis catalysts. J Am Chem Soc. 2007; 129(17):1044-1045.

Blanc et al., Surface versus molecular siloxy ligands in well-defined olefin metathesis catalysis: [{(RO)$_3$SiO}Mo(=NAr)(=CH$t$Bu)(CH$_2$$t$Bu)]. Angew Chem Int Ed. 2006;45:1216-20.

Bornand et al., Mechanism-based design of a ROMP catalyst for sequence-selective copolymerization. Angew Chem Int Ed Engl. Dec. 9, 2005;44(48):7909-11.

Brunner et al., Catalytic hydrosilylation or hydrogenation at one coordination site of [Cp'Fe(CO)(X)] fragments. Angewandte Chemie Intl Ed Engl. Oct. 1990;29(10):1131-2.

Brunner et al., Optisch aktive Übergangsmetall-Komplexe, LI: P-Liganden als optisch aktive Hilfsstoffe in den Komplexen C5H5M(CO)(NO)L, M=Cr, Mo, W. Chem Ber. 1978;111:673-91.

Brunner, Optical activity at an asymmetrical manganese atom. Angew Chem, Int Ed Engl. 1969;8:382-3.

Brunner, Optically active organometallic compounds of transition elements with chiral metal atoms. Angew Chemie Intl Ed. May 3, 1999;38(9):1194-1208.

Brunner, Stability of the metal configuration in chiral-at-metal half-sandwich compounds. Eur J Inorg Chem. 2001:905-12.

Burdett et al., Renewable monomer feedstocks via olefin metathesis: fundamental mechanistic studies of methyl oleate ethenolysis with the first-generation grubbs catalyst. Organometallics. 2004;23(9):2027-47.

Cantrell et al., Ring-opening Metathesis of a cyclic imine. Organometallics. Aug. 2, 2000;19(18):3562-68.

Chatterjee et al., Olefin Cross-Metathesis. Handbook Metathesis. 2003;2:246-95.

Connon et al., Recent developments in olefin cross-metathesis. Angew Chem Int Ed Engl. Apr. 29, 2003;42(17):1900-23.

Corma et al., Chemical routes for the transformation of biomass into chemicals. Chem Rev. Jun. 2007;107(6):2411-502. Epub May 30, 2007.

Dias et al., Synthesis, characterisation, crystal structure, reactivity and bonding in titanium complexes containing 2,3,4,5-tetramethylpyrrolyl. J Chem Soc, Dalton Trans. 1997;1055-61.

Dinger et al., High turnover numbers with ruthenium-based metathesis catalysts. Adv Synth Catal. Aug. 2002;344(6-7):671-7.

Dolman et al., Efficient catalytic enantioselective synthesis of unsaturated amines: preparation of small- and medium-ring cyclic amines through mo-catalyzed asymmetric ring-closing metathesis in the absence of solvent. J Am Chem Soc. Jun. 19, 2002;124(24):6991-7.

Dolman, New chiral molybdenum metathesis catalysts; application of the enantioselective preparation of cyclic amines. Ph.D. Thesis. MIT. Jun. 2004. 234 pages.

Duarte et al., Chlorobis(dimethylamido)($\eta^5$-2,5-dimethylpyrrolyl)titanium(IV), [Ti(NMe$_2$)$_2$(DMP)C1]. Acta Cryst. 2005;C61:m104-6.

Feldman et al., Recent advances in the chemistry of "d$^0$" alkylidine metallacyclobutane complexes. Prog Inorg Chem. 1991;39:1-74.

Flook et al., Z-selective olefin metathesis processes catalyzed by a molybdenum hexaisopropylterphenoxide monopyrrolide complex. J Am Chem Soc. Jun. 17, 2009;131(23):7962-3.

Fontecave et al., Chiral-at-metal complexes as asymmetric catalysts. In Chiral Diazaligands for Asymmetric Synthesis. Top Organometallic Chem. 2005;15(2005):271-88.

Forman et al., A stable ruthenium catalyst for productive olefin metathesis. Organometallics. 2004;23(21):4824-7.

Fürstner et al., Alkyne metathesis: Development of a novel molybdenum-based catalyst system and its application to the total synthesis of epothilone A and C. Chem Eur J. 2001;7(24):5299-5317.

Fürstner et al., Mo[N($t$-Bu)(Ar)]$_3$complexes as catalyst precursors: in situ activation and application to metathesis reactions of alkynes and diynes. J Am Chem Soc. 1999;121(40):9453-54.

Furstner et al., Cationic ruthenium allenylidene complexes as catalysts for ring closing olefin metathesis. Chemistry. May 15, 2000;6(10):1847-57.

Ganter, Chiral organometallic half-sandwich complexes with defined metal configuration. Chem Soc Rev. May 2003;32(3):130-8.

Giessert et al., Intermolecular enol ether-alkyne metathesis. Org Lett. May 15, 2003;5(10):1793-6.

Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Angew Chem Int Ed Engl. 2007;46(21):3860-4.

Giudici et al., Directed catalytic asymmetric olefin metathesis. Selectivity control by enoate and ynoate groups in Ru-catalyzed asymmetric ring-opening/cross-metathesis. J Am Chem Soc. Apr. 4, 2007;129(13):3824-5. Epub Mar. 8, 2007.

Hadlington et al., Catalyst flexes for extra control. Chemistry World. Nov. 17, 2008. Last accessed online. Dec. 1, 2008.

Hesek et al., The first asymmetric synthesis of chiral ruthenium tris(bipyridine) from racemic ruthenium bis(bipyridine) complexes. Tetrahedron Lett. Apr. 8, 2000;41(15):2617-20.

Hock et al., Dipyrrolyl precursors to bisalkoxide molybdenum olefin metathesis catalysts. J Am Chem Soc. 2006:128(50):16373-5.

Ibrahem et al., Highly Z- and enantioselective ring-opening/cross-metathesis reactions catalyzed by stereogenic-at-Mo adamantylimido complexes. J Am Chem Soc. Mar. 25, 2009;131(11):3844-5.

Jiang et al., Fundamental studies of tungsten alkylidene imido monoalkoxidepyrrolide complexes. J Am Chem Soc. Jun. 10, 2009;131(22):7770-80.

Jiang et al., Highly Z-selective metathesis homocoupling of terminal olefins. J Am Chem Soc. Nov. 25, 2009;131(46):16630-1.

Kershner et al., $\eta^5$-Heterocyclic metal carbonyls. Coord Chem Rev. 1987;79(1987):279-92.

Kiely et al., Enantioselective synthesis of medium-ring heterocycles, tertiary ethers, and tertiary alcohols by Mo-catalyzed ring-closing metathesis. J Am Chem Soc. Mar. 27, 2002;124(12):2868-9.

Knof et al., Predetermined chirality at metal centers. Angew Chemie Intl Ed. Feb. 1, 1999;38(3):302-22.

Kreickmann et al., Imido alkylidene bispyrrolyl complexes of tungsten. Organometallics 2007;26: 5702-11.

Lacour et al., Recent developments in chiral anion mediated asymmetric chemistry. Chem Soc Rev. Nov. 2003;32(6):373-82.

Lee et al., Enantioselective synthesis of cyclic enol ethers and all-carbon quaternary stereogenic centers through catalytic asymmetric ring-closing metathesis. J Am Chem Soc. Apr. 19, 2006;128(15):5153-7.

Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc. Aug. 5, 2009;131(30):10652-61.

Liu et al., Regioselective ring-opening/cross-metathesis reactions of norbornene derivatives with electron-rich olefins. Org Lett. Jan. 6, 2005;7(1):131-3.

Lokare et al., Synthesis, properties, and structure of tethered molybdenum alkylidenes. Organometallics. 2008;27(19):5130-8.

Malcolmson et al., Highly efficient molybdenum-based catalysts for enantioselective alkene metathesis. Nature. Dec. 18, 2008;456(7224):933-7. Epub Nov. 16, 2008.

Marinescu et al., Ethenolysis reactions catalyzed by imido alkylidene monoaryloxide monopyrrolide (MAP) complexes of molybdenum. J Am Chem Soc. Aug. 12, 2009;131(31):10840-1.

Marinescu et al., Inversion of configuration at the metal in diastereomeric imido alkylidene monoaryloxide monopyrrolide complexes of molybdenum. J Am Chem Soc. Jan. 14, 2009;131(1):58-9.

Maruoka et al., Efficient synthesis of sterically hindered chiral binaphthol derivatives. Bull Chem Soc Jpn. 1988;61(8):2975-6.

McDougal et al., Asymmetric Morita-Baylis-Hillman reactions catalyzed by chiral Brønsted acids. J Am Chem Soc. Oct. 8, 2003;125(40):12094-5.

McDougal et al., The development of the asymmetric morita—baylis—hillman reaction catalyzed by chiral brønsted acids. Adv Synth Cat. 2004;346:1231-40.

Meek et al., The significance of degenerate processes to enantioselective olefin metathesis reactions promoted by stereogenic-at-Mo complexes. J Am Chem Soc. Nov. 18, 2009;131(45):16407-9.

Monchaud et al., Ion-pair-mediated asymmetric synthesis of a configurationally stable mononuclear tris(diimine)-iron(II) complex. Angew Chem Int Ed Engl. Jul. 2, 2002;41(13):2317-9.

Nicolaou et al., Metathesis reactions in total synthesis. Angew Chem Int Ed Engl. Jul. 18, 2005;44(29):4490-527.

Pezet et al., Highly diastereoselective preparation of ruthenium bis(diimine) sulfoxide complexes: new concept in the preparation of optically active octahedral ruthenium complexes. Organometallics. 2000;19(20):4008-15.

Poater et al., Understanding d(0)-olefin metathesis catalysts: which metal, which ligands? J Am Chem Soc. Jul. 4, 2007;129(26):8207-16. Epub Jun. 9, 2007.

Rhers et al., A well-defined, silica-supported tungsten imido alkylidene olefin metathesis catalyst. Organometallics. 2006;25(15):3554-7.

Sattely et al., Design and stereoselective preparation of a new class of chiral olefin metathesis catalysts and application to enantioselective synthesis of quebrachamine: catalyst development inspired by natural product synthesis. J Am Chem Soc. Jan. 28, 2009;131(3):943-53.

Sattely et al., Enantioselective synthesis of cyclic amides and amines through mo-catalyzed asymmetric ring-closing metathesis. J Am Chem Soc. Jun. 15, 2005;127(23):8526-33.

Sattely, Cyclic amines and amides through molybdenum-catalyzed asymmetric olefin metathesis: A total synthesis of quebrachamine. Jan. 1, 2007. Boston College Dissertations and Theses. Paper AAI3256831. http://escholarship.bc.edu/dissertations/AAI3256831. 340 pages.

Schrock et al., Further studies of imido alkylidene complexes of tungsten, well-characterized olefin metathesis catalysts with controllable activity. Organometallics. Aug. 1990;9(8):2262-75.

Schrock et al., Molybdenum alkylidyne complexes that contain 3,3'-di-t-butyl-5,5', 6,6'—tetramethyl-1, 1'—biphenyl-2,2'—diolate ([Biphen]$^{2-}$) ligand. J Organomet Chem. 2003;684:56-67.

Schrock et al., Molybdenum and tungsten imido alkylidene complexes as efficient olefin-metathesis catalysts. Angew Chem Int Ed Engl. 2003;42(38):4592-33.

Schrock et al., Preparation of molybdenum and tungsten neopentylidyne complexes of the type $M(CCMe_3)(O_2CR)_3$, their reactions with acetylenes, and the X-ray structure of the $\eta^3$—cyclopropenyl complex $W[C_3(CMe_3)Et_2]O_2CCH_3)_3^1$. Organometallics. 1986;5:25-33.

Schrock et al., Synthesis of molybdenum imido alkylidene complexes and some reactions involving acyclic olefins. J Am Chem Soc. 1990;112:3875-86.

Schrock et al., Thousands of catalysts for olefin metathesis: variability, longevity and asymmetry at the metal. Abstract. Presented Oct. 24, 2008 at Technical University of Berlin.

Schrock, High oxidation state multiple metal-carbon bonds. Chem Rev. 2002;102:145-79.

Schrock, Recent advances in high oxidation state mo and w imido alkylidene chemistry. Chem Rev. 2009;109(8):3211-26.

Schrodi et al., Ruthenium olefin metathesis catalysts for the ethenolysis of renewable feedstocks. Clean: Soil, Air, Water. 2008;36:669-673.

Singh et al., Molybdenum imido alkylidene metathesis catalysts that contain electron-withdrawing biphenolates or binaphtholates. Organometallics. 2007:26(10):2528-39.

Singh et al., Synthesis of monoalkoxide monopyrrolyl complexes Mo(NR)(CHR')(OR")(pyrrolyl): enyne metathesis with high oxidation state catalysts. J Am Chem Soc. Oct. 24, 2007;129(42):12654-5. Epub Sep. 29, 2007.

Sinha et al., Diphenylamido precursors to bisalkoxide molybdenum olefin catalysts. Organometallics. 2006;25(19):4621-6.

Sinha et al., Reactions of $M(N-2,6-i-Pr_2C_6H_3)(CHR)(CH_2R')_2$ (M=Mo, W) complexes with alcohols to give olefin metathesis catalysts of the type $M(N-2,6-i-Pr_2C_6H_3)(CHR)(CH_2R')(OR")$. Organometallics. 2006;25:1412-23.

Solans-Monfort et al., $d^0$ Re-based olefin metathesis catalysts, $Re(\equiv CR)(\equiv CHR)(X)(Y)$: The key role of X and Y ligands for efficient active sites. J Am Chem Soc. 2005;127(40):14015-25.

Takano et al., Enantioselective route to both (+)- and (−)-enantiomers of quebrachamine using a single chiral synthon. J Chem Soc Chem Commun. 1981:1153-5.

Takemura et al., Stereochemical aspects of asymmetric Diels-Alder reaction catalyzed by chiral alkoxyaluminum dichlorides. Tetrahedron Lett. 1987;28(46):5687-90.

Tallarico et al., Selectivity in ring-opening metatheses. Tetrahedron. Dec. 1, 1997;53(48):16511-20.

Tayama et al., Activation of ether functionality of allyl vinyl ethers by chiral bis(organoaluminum) Lewis acids: application to asymmetric Claisen rearrangement. Tetrahedron. Oct. 7, 2002;58(41):8307-12.

Tonzetich et al., Reaction of phosphoranes with $Mo(N-2,6-i-Pr_2C_6H_3)(CHCMe_3)[OCMe(CF_3)_2]_2$: Synthesis and reactivity of an anionic imido alkylidyne complex. Organometallics. 2006;25:4301-6.

Tsai et al, Facile synthesis of trialkoxymolybdenum(VI) alkylidyne complexes for alkyne metathesis. Organometallics. 2000;19:5260-62.

Van Veldhuizen et al., A readily available chiral Ag-based N-heterocyclic carbene complex for use in efficient and highly enantioselective Ru-catalyzed olefm metathesis and Cu-catalyzed allylic alkylation reactions. J Am Chem Soc. May 11, 2005;127(18):6877-82.

Van Veldhuizen et al., A recyclable chiral Ru catalyst for enantioselective olefin metathesis. Efficient catalytic asymmetric ring-opening/cross metathesis in air. J Am Chem Soc. May 8, 2002;124(18):4954-5. Erratum in: J Am Chem Soc. Oct. 15, 2003;125(41):12666.

Walls et al., Alkaloids from stemmadenia species-I : The alkaloids of S. Donnell-Smithii and S. Galeottiana. Tetrahedron. May 1958;2(3-4):173-82.

Weatherhead et al., Mo-catalyzed asymmetric olefin metathesis in target-oriented synthesis: enantioselective synthesis of (+)-africanol. Proc Natl Acad Sci U S A. Apr. 20, 2004;101(16):5805-9. Epub Mar. 31, 2004.

Werner et al., Bur Kennfnie dee asymmetrimhen Kobaltatoms. I. Ber Dtsch Chem Ges. 1911;44:1887-98. German.

Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans. 1994;10:1511-6.

Yashiro et al., Efficient stereochemical regulation of octahedral cobalt(III) complexes by a chiral bidentate ligand. Part 1. Effect of N-alkyl substitutions. J Chem Soc, Dalton Trans. 1994;7:1073-7.

Yi et al., The ruthenium acetylide catalyzed cross-coupling reaction of terminal and internal alkynes: isolation of a catalytically active β-agostic intermediate species. Organometallics. 1998;17(15):3158-60.

Zhang et al., A reductive recycle strategy for the facile synthesis of molybdenum(VI) alkylidyne catalysts for alkyne metathesis. Chem Commun. 2003:832-3.

Zhou et al., Synthesis and reactivity of chiral rhenium indenyl complexes of the formula $[(\eta^{3-5}\text{-}C_9H_7)\text{Re(NO)(PPh3)(X)}]n+$. Organometallics. 1993;12(10):3918-23.

Zhu et al., Chiral Mo—Binol complexes: activity, synthesis, and structure. efficient enantioselective six-membered ring synthesis through catalytic metathesis. J Am Chem Soc. 1999;121:8251-9.

International Preliminary Report on Patentability from International Patent Application Serial No. PCT/US2007/024318, filed Nov. 21, 2007, mailed May 26, 2009.

International Search Report and Written Opinion in PCT/US2007/024318, issued on May 7, 2008.

International Preliminary Report on Patentability in connection with Application Serial No. PCT/US2009/000465 issued Jul. 27, 2010.

International Search Report and Written Opinion in connection with Application Serial No. PCT/US2009/000465 mailed Jul. 13, 2009.

Invitation to Pay Additional Fees in connection with Application Serial No. PCT/US2009/000465 mailed May 11, 2009.

Herrmann et al., "Methyltrioxorhenium als Katalysator für die Olefin-Metathese," *Angew Chem* 103:1704-1706 (1991).

Herrmann et al., "Methyltrioxorhenium as Catalyst for Olefin Metathesis," *Angew Chem Int. Ed. Engl.* 103:1636-1638 (1991).

Ibrahem et al., "Highly Z- and Enantioselective Ring-Opening/Cross-Metathesis Reactions Catalyzed by Stereogenic-at-Mo Adamantylimido Complexes," *J. Am. Chem. Soc.* 131: 3844-3845 (2009). Published on Web Feb. 27, 2009.

Jiang et al., "Highly Z-Selective Metathesis Homocoupling of Terminal Olefins," *J. Am. Chem. Soc.* 131 : 16630-16631 (2009). Published on Web Oct. 30, 2009.

International Search Report for PCT/US2010/002644, mailed Mar. 7, 2011.

International Preliminary Report on Patentability for PCT/US2010/002644, issued Apr. 3, 2012.

Written Opinion for PCT/US2010/002644, mailed Mar. 7, 2011.

* cited by examiner

R = butyl (S$_1$), hexyl (S$_2$), CH$_2$Ph (S$_3$), CH$_2$SiMe$_3$ (S$_4$), (CH$_2$)$_8$CO$_2$Me (S$_5$), (CH$_2$)$_7$CO$_2$Me (S$_6$), CH$_2$-Bpin (S$_7$), CH$_2$OBenzyl (S$_8$), CH$_2$NHTosyl (S$_9$)

CH$_2$NHPh (S$_{10}$), CH$_2$(OTBs) (S$_{11}$), CH$_2$Cy (S$_{12}$)

HIGHLY Z-SELECTIVE OLEFINS METATHESIS

STATEMENT REGARDING FEDERALLY SPONSORED RESEARCH OR DEVELOPMENT

This invention was made with the support under the following government contracts: CHE-0554734 awarded by the National Science Foundation and 5-R01-GM59426 awarded by the National Institutes of Health. The government has certain rights in the invention.

FIELD OF THE INVENTION

The invention related generally to the Z-selective formation of internal olefins, produced via metathesis coupling of terminal olefins.

BACKGROUND OF THE INVENTION

Carbon-carbon coupling reactions catalyzed by transition metal catalysts are among the most important reactions of synthetic organic chemistry. Metathesis of a terminal olefin with itself produces ethylene and an internal olefin (Equation 1):

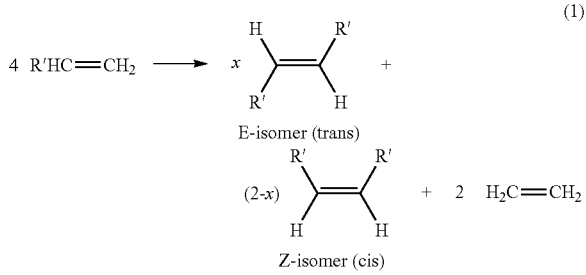

wherein x is a value between 0 and 2. This is called a homo-metathesis or homo-coupling reaction. Metathesis catalysts for coupling reactions have been described for decades. However, a mixture of the two possible products (E-isomer and Z-isomer) is usually produced, with the E-isomer being the dominant isomer. The Z-isomer, in many cases, is the isomer which is required by organic chemists for the synthesis of pharmaceuticals, or other chemical products. The Z-isomer also is that largely found in natural products that contain an internal 1,2-disubstituted olefin. Mixtures of Z- and E-isomers are usually difficult to separate and are therefore, generally undesirable. Z-selective coupling of internal olefins is much less useful than Z-selective coupling of terminal olefins, since Z internal olefins themselves must be prepared through Z-selective coupling of terminal olefins. Alternative methods of preparing internal olefins (e.g., Wittig chemistry), are generally not catalytic and/or not Z-selective.

Accordingly, improved methods and catalysts are needed.

SUMMARY OF THE INVENTION

The present invention, in some embodiments, provides methods comprising reacting a first molecule comprising a terminal double bond and a second, identical molecule via a homo-metathesis reaction to produce a product comprising an internal double bond, wherein the internal double bond of the product comprises one carbon atom from the terminal double bond of the first molecule and one carbon atom from the terminal double bond of the second carbon atom, and wherein at least about 60% of the internal double bond of the product is formed as the Z-isomer.

In some cases, a method comprises providing a catalyst having the structure:

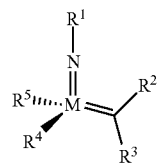

wherein M is Mo or W, $R^1$ is aryl, heteroaryl, alkyl, heteroalkyl, optionally substituted, $R^2$ and $R^3$ can be the same or different and are hydrogen, alkyl, alkenyl, heteroalkyl, heteroalkenyl, aryl, or heteroaryl, optionally substituted, and $R^4$ and $R^5$ can be the same or different and are alkyl, heteroalkyl, aryl, heteroaryl, silylalkyl, or silyloxy, optionally substituted, wherein at least one of $R^4$ or $R^5$ is a ligand containing oxygen bound to M, and reacting a first molecule comprising a terminal double bond and a second, identical molecule in the presence of the catalyst to produce a product comprising an internal double bond, wherein the internal double bond of the product comprises one carbon atom from the terminal double bond of the first molecule and one carbon atom from the terminal double bond of the second carbon atom, and wherein at least about 30% of the internal double bond of the product is formed as the Z-isomer.

Figure 1:
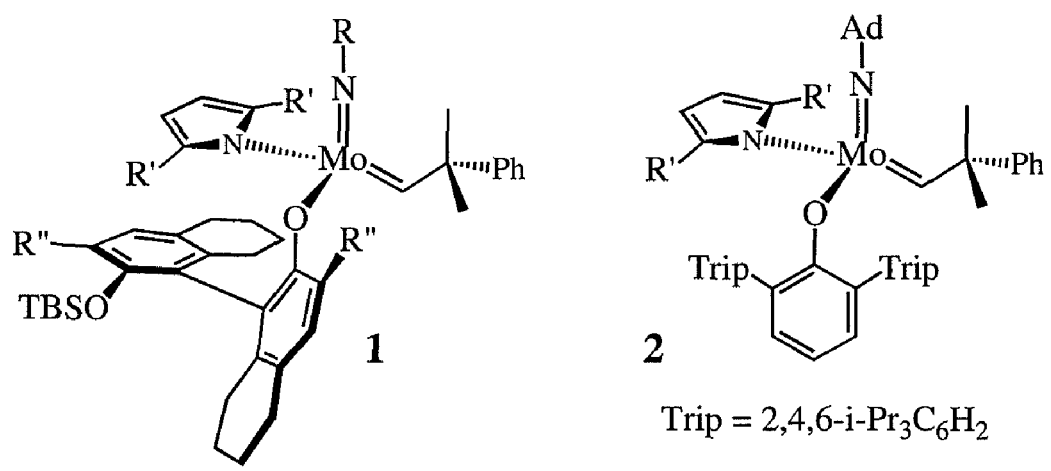
FIG. 1 shows non-limiting examples of catalysts for metathesis, according to some embodiments of the present invention.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention relates generally to catalysts and processes for the highly selective formation of the Z-isomer of an internal olefin from identical terminal olefins via a homo-metathesis reaction. Z-isomers of internal olefins are important chemicals used as feedstock to produce higher valued end products. Mixtures of Z- and E-isomers are generally undesirable as the separation of the isomers can be a difficult and costly process. Thus, catalysts for metathesis reactions which produce a high percentage of the product as a Z-isomer are desirable.

The homo-metathesis reactions described herein may proceed with high selectivity and/or high conversion. The term, "homo-metathesis," as used herein, refers to a metathesis reaction between a first molecule comprising a double bond and a second, identical molecule. The product formed comprises an internal double bond, wherein the double bond comprises one carbon atom from the double bond of the first molecule and one carbon atom from the double bond of the second molecule. As shown in Equation 1, and as will be known to those of ordinary skill in the art, the internal double bond of the product may either have a Z-configuration (i.e., cis) or E-configuration (i.e., trans). In some embodiments, the methods may provide the ability to selectively synthesize, via a homo-metathesis reaction, products having a high percentage of Z-configuration about the double bond. Those of ordinary skill in the art would understand the meaning of the terms "cis" or "Z" and "trans" or "E," as used within the context of the invention.

In some embodiments, a method comprises reacting a first molecule comprising a terminal double bond and a second, identical molecule via a homo-metathesis reaction to produce a product comprising an internal double bond. In some cases, the terminal bond of the first and the second molecules are mono-substituted. Thus, the internal double bond of the product may comprise one monosubstituted olefinic carbon atom from the terminal double bond of the first molecule and one monosubstituted olefinic carbon atom from the terminal double bond of the second carbon atom. The internal double bond of the product may be produced in a high Z:E ratio in favor of the Z-isomer, as described herein. A "terminal double bond," as used herein, in the context of a metathesis reaction, refers to a double bond between a first and a second carbon atom (e.g., C=C), wherein the two substituents on the first carbon atom are both hydrogen and at least one substituents on the second carbon atom is not hydrogen (e.g., $H_2C=CR^aH$,). An "internal double bond," as used herein, in the context of a metathesis reaction, refers to a double bond between a first and a second carbon atom (e.g., C=C), wherein at least one substituent on each of the first and second carbon atoms are not hydrogen (e.g., $R^aR^bC=CR^cR^d$, wherein at least one of $R^a$ and $R^b$ are not hydrogen and at least one of $R^c$ and $R^d$ are not hydrogen).

In some cases, the first and second molecules may have the formula:

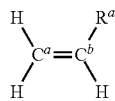

wherein $R^a$ is alkyl, alkenyl, heteroalkyl, heteroalkenyl, aryl, heteroaryl, or acyl, optionally substituted. The internal double bond of the product may comprise one $C^bHR^a$ from each of the first and second molecules (e.g., to form the Z- or E-isomer of $R^aHC^b=C^bHR^a$).

As will be understood by those of ordinary skill in the art, a side-product of a homo-metathesis reaction of two terminal olefins is ethylene. The formation (or presence) of ethylene is a significant difference in this type of reaction as compared to a cross- and/or homo-metathesis reaction involving at least one internal olefin. In some instances, the presence of ethylene may lead to a decrease in performance (e.g., yield, Z:E ratio, etc.) of a catalyst as compared to metathesis reactions which are not conducted in the presence of ethylene. Possible causes for a decrease in performance is the reformation of the starting materials (e.g., if a metathesis reaction occurs between ethylene and the product formed from the homo-metathesis) and/or isomerization of the homo-metathesis product to form the E-isomer (e.g., a Z-isomer of a homo-metathesis reaction may associate with the metal center to form a metallocyclobutane, followed by release of a compound which may be the E-isomer). Accordingly, some of the catalysts described herein exhibit little or no decrease in performance when conducted in the presence of ethylene as compared to reactions conducted in the absence of ethylene. Methods for choosing catalysts are described herein.

In some embodiments, the internal double bond of a product of a homo-metathesis reaction may be formed with high selectivity for the Z-isomer. For example, the internal double bond of the product may be formed in a Z:E (i.e., cis:trans) ratio of about 1:2, about 1:1, about 2:1, about 3:1, about 4:1, about 5:1, about 10:1, about 25:1, about 50:1, about 100:1, or greater. In some embodiments, the double bond may be produced in a Z:E ratio greater than about 1:1, greater than about 2:1, greater than about 3:1, greater than about 4:1, greater than about 5:1, greater than about 10:1, greater than about 20:1, greater than about 30:1, greater than about 40:1, greater than about 50:1, greater than about 75:1, greater than about 100:1, or greater, in favor of the Z-isomer. In some cases, the Z- or E-selectivity may be expressed as a percentage of products formed. In some cases, the product may be greater than about 50% Z-isomer, greater than about 60% Z-isomer, greater than about 70% Z-isomer, greater than about 80% Z-isomer, greater than about 90% Z-isomer, greater than about 95% Z-isomer, greater than about 98% Z-isomer, greater than about 99% Z-isomer, or, in some cases, greater than about 99.5%. In some instances, the product may be between about 50% and about 99% Z-isomer, between about 50% and about 90% Z-isomer, between about 60% and about 99% Z-isomer, between about 60% and about 95% Z-isomer, between about 70% and about 98% Z-isomer, between about 80% and about 98% Z-isomer, between about 90% and about 99% Z-isomer, or the like.

In some cases, the metathesis reaction may proceed with high conversion. Conversion refers to the percent of the limiting reagent converted to product. In some embodiments, percent conversion may be calculated according to the following equation:

$$\% \text{ Conversion} = 100 - \left\{ \frac{(\text{final moles of limiting reagent}) \times 100}{(\text{initial moles of limiting reagent})} \right\}$$

where the initial moles of the limiting reagent may be calculated from the amount of limiting reagent added to reaction vessel and the final moles of the limiting reagent may be determined using techniques known to those of ordinary skill in the art (e.g., isolation of reagent, GPC, HPLC, NMR, etc.). In some cases, the metathesis reaction may proceed with a conversion of at least about 30%, at least about 40%, at least about 50%, at least about 60%, at least about 70%, at least about 75%, at least about 80%, at least about 85%, at least about 90%, at least about 95%, at least about 97%, at least about 98%, at least about 99%, or more. In some cases, the conversion is about 70%, about 75%, about 80%, about 85%, about 90%, about 95%, about 97%, about 98%, about 99%, or the like. In some instances, the conversion is between about 60% and about 99%, between about 70% and about 95%, between about 70% and about 90%, or any other range therein.

In some embodiments, the metathesis reaction may proceed with good turnover numbers. The term "turnover number," as used herein, refers to the number of average times a catalyst is able to promote a reaction. In some embodiments, the turnover number may be calculated according the following equation:

$$\text{Turnover number} = \frac{\% \text{ yield}}{100} \times \left\{ \frac{(\text{moles of limiting reagent})}{(\text{moles of catalyst})} \right\}$$

wherein the percent yield may be calculated according to the following equation:

$$\% \text{ Yield} = 100 \times \left\{ \frac{(\text{moles of a desired product})}{(\text{moles of limiting reagent})} \right\}.$$

For example, in a homo-metathesis reaction, the moles of catalyst may be determined from the weight of catalyst (or catalyst precursor) provided, the related moles of limiting reagent (e.g., generally one half the moles of terminal olefin starting material as two moles of starting material are reacted to form one mole of product) may be determined from the amount of limiting reagent added to the reaction vessel, and the moles of a desired product (e.g., the Z-isomer and/or E-isomer of the product) may be determined using techniques known to those of ordinary skill in the art (e.g., isolation of product, GPC, HPLC, NMR, etc.). In some cases, the metathesis reaction may proceed at a turnover number of at least about 10, at least about 25, at least about 50, at least about 100, at least about 200, at least about 300, at least about 400, at least about 500, at least about 1000, at least about 3,000, at least about 5,000, or more. In some cases, the turnover number is between about 10, and about 1000, between about 50 and about 500, between about 50 and 200, or any other range therein. In some embodiments, the turnover number is about 10, about 20, about 30, about 50, about 75, about 100, about 200, about 500, about 1000, about 5000, or the like. The turnover frequency is the turnover number divided by the length of reaction time (e.g., seconds).

A metathesis reaction may be carried out using techniques known to those of ordinary skill in the art. In some cases, the reaction may involve exposing a catalyst (e.g., as described herein) to a plurality of identical molecules comprising a terminal olefin. In some instances, the reaction mixture may be agitated (e.g., stirred, shaken, etc.). The reaction products may be isolated (e.g., via distillation, column chromatography, etc.) and/or analyzed (e.g., gas liquid chromatography, high performance liquid chromatography, nuclear magnetic resonance spectroscopy, etc.) using commonly known techniques.

Molecules comprising at least one terminal olefin will be known to those of ordinary skill in the art. A molecule comprising at least one terminal olefin may comprise one or more ethylenic units and/or heteroatoms (e.g., oxygen, nitrogen, silicon, sulfur, phosphorus, etc.). The terminal olefin generally comprising a molecule having the formula:

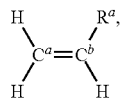

where $R^a$ is as described herein. Non-limiting examples of molecules comprising terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl) dimethyl silane, allylcyclohexane, etc.).

As noted, one set of catalysts has been identified in accordance with the invention which provides unexpected results in homo-metathesis reactions. In some embodiments, the catalyst provided is a metal complex with the structure:

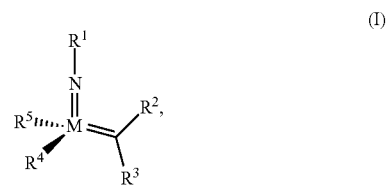

(I)

wherein M is a metal; $R^1$ is aryl, heteroaryl, alkyl, heteroalkyl, optionally substituted; $R^2$ and $R^3$ can be the same or different and are hydrogen, alkyl, alkenyl, heteroalkyl, heteroalkenyl, aryl, or heteroaryl, optionally substituted; and $R^4$ and $R^5$ can the same or different and are alkyl, heteroalkyl, aryl, heteroaryl, silyloxy, or silylalkyl, optionally substituted, or $R^4$ and $R^5$ are joined together to form a bidentate ligand with respect to M, optionally substituted. In some cases, at least one of $R^4$ or $R^5$ is a ligand containing oxygen bound to M (e.g., an oxygen-containing ligand) or a ligand containing nitrogen bound to M (e.g., a nitrogen-containing ligand). In some cases, $R^2$ is alkyl. In some instances, M is Mo or W. In a particular instance, M is W.

In a particular embodiment, one of $R^4$ and $R^5$ is a ligand containing oxygen bound to M (e.g., an oxygen-containing ligand), optionally substituted, and the other is a ligand containing nitrogen bound to M (e.g., a nitrogen-containing ligand), optionally substituted. In some cases, the oxygen-containing ligand and/or the nitrogen-containing ligand may lack a plane of symmetry. In other embodiments, both $R^4$ and $R^5$ are oxygen-containing ligands.

Figure 2:
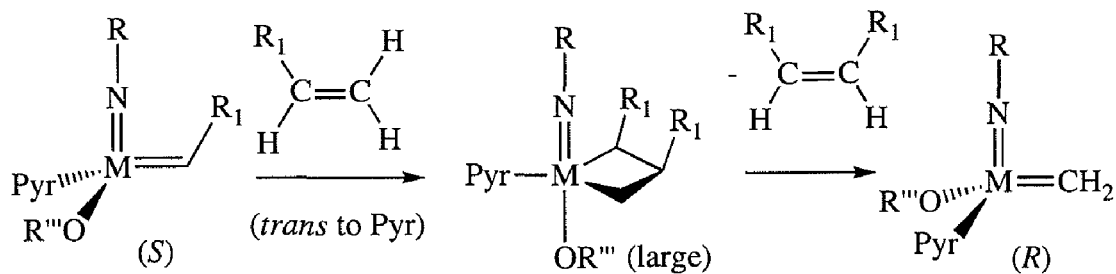
FIG. 2 illustrates a non-limiting reaction mechanism, according to some embodiments.

A possible mechanism of Z-selective homo-coupling of terminal olefins (e.g., $(R_1)HC=CH_2$) by a catalyst of formula I is shown in FIG. 2, where $R^5$ is a nitrogen-containing ligand (e.g., Pyr in FIG. 2) and $R^4$ is an oxygen-containing ligand (e.g., OR''' in FIG. 2). Generally, only syn isomers are observed by NMR or X-ray studies of catalysts of this type comprising one oxygen containing ligand and one nitrogen containing ligand. In a syn isomer of a monosubstituted alkylidene complex, the atom of the alkylidene substituent that is attached to the alkylidene carbon atom may lie in the N(imido)-M-C-(alkylidene) plane and/or may point towards the N(imido) atom. A terminal olefin may enter the coordination sphere trans to the pyrrolide (Pyr) to yield an intermediate metallacyclobutane with adjacent $R_1$ substituents. Without wishing to be bound by theory, the adjacent ($R_1$) may point away from the axial OR''' group in instances where OR''' is "large" enough to prevent formation of any metallacycle in which ($R_1$) points toward OR''', thereby leading to the formation of the Z-isomer of the product. Thus, in some embodiment, a sterically large or bulky OR''' ligand (e.g., oxygen-containing ligand) may result in an increased percentage of the Z-isomer of the product being formed as compared a substantially similar catalyst comprising a less sterically large or sterically bulky OR''' ligand. Loss of Z—($R_1$)

CH=CH(R₁) yields an intermediate methylene species with an inverted configuration at the metal center (S→R in FIG. 2). A productive metathesis reaction between the methylene species and (R₁)CH=CH₂ then yields ethylene and reforms (S)-M(NR)(CH(R₁))(Pyr)(OR'''). Those of ordinary skill in the art will be able to select (e.g., by screening tests, modeling studies, etc.) appropriate combinations of substituents in a catalyst of formula I with an R''' group of significant size such that the group aids in preventing formation of metallacycles in which (R₁) points towards R'''. In some cases, the N(imido) group may not be sufficiently large.

It will be understood by those of ordinary skill in the art that a high percentage of Z-isomer product may not necessarily be produced for every combination of substrate and catalyst due to the general nature of catalytic chemistry. Those of ordinary skill in the art will be able to apply some prediction to substrate/catalyst combinations. For example, as noted elsewhere herein, as a general trend (but not applicable in each case), where the oxygen-containing ligand is selected to be sterically large or sterically bulky, a higher percentage of Z-isomer is generally obtained. Additionally, those of ordinary skill are aware of methods and techniques to easily screen combinations of catalysts and substrates to identify those providing a high percentage of Z-isomer product. For example, a method to screen for appropriate combinations of catalyst and substrate can involve providing a first solution containing the catalyst and a second solution containing the reactant(s). The solution(s) may include solvents which are compatible with the desired analysis (e.g., deuterated solvents for NMR techniques, polar/non-polar solvents for HPLC, GLC techniques, etc.). The first solution and the second solution may be combined under the appropriate conditions (e.g., temperature, time, agitation, etc.), and, after an appropriate reaction time has elapsed, the resulting solution may be analyzed using various methods known in the art. In some cases, the solution may be filtered prior to analysis. For analysis of Z:E ratio, conversion, etc., the product may be analyzed by NMR (e.g., ¹H NMR, ¹³C NMR, etc.), HPLC, GLC, or the like. In some cases, more than one analysis may be performed. Those of ordinary skill in the art will be able to determine the appropriate method, or combination of methods, to utilize based upon the product to be analyzed. In some cases, the screening tests may be automated (e.g., with use of a robot). Additional reaction conditions and parameters are described herein.

As used herein, the term "oxygen-containing ligand" may be used to refer to ligands comprising at least one oxygen atom capable of coordinating a metal atom (e.g., $R^4$ and/or $R^5$). That is, the term refers to a ligand containing oxygen bound to M. In some cases, the term "oxygen-containing ligand" may also describe ligand precursors comprising at least one hydroxyl group, wherein deprotonation of the hydroxyl group results in a negatively charged oxygen atom, which then coordinates a metal atom. The oxygen-containing ligand may be a heteroaryl or heteroalkyl group comprising at least one oxygen atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center. The oxygen-containing ligand may be chiral or achiral, and/or monodentate or bidentate. A monodentate ligand is a ligand which binds or coordinates the metal center via one coordination site of the metal only, and/or via one site of the ligand only. A bidentate ligand is a ligand which binds or coordinates the metal center via two coordination sites of the metal and/or via two sites of the ligand (e.g., a dialkoxide ligand). Non-limiting of achiral monodentate oxygen-containing ligands include —OC(CH₃)(CF₃)₂, —OC(CH₃)₂(CF₃), —OC(CH₃)₃, —OSiR₃ (e.g., —OSiPh₃), —OAr (Ar=aryl groups such as phenyl, Mes (Mes=2,4,6-Me₃C₆H₂), 2,6-i-Pr₂C₆H₃, HIPT (hexaisopropylterphenyl), TPP (2,3,5,6-Ph₄C₆H), etc.), and the like. In some cases, the oxygen-containing ligand may be a silyloxy group.

In some cases, an oxygen-containing ligand may be chiral and may be provided as a racemic mixture or a purified stereoisomer. In some embodiments, the chiral, oxygen-containing ligand may be present in at least 80% optical purity, i.e., the oxygen-containing ligand sample contains 90% of one enantiomer and 10% of the other. In some embodiments, the chiral, oxygen-containing ligand may be at least 90% optically pure, at least 95% optically pure, or, in some cases, at least 99% optically pure.

In some cases, the oxygen-containing ligand (e.g., $R^4$ or $R^5$) lacking a plane of symmetry may comprise the following structure,

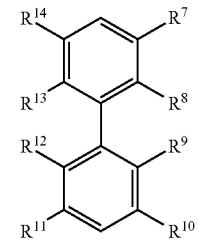

wherein $R^7$ is aryl, heteroaryl, alkyl, or heteroalkyl, optionally substituted; $R^8$ is hydrogen, —OH, halogen, alkyl, heteroalkyl, aryl, heteroaryl, acyl, acyloxy, or —OP, optionally substituted; or, together $R^7$ and $R^8$ are joined to form a ring, optionally substituted; $R^9$ is —OH, —OP, or amino, optionally substituted; $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; and P is a protecting group. The ring may be an aromatic or a non-aromatic ring. In some embodiments, the ring may be a heterocycle. In some cases, the protecting group may be a Si protecting group (e.g., tert-butyl dimethyl silyl or TBS). In some embodiments, the oxygen-containing ligand may comprise a substituted alkyl group, such as CF₃.

In some embodiments, $R^8$ and $R^9$ are attached to the biaryl parent structure via a heteroatom, such as an oxygen atom. For example, $R^8$ and $R^9$ can be —OH, alkoxy, aryloxy, acyloxy, or —OP, where P is a protecting group (e.g., Si protecting group). In some cases, $R^8$ is —OP and $R^9$ is —OH or amino.

Examples of oxygen-containing ligands lacking a plane of symmetry or nitrogen-containing ligands lacking a plane of symmetry may be a group having the structure:

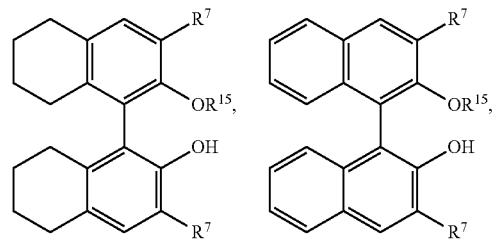

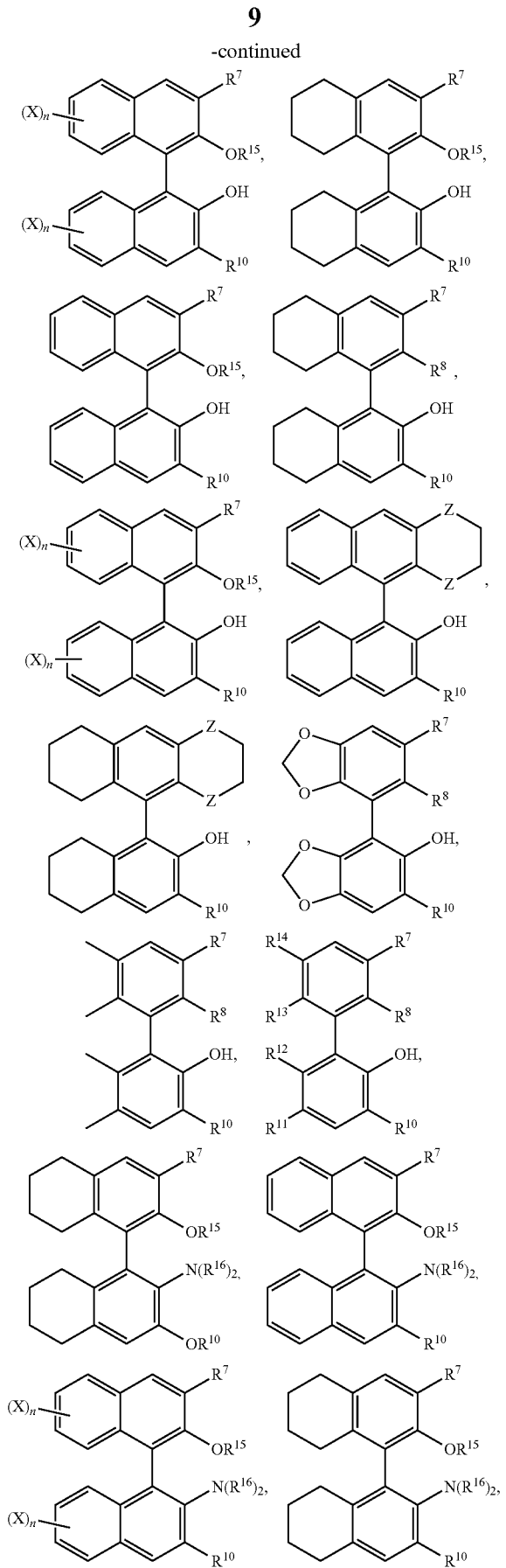
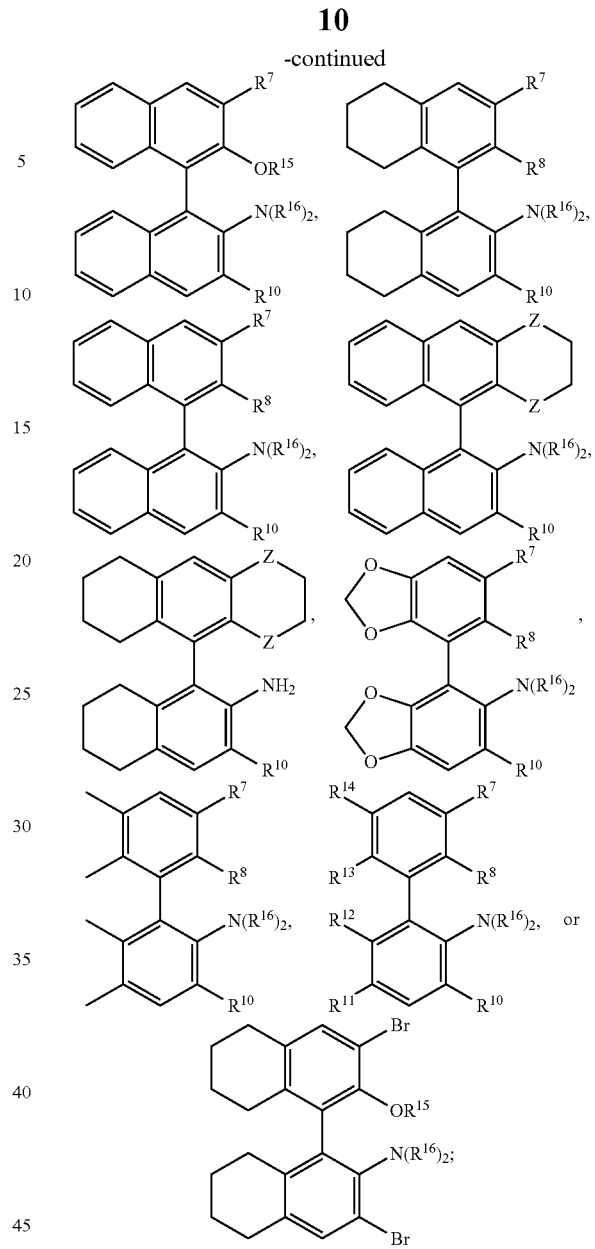

wherein each $R^7$ and $R^8$ can be the same or different and is hydrogen, halogen, alkyl, alkoxy, aryl, acyl, or a protecting group, optionally substituted, $R^{10}$ is hydrogen, halogen, alkyl, heteroalkyl, aryl, heteroaryl, or acyl, optionally substituted, each $R^{11}$, $R^{12}$, $R^{13}$, and $R^{14}$ can be the same or different and is aryl, heteroaryl, alkyl, heteroalkyl, or acyl, optionally substituted, or together $R^{11}$ and $R^{12}$ are joined to form a ring, optionally substituted, or together $R^{13}$ and $R^{14}$ are joined to form a ring, optionally substituted, $R^{15}$ is alkyl, aryl, or a protection group, optionally substituted, $R^{16}$ is hydrogen or an amine protecting group, X may or may not be present and is any non-interfering group, each Z can be the same or different and is $(CH_2)_m$, N, O, optionally substituted, n is 0-5, and m is 1-4. In some embodiments, each $R^7$ and $R^8$ can be the same or different and is hydrogen, halogen, alkyl, alkoxy, aryl, $CF_3$, Si-tri-alkyl, Si-tri-aryl, Si-alkyl-diphenyl, Si-phenyl-dialkyl, or acyl (e.g., ester), optionally substituted; $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is ary heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; $R^{15}$ is alkyl, aryl, protecting group Si-trialkyl, Si-triaryl, Si-alkyldiphenyl, Si-phenyldialkyl, or acyl, optionally substituted; $R^{16}$ is hydrogen or an amine protecting group; X can be any non-interfering group; each Z can be the same or different and is $(CH_2)_m$, N, O, optionally substituted; n is 0-5 (or any range therein); and m is 1-4 (or any range therein). In some cases, each $R^7$ and $R^{10}$ is the same or different and is halogen, methyl, t-butyl, $CF_3$, or aryl, optionally substituted.

In one set of embodiments, $R^4$ (or $R^5$) is a monodentate oxygen-containing ligand comprising or lacking a plane of symmetry, or a nitrogen-containing ligand lacking a plane of symmetry; and $R^5$ (or $R^4$) is a nitrogen containing ligand having a plane of symmetry. As used herein, a "nitrogen-containing ligand" (e.g., $R^4$ and/or $R^5$) may be any species capable of binding a metal center via a nitrogen atom. That is, the term refers to a ligand containing nitrogen bound to M. In some cases, the term "nitrogen-containing ligand" may also describe ligand precursors comprising at least one nitrogen group, wherein deprotonation of the nitrogen group results in a negatively charged nitrogen atom, which then coordinates a metal atom. In some instances, the nitrogen atom may be a ring atom of a heteroaryl or heteroalkyl group. In some cases, the nitrogen atom may be a substituted amine group. It should be understood that, in catalysts described herein, the nitrogen-containing ligand may have sufficiently ionic character to coordinate a metal center, such as a Mo or W metal center. Examples of nitrogen-containing ligands (e.g., having a plane of symmetry) include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. In one embodiment, $R^4$ and $R^5$ may be pyrrolyl groups. In some embodiments, the nitrogen-containing ligand may be chiral and may be provided as a racemic mixture or a purified stereoisomer. In some instances, the nitrogen-containing ligand having a plane of symmetry may be a group having the structure:

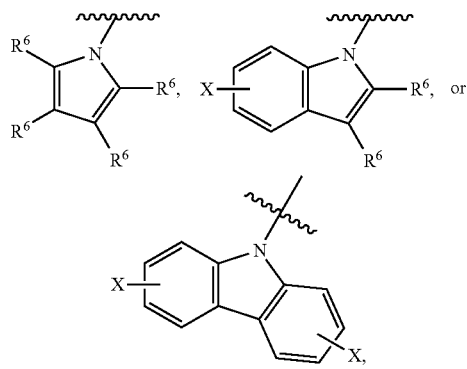

wherein each $R^6$ can be the same or different and is hydrogen, alkyl, heteroalkyl, aryl, heteroaryl, optionally substituted; and X may be present or absent and is any non-interfering group. As used herein, the term "non-interfering group," refers to any group (e.g., an organic group or permissible substituent to an organic group) which does not significantly effect or alter the properties (e.g., catalytic activity, solubility, etc.) of the compound.

In some cases, $R^1$ may be linked to form a ring with $R^2$ or $R^3$. For example, the metal complex may comprise $R^1$ linked to form a ring with $R^2$ or $R^3$ prior to use as a catalyst, and, upon initiation of the catalyst in a metathesis reaction, the linkage between $R^1$ and $R^2$ or $R^3$ may be broken, therefore rendering each of the ligands monodentate. The ring may comprise any number of carbon atoms and/or heteroatoms. In some cases, the cyclic olefin may comprise more than one ring. The ring may comprise at least 4, at least 5, at least 6, at least 7, at least 8, at least 9, at least 10, or more, atoms.

In some cases, $R^4$ and $R^5$ are joined together to form a chiral, bidentate ligand. In some cases, the ligand may be of at least 80% optical purity. Examples of chiral bidentate ligands include biphenolates and binaphtholates, optionally substituted with alkyl, alkenyl, alkynyl, cycloalkyl, cycloalkenyl, cycloalkynyl, aryl, alkaryl, aralkyl, optionally interrupted or terminated by heteroatoms, carbonyl groups, cyano, $NO_2$, alkoxy, aryloxy, hydroxy, amino, thioalkyl, thioaryl, sulfur-containing groups, halides, substituted derivatives thereof, and the like. In some cases, the chiral, bidentate ligand may be substituted at positions in proximity of the metal center to impart stereoselectivity to the reactive site of the catalyst.

Catalysts and/or catalyst precursors of the invention may comprise substituted imido groups (e.g., N—$R^1$). Without wishing to be bound by theory, the imido group may stabilize the organometallic compositions described herein by providing steric protection and/or reducing the potential for bimolecular decomposition. In some embodiments, $R^1$ may be aryl, heteroaryl, alkyl, or heteroalkyl, optionally substituted. In some cases, $R_1$ is aryl or alkyl. In some cases, $R^1$ may be selected to be sterically large or bulky, including phenyl groups, substituted phenyl groups (e.g., 2,6-disubstituted phenyls, 2,4,6-trisubstituted phenyls), polycyclic groups (e.g., adamantyl), or other sterically large groups. In some embodiments, $R^1$ may be 2,6-dialkylphenyl, such as 2,6-diisopropylphenyl. For example, in some embodiments, $R^1$ is

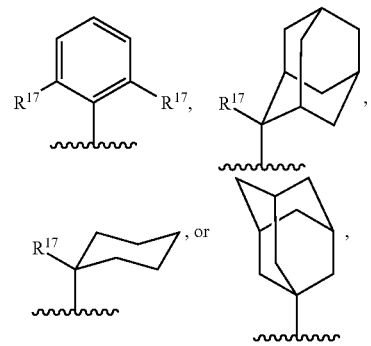

wherein each $R^{17}$ can be the same or different and is hydrogen, halogen, alkyl, heteroalkyl (e.g., alkoxy), aryl, acyl, or —OP, optionally substituted, where P is a protecting group.

In some cases, M is W, and $R^1$ is not

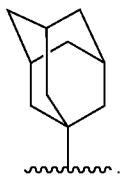

In some cases, M is W and $R^1$ is

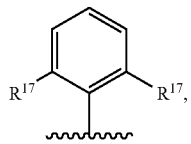

wherein each $R^{17}$ can be the same or different and is hydrogen, halogen, alkyl, heteroalkyl, aryl, acyl, or —OP, optionally substituted, and P is a protecting group.

In some embodiments, $R^1$ is

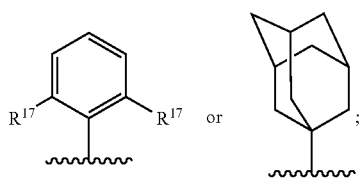

$R^2$ is $CMe_2Ph$ or $CMe_3$; and $R^4$ is an enantiomer of the following structure,

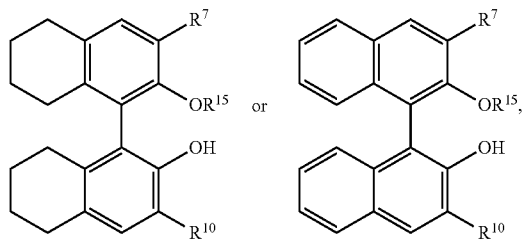

wherein each $R^{17}$ is the same or different and is halogen, methyl, t-butyl, $CF_3$, or aryl, optionally substituted, $R^5$ is a nitrogen-containing ligand having a plane of symmetry, and $R^7$, $R^{10}$, and $R^{15}$ are as described herein.

Catalysts and/or catalyst precursors of the invention may further comprise substituted alkylidene groups (e.g., $CR^2R^3$). The alkylidene groups may be mono-substituted (e.g., one of $R^2$ and $R^3$ is hydrogen) or di-substituted with, for example, alkyl, heteroalkyl, aryl, or heteroaryl groups, optionally substituted. In some cases, the alkylidene may be mono-substituted with, for example, t-butyl, dimethylphenyl, or the like. In some cases, $R^2$ is $CMe_2Ph$ or $CMe_3$, and $R^3$ is hydrogen.

In some cases, catalysts comprising one or more sterically large ligands may be synthesized. For example, at least one of $R^1$-$R^5$ may contain sterically large groups, such as tert-butyl, isopropyl, phenyl, naphthyl, adamantyl, substituted derivatives thereof, and the like. Sterically large ligands may also include ligands comprising substituents positioned in close proximity to the metal center when the ligand is bound to the metal. In some instances, when the catalyst comprising an oxygen containing ligand and a nitrogen containing ligand, the oxygen containing ligand may be sterically large.

In some embodiments, a catalyst may comprise one of the following structures:

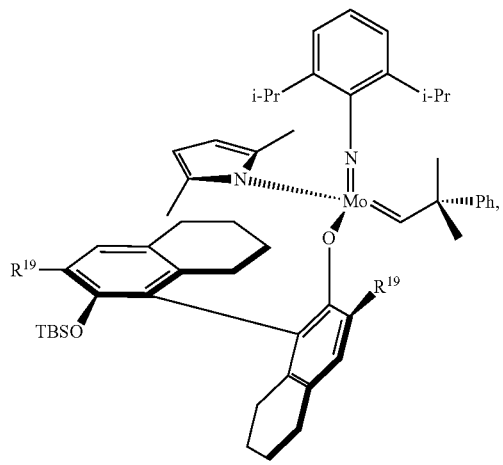

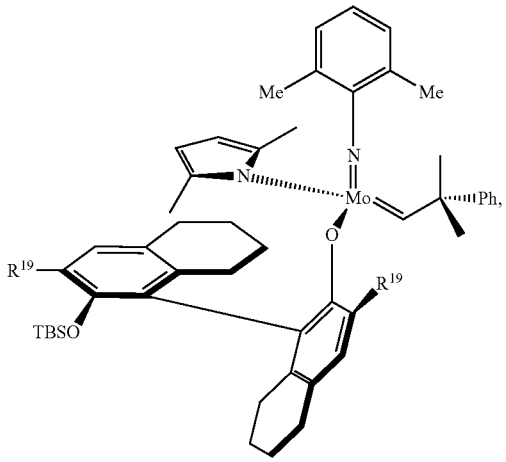

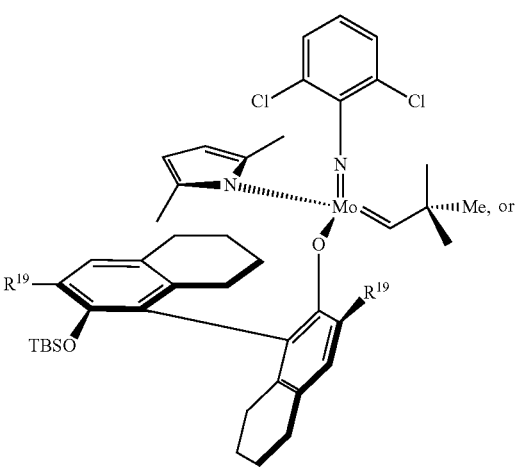

-continued

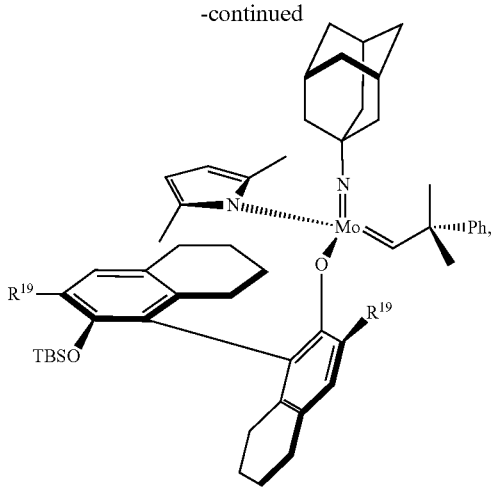

wherein R[19] is F, Cl, Br, or I. Other non-limiting examples of catalysts include M(NAr)(Pyr)(CHR₂)(OHIPT), M(NAr)(Pyr)(C₃H₆)(OHIPT), M(NAr)(CHCMe₂Ph)(Pyr)(BiphenTMS), M(NAr)(CHCMe₂Ph)(Me₂Pyr)(Br₂Bitet), M(NAr)(CHCMe₂Ph)(Me₂Pyr)(Mes₂Bitet), W(NAr)(CHCMe₂Ph)(Me₂Pyr)(OPhPh₄), M(NAr)(CHCMe₂Ph)(Pyr)((Trip)₂BitetTMS), M(NAr$^{Cl}$)(CHCMe₃)(Pyr)(BiphenTMS), M(NAr$^{Cl}$)(CHCMe₃)(Me₂Pyr)(OSi(TMS)₃), KNAr$^{Cl}$)(CHCMe₃)(Me₂Pyr)(OPhPh₄), M(NAr$^{Cl}$)(CHCMe₃)(Me₂Pyr)(HIPTO), M(NAr$^{Cl}$)(CHCMe₃)(Me₂Pyr)(HIPTO), M(NAr$^{Cl}$)(CHCMe₃)(Me₂Pyr)(Br₂Bitet), M(NAr$^{Cl}$)(CHCMe₃)(Me₂Pyr)(MesBitet), M(NAr$^{Cl}$)(CHCMe₃)(Pyr)(Mes₂Bitet), M(NAd)(Me₂Pyr)(CHR₂)(Br₂Bitet), M(NAr')(Pyr)(CHR₂)(Mes₂BitetOMe), M(NAd)(CHCMe₂Ph)(Me₂Pyr)(OSi(TMS)₃), M(NAd)(CHCMe₂Ph))(Me₂Pyr)(HIPTO), M(NAd)(CHCMe₂Ph)(Me₂Pyr)(MesBitet), M(NAr')(Pyr)(CHR₂)(OHIPT), M(NAr')(CHCMe₂Ph)(Me₂Pyr)(OSi(TMS)₃), M(NAr')(CHCMe₂Ph)(Me₂Pyr)(OPhPh₄), M(NAr')(CHCMe₂Ph)(Me₂Pyr)(HIPTO), M(NAr')(CHCMe₂Ph)(Me₂Pyr)(Br₂Bitet), M(NAr')(CHCMe₂Ph)(Pyr)(MesBitet), M(NAr')(CHCMe₂Ph)(Me₂Pyr)(MesBitet), M(NAr')(CHCMe₂Ph)(Pyr)(Mes₂BitetOMe), M(NAr')(CHCMe₂Ph)(Pyr)(Mes₂Bitet), etc., wherein M is Mo or W, Ar is 2,6-diisopropylphenyl, Ar$^{Cl}$ is 2,6-dichlorophenyl, Ar' is 2,6-dimethyphenyl, Ad is 1-admantyl, Mes is mesityl, Me₂Pyr is 2,5-dimethylpyrrolide, Pyr is pyrrolide, TBS is dimethyl-t-butylsilyl, Ts is tosyl, OTf is triflate, Trip is 2,4,6-triisopropylphenyl, HIPTO is hexaisopropylterphenolate, OSi(TMS)₃ is 1,1,1,3,3,3-hexamethyl-2-(trimethylsilyl)trisilan-2-olate, Biphen is 3,3'-di-tert-butyl-5,5',6,6'-tetramethylbiphenyl-2,2'-diol, BiphenTMS is 3,3'-di-tert-butyl-5,5',6,6'-tetramethyl-2'-(trimethylsilyloxy)biphenyl-2-olate, Bitet is 5,5',6,6',7,7',8,8'-octahydro-1,1'-binaphthyl-Trip₂Bitet is 3,3'-bis(2,4,6-triisopropylphenyl)-5,5',6,6',7,7',8,8'-octahydro-1,1'-binaphthyl-2,2'-diol, Trip₂BitetTMS is 3,3'-bis(2,4,6-triisopropylphenyl)-2'-(trimethylsilyloxy)-5,5',6,6',7,7',8,8'-octahydro-1,1'-binaphthyl-2-olate, Br₂Bitet is 3,3'-dibromo-2'-(tert-butyldimethylsilyloxy)-5,5',6,6',7,7',8,8'-octahydro-1,1'-binaphthyl-2-olate, MesBitet is 2'-(tert-butyldimethylsilyloxy)-3-mesityl-5,5',6,6',7,7',8,8'-octahydro-1,1'-binaphthyl-2-olate, Mes₂Bitet is 3,3'-dimesityl-2'-(tert-butyldimethylsilyloxy)-5,5',6,6',7,7',8,8'-octahydro-1,1'-binaphthyl-2-olate, and Mes₂BitetOMe is 3,3'-dimesityl-2'-methoxy-5,5',6,6',7,7',8,8'-octahydro-1,1'-binaphthyl-2-olate.

In some cases, the catalyst comprises a stereogenic metal atom. As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In a particular embodiment, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral, molecular product.

In some cases, when the catalyst comprises a stereogenic metal atom, and two or more ligands that bind the metal atom, each ligand associated with the metal complex comprises an organic group. The ligands may be monodentate ligands, i.e., the ligands bind the stereogenic metal atom via one site of the ligand (e.g., a carbon atom or a heteroatom of the ligand). In some cases, a monodentate ligand may bind the metal center via a single bond or a multiple bond. In some cases, the metal complex comprises at least one ligand lacking a plane of symmetry. That is, at least one ligand bound to the stereogenic metal atom is a chiral ligand. In some cases, the metal complex comprises an oxygen-containing ligand, including chiral and/or achiral oxygen-containing ligands. In some cases, the metal complex comprises a nitrogen-containing ligand, including chiral and/or achiral nitrogen-containing ligands. For example, the ligand may be a chiral or achiral nitrogen heterocycle, such as a pyrrolide. In some cases, the metal atom may be bound to at least one carbon atom. In some embodiments, the catalyst comprises the metal complex in a diastereomeric ratio greater than 1:1, greater than about 5:1, greater than about 7:1, greater than about 10:1, greater than about 20:1, or, in some cases, greater.

As suitable, the catalysts employed in the present invention may involve the use of metals which can mediate a particular desired chemical reaction. In general, any transition metal (e.g., having d electrons) may be used to form the catalyst, e.g., a metal selected from one of Groups 3-12 of the periodic table or from the lanthanide series. However, in some embodiments, the metal may be selected from Groups 3-8, or, in some cases, from Groups 4-7. In some embodiments, the metal may be selected from Group 6. According to the conventions used herein, the term "Group 6" refers to the transition metal group comprising chromium, molybdenum, and tungsten. In some cases, the metal is molybdenum or tungsten. In some embodiments, the metal is not ruthenium. It may be expected that these catalysts will perform similarly because they are known to undergo similar reactions, such as metathesis reactions. However, the different ligands are thought to modify the catalyst performance by, for example, modifying reactivity, and preventing undesirable side reactions. In a particular embodiment, the catalyst comprises molybdenum. Additionally, the present invention may also include the formation of heterogeneous catalysts containing forms of these elements.

In some cases, a catalyst may be a Lewis base adduct. The terms "Lewis base" and "Lewis base adduct" are known in the art and refer to a chemical moiety capable of donating a pair of electrons to another chemical moiety. For example, the metal complex may be combined with tetrahydrofuran (THF), wherein at least one THF molecules coordinate the metal center to form a Lewis base adduct. In some cases, the Lewis base adduct may be $PMe_3$. In some embodiments, the catalyst may be formed and stored as a Lewis base adduct, and may be "activated" in a subsequent reaction step to restore the catalyst that does not comprise a Lewis base adduct.

Those of ordinary skill in the art will be aware of methods to synthesize catalysts described herein for use in a metathesis reaction. The catalysts may be isolated, or may be formed in situ and utilized in a subsequent reaction (e.g. one-pot reaction). The term "one-pot" reaction is known in the art and refers to a chemical reaction which can produce a product in one step which may otherwise have required a multiple-step synthesis, and/or a chemical reaction comprising a series of steps that may be performed in a single reaction vessel. One-pot procedures may eliminate the need for isolation (e.g., purification) of catalysts and/or intermediates, while reducing the number of synthetic steps and the production of waste materials (e.g., solvents, impurities). Additionally, the time and cost required to synthesize catalysts and/or other products may be reduced. In some embodiments, a one-pot synthesis may comprise simultaneous addition of at least some components of the reaction to a single reaction chamber. In one embodiment, the one-pot synthesis may comprise sequential addition of various reagents to a single reaction chamber.

In some embodiments, a catalyst having the structure (I) where M is M or W may be prepared according to the following procedure. Molybdate or tungstate, for example ammonium molybdate (e.g., $(NH_4)_2Mo_2O_7$), alkylammonium molybdate (e.g., $[Mo_8O_{26}][CH_3N(C_8H_{17})_3]_4$, $[Mo_8O_{26}][N(C_{12}H_{25})_3]_4$), or their equivalent, may be combined under an inert atmosphere with amine of the general formula $NHXR^1$, where $R^1$ is as defined herein, and where X is hydrogen or trimethylsilyl (e.g., $(CH_3)_3SiNHAr$, where Ar is an aryl or heteroaryl group). A compound capable of deprotonating $NHXR^1$, for example, triethylamine, pyridine, substituted pyridine or other equivalent nitrogen bases and halogenating or triflating agents (e.g., $Me_3SiCl$, $Me_3SiBr$, $Me_3SiSO_3CF_3$ or their equivalent) may be added to the reaction mixture. A suitable solvent may be employed which may or may not contain an equivalent amount of coordinating Lewis base (e.g., 1,2-dimethoxyethane (DME), tetrahydrofuran (THF), pyridine, quinuclidine, $(R)_2PCH_2CH_2P(R)_2$, and $P(R)_3$ where R=alkyl, aryl), and the reaction mixture may be heated to approximately 60-70° C. for at least about 6 hours under an inert atmosphere (e.g., a nitrogen atmosphere), thereby yielding $Mo(NR^1)_2(halogen)_2(Lewis base)_x$ where x is 0, 1 or 2.

The reaction product may be retained in solution or isolated as a solid by the evaporation of the volatile components from solution using distillation techniques. Treatment of the compound with two equivalents of a Grignard or lithium reagent (or equivalent), such as $ClMgCHR^2R^3$, may lead to the production of an intermediate, having the general formula $M(NR^1)_2(CHR^2R^3)_2$, where $R^1$, $R^2$ and $R^3$ have been previously defined. This complex may then be treated with three equivalents of a strong acid, such as triflic acid ($HOSO_2CF_3$), in 1,2-dimethoxyethane (DME, or other suitable solvent), thereby generating a six coordinate complex, $M(NR^1)(CR^2R^3)(OSO_2CF_3)_2 \cdot (DME)$ (or other equivalent). One equivalents of $YR^4$ and $YR^5$ (where $R^4$ and $R^5$ are as previously defined and Y is H, Li, Na, K, etc.) or two equivalents of $YR^4$ (when $R^4$ and $R^5$ are the same) or one equivalent of a bidentate ligand (when $R^4$ and $R^5$ are joined together to form a bidentate ligands) may be reacted with this complex to yield a catalyst having a structure $M(NR^1)(CR^2R^3)(R^4)(R^5)$.

In some embodiments, the catalyst may be formed and isolated or generated in situ from a catalyst precursor having the structure (II)

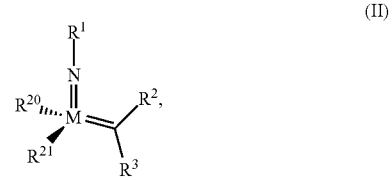

(II)

wherein M is Mo or W; $R^1$ is alkyl, heteroalkyl, aryl, or heteroaryl, optionally substituted; $R^2$ and $R^3$ can be the same or different and are hydrogen, alkyl, alkenyl, heteroalkyl, heteroalkenyl, aryl, or heteroaryl, optionally substituted; $R^{20}$ and $R^{21}$ can be the same or different and are heteroalkyl or heteroaryl, optionally substituted, or $R^{20}$ and $R^{21}$ are joined together to form a bidentate ligand with respect to M, optionally substituted; and wherein $R^{20}$ and $R^{21}$ each comprise at least one nitrogen atom (e.g., are nitrogen-containing ligands). In some cases, $R^{20}$ and $R^{21}$ each coordinate M via a nitrogen atom. For example, $R^{20}$ and $R^{21}$ may both be pyrrolyl groups which coordinate the metal via the nitrogen atoms of the pyrrolyl ring. The nitrogen-containing ligand may be selected to interact with an oxygen-containing ligand such that an oxygen-containing ligand can readily replace an nitrogen-containing ligand to generate the catalyst.

As shown by the illustrative embodiment in Scheme 1, a catalyst may be formed from catalyst precursor (II) by reacting the catalyst precursor with an oxygen-containing ligand (e.g., $R^4$ and $R^5$) such that the oxygen-containing ligand replaces $R^{20}$ and $R^{21}$ to form the catalyst having the structure (III), wherein $R^{20}$ and $R^{21}$, in protonated or non-protonated form, may be released. $R^4$ and $R^5$ may be oxygen-containing ligands or $R^4$ and $R^5$ may be joined together to form a bidentate, oxygen-containing ligand. In some embodiments, only one of $R^{20}$ or $R^{21}$ is reacted with an oxygen-containing ligand to form a catalyst, for example, having the structure (IV) or (V), as shown in Scheme I.

Scheme 1

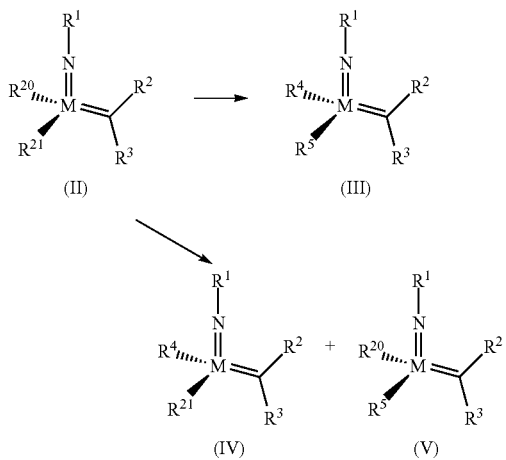

In some cases, the oxygen-containing ligand may be in a protonated form prior to coordinating the metal center, and may then have sufficiently ionic character (e.g., may be deprotonated) upon coordination to the metal center. Similarly, the nitrogen-containing ligand may be in a deprotonated form when bound to the metal center, and may become protonated upon release from the metal center. For example, $R^{20}$ and $R^{21}$ may be pyrrolyl groups coordinating the metal center such that, upon exposure of the catalyst precursor to an oxygen-containing ligand such as biphenolate, the biphenolate ligand may replace the pyrrolyl groups to form the catalyst, resulting in the release of two equivalents of pyrrole. Ligands of the present invention may be described using nomenclature consistent with their protonated or deprotonated forms, and, in each case, it should be understood that the ligand will adopt the appropriate form to achieve its function as, for example, either a ligand bound to a metal center or an inert species in the reaction mixture. For example, in an illustrative embodiment, the term "pyrrolyl" may be used to describe a deprotonated, anionic pyrrole group which may coordinate a metal center, while the term "pyrrole" may be used to describe a neutral pyrrole group which does not coordinate the metal center but may be present in solution as an inert species that does not react with other components in the reaction mixture.

In cases where the catalyst may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. That is, $R^{20}$ and $R^{21}$ may be selected such that the released $R^{20}$ and/or $R^{21}$ groups may not interfere with subsequent reactions that may involve the catalyst or may not react with any other species in the reaction. In some cases, the $R^{20}$ and $R^{21}$ groups may be released in protonated form (e.g., $H-R^{20}$ and $H-R^{21}$, or $H_2(R^{20}-R^{21})$) but may be similarly inert to other species or reagents, including those involved in subsequent reactions. Those of ordinary skill in the art would be able to select the appropriate nitrogen-containing ligand(s) (e.g., $R^{20}$ and $R^{21}$) suitable for use in a particular application, e.g., such that the released nitrogen-containing ligand(s) do not contain carbon-carbon double bonds which may react with the generated olefin metathesis catalyst.

In some embodiments, a catalyst comprising a stereogenic metal center may be produced by reacting an organometallic composition (e.g., a catalyst precursor) having a plane of symmetry with a monodentate ligand lacking a plane of symmetry, to produce a catalyst comprising a stereogenic metal atom. In some cases the method may comprise reacting a racemic mixture of an organometallic composition comprising a stereogenic metal center with a monodentate ligand lacking a plane of symmetry, to produce a metal complex comprising a stereogenic metal atom. The metal complex may comprise two or more ligands, wherein each ligand binds the stereogenic metal atom via one bond, i.e., each ligand is a monodentate ligand. In some cases, the method may comprise providing a catalyst precursor comprising an organometallic composition having a plane of symmetry and including two or more ligands, in a reaction vessel. At least one ligand may be replaced by a monodentate ligand (e.g., oxygen-containing or nitrogen-containing ligand), thereby synthesizing a metal complex comprising the stereogenic metal atom.

As described herein, the combination of imido, alkoxide, and/or alkylidene ligands may be selected to suit a particular application. For example, in some cases, sterically large or sterically bulky ligands and/or ligand substituents may impart a higher degree of stability to a catalyst, while, in some cases, lowering the reactivity of the catalyst. In some cases, smaller ligands and/or substituents may generate more reactive catalysts that may have decreased stability. In some embodiments, a sterically large or sterically bulky alkoxide ligand may be useful for forming the Z-isomer of the product as compared to a less sterically large or bulky alkoxide ligand. Those of ordinary skill in the art would be able to balance such factors and select the appropriate combination of ligands for catalysts of the invention.

The catalyst (or catalyst precursor) may be provided in the reaction mixture in a sub-stoichiometric amount (e.g., catalytic amount). In certain embodiments, that amount is in the range of about 0.01 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 4 mol %, less than about 3 mol %, less than about 2 mol %, less than about 1 mol %, less than about 0.5 mol %, or less, relative to the limiting reagent. In some cases, the catalyst is present in about 0.5 mol %, about 1 mol %, about 2 mol %, about 4 mol %, about 5 mol %, about 10 mol %, or the like. In the case where the molecular formula of the catalyst complex includes more than one metal, the amount of the catalyst complex used in the reaction may be adjusted accordingly.

In some cases, the metathesis reactions described herein may be performed in the absence of solvent (e.g., neat). In some cases, the metathesis reactions may be conducted in the presence of one or more solvents. Examples of solvents that may be suitable for use in the invention include, but are not limited to, benzene, p-cresol, toluene, xylene, mesitylene, diethyl ether, glycol, petroleum ether, hexane, cyclohexane, pentane, dichloromethane (or methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like.

The metathesis reaction may be carried out at any suitable temperature. In some cases, the reaction is carried out at about room temperature (e.g., about 25° C., about 20° C., between about 20° C. and about 25° C., or the like). In some cases, however, the reaction may be carried out at a temperature below or above room temperature, for example, at about −70° C., about −50° C., about −30° C., about −10° C., about −0° C., about 10° C., about 30° C., about 40° C., about 50° C., about 60° C., about 70° C., about 80° C., about 90° C., about 100° C., about 120° C., about 140° C., or the like. In some embodiments, the reaction may be carried out at more than one temperature (e.g., reactants added at a first temperature and the reaction mixture agitated at a second wherein the transition from a first temperature to a second temperature may be gradual or rapid).

The metathesis reaction may be allowed to proceed for any suitable period of time. In some cases, the reaction is allowed to proceed for about 10 minutes, about 20 minutes, about 30 minutes, about 40 minutes, about 50 minutes, about 1 hour, about 2 hours, about 4 hours, about 8 hours, about 12 hours, about 16 hours, about 24 hours, about 28 hours, or the like. In some cases, aliquots of the reaction mixture may be removed and analyzed at an intermediate time to determine the progress of the reaction.

As used herein, the term "reacting" refers to the formation of a bond between two or more components to produce a compound. In some cases, the compound is isolated. In some cases, the compound is not isolated and is formed in situ. For example, a first component and a second component may react to form one reaction product comprising the first component and the second component joined by a covalent bond (e.g., a bond formed between a ligand and a metal, or a bond formed between two substrates in a metathesis reaction). That is, the term "reacting" does not refer to the interaction of solvents, catalysts, bases, ligands, or other materials which may serve to promote the occurrence of the reaction with the component(s).

As used herein, the term "organic group" refers to any group comprising at least one carbon-carbon bond and/or carbon-hydrogen bond. For example, organic groups include alkyl groups, aryl groups, acyl groups, and the like. In some cases, the organic group may comprise one or more heteroatoms, such as heteroalkyl or heteroaryl groups. The organic group may also include organometallic groups. Examples of groups that are not organic groups include —NO or —$N_2$. The organic groups may be optionally substituted, as described below.

The term "organometallic" is given its ordinary meaning in the art and refers to compositions comprising at least one metal atom bound to one or more than one organic ligands. In some cases, an organometallic compound may comprise a metal atom bound to at least one carbon atom.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (e.g., see Greene, T. W.; Wuts, P. G. M. *Protective Groups in Organic Synthesis*, $2^{nd}$ ed.; Wiley: New York, 1991).

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

The term "heteroalkyl" is given its ordinary meaning in the art and refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls, and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like. The term "heteroaryl" is given its ordinary meaning in the art and refers to aryl groups as described herein in which one or more atoms is a heteroatom (e.g., oxygen, nitrogen, sulfur, and the like), optionally substituted. Examples of aryl and heteroaryl groups include, but are not limited to, phenyl, aryloxy, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like.

It will also be appreciated that aryl and heteroaryl moieties, as defined herein, may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)-heteroaryl moieties. Thus, as used herein, the phrases "aryl or heteroaryl" and "aryl, heteroaryl, (aliphatic) aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable.

The term "olefin," as used herein, refers to any species having at least one ethylenic double bond such as normal and branched chain aliphatic olefins, cycloaliphatic olefins, aryl substituted olefins and the like. Olefins may comprise terminal double bond(s) ("terminal olefin") and/or internal double bond(s) ("internal olefin") and can be cyclic or acyclic, linear or branched, optionally substituted. The total number of carbon atoms can be from 1 to 100, or from 1 to 40; the double bonds of a terminal olefin may be mono- or bi-substituted and the double bond of an internal olefin may be bi-, tri-, or tetrasubstituted. In some cases, an internal olefin is bisubstituted.

The term "cyclic olefin," as used herein, refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "halogen" or "halide" designates —F, —Cl, —Br, or —I.

The term "alkoxy" refers to the group, —O-alkyl.
The term "aryloxy" refers to the group, —O-aryl.
The term "acyloxy" refers to the group, —O-acyl.
The term "arylalkyl," as used herein, refers to an alkyl group substituted with an aryl group.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence.

The term "dialkyl amine" is art-recognized and can be represented by the general formula: N(R')(R'')$^-$, wherein R' and R'' are alkyl groups.

An "alkoxide" ligand herein refers to a ligand prepared from an alcohol, in that removing the hydroxyl proton from an alcohol results in a negatively charged alkoxide.

The term "silyloxy," as used herein, represents —OSi(R$^{22}$)$_3$, wherein each R$^{22}$ can be the same or different and may be alkyl, aryl, heteroalkyl, or heteroaryl, optionally substituted. Non-limiting examples of silyloxy groups include —OSiPh$_3$, —OSiMe$_3$, and —OSiPh$_2$Me.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For example, a substituted alkyl group may be CF$_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

Example 1

The following example describes highly Z-selective olefin homo-metathesis, according to non-limiting embodiments. Highly reactive MonoAryloxide-Pyrrolide (MAP) olefin metathesis catalysts of Mo (e.g., see FIG. 1) have been prepared from bispyrrolide precursors in situ and employed for select metathesis reactions. See, for example, Schrock, R. R., Chem. Rev., 2009, 109, 3211; Hock, A., et al., J. Am. Chem. Soc., 2006, 128, 16373; and Singh, R., et al., J. Am. Chem. Soc., 2007, 129, 12654. A MAP catalyst generally comprises an imido ligand, and alkylidene ligand, an oxygen-containing ligand, and a nitrogen-containing ligand associated with a metal center.

A possible mechanism of Z-selective homo-coupling of R$_1$CH═CH$_2$ (e.g., a mono-substituted terminal olefin) via a (syn, rac) MAP catalyst is shown in FIG. 2. Generally, only syn isomers are observed by NMR or X-ray studies of MAP catalysts. A terminal olefin may enter the coordination sphere trans to the pyrrolide (Pyr) to yield an intermediate metallacyclobutane with adjacent R$_1$ substituents. In some instances, OR''' may be "large" enough to prevent formation of any metallacycle in which R$_1$ points toward OR''', thereby leading to the formation of a metallacyclobutane with adjacent R$_1$ substituent pointing away from the axial OR''' group, leading to the formation of the Z-isomer of the product. Loss of Z—R$_1$CH═CHR$_1$ yields an intermediate methylene species with an inverted configuration at the metal center (S→R in FIG. 2). A productive metathesis reaction between the methylene species and R$_1$CH═CH$_2$ then yields ethylene and reforms (S)-M(NR)(CHR$_1$)(Pyr)(OR'''). Inversion of configuration at the metal center is a consequence of each forward metathesis step, but inversion itself may not be an important feature of a homo-coupling reaction. However, if OR''' is enantiomerically pure, then both diastereomers may be fully functional.

Figure 3:
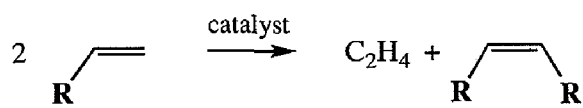
FIG. 3 shows a homo-metathesis reaction, according to some embodiments.

Initially, experiments were conducted on a small scale involving 1-hexene (S$_1$) or 1-octene (S$_2$; Table 2; equation in FIG. 3) with 4 mol % catalyst in a closed system (NMR tube). Note that a catalyst that was successful for metathesis of cis-4-octene with cis-3-hexene (2$_m$, in Table 1) is not satisfactory for 1-octene under these conditions. On the basis of extensive screening (see results in Example 2) it appears that in some cases, a "small" imido group is not necessary required, in some cases, for highly Z-selective couplings of a terminal olefin, and (ii) that catalysts comprising W may have improved performance over the related Mo analogs. The tungstacyclobutane initiator (4$_w$) performed in a manner identical to $3_w$, and 95% Z product was obtained at low conversion. Not surprisingly, the Z product isomerizes to the E-isomer with time and conversion (e.g., see $5_w$). The results for the homo-coupling of 1-hexene were similar to those shown in Table 1 in all cases; for example, catalyst $4_w$ gave 95% Z-5-decene at 33% conversion (3 days).

TABLE 1

Homo-coupling of 1-octene ($S_2$).

| | Catalyst | Time | % Conv. | % Z |
|---|---|---|---|---|
| $2_{Me}$ | Mo(NAd)(Me$_2$Pyr)(CHR$_2$)(OHIPT)[b] | 3 h | 43 | 68 |
| $3_{Mo}$ | Mo(NAr)(Pyr)(CHR$_2$)(OHIPT)[b] | 20 m | 80 | 40 |
| $3_W$ | W(NAr)(Pyr)(CHR$_2$)(OHIPT)[b] | 26 h | 88 | 88 |
| $4_W$ | W(NAr)(Pyr)(C$_3$H$_6$)(OHIPT) | 3 h | 33 | 95 |
| $5_{Mo}$ | Mo(NAr)(Pyr)(CHR$_2$)(Mes$_2$Bitet)*[b] | 15 m | 58 | 70 |
| $5_W$ | W(NAr)(Pyr)(CHR$_2$)(Mes$_2$Bitet)*[b] | 30 m | 38 | 93 |
| $5_W$ | W(NAr)(Pyr)(CHR$_2$)(Mes$_2$Bitet)*[b] | 2 h | 72 | 88 |

In Table 1, (a) 4 mol % cat in C$_6$D$_6$ at 22° C.; (b) Prepared in situ, see Example 2 (*new catalyst). R$_2$=CMe$_2$Ph; Ad=1-adamantyl. Ar=2,6-i-Pr$_2$C$_6$H$_3$. HIPTO is the aryloxide shown in structure 2 (FIG. 1). Mes$_2$Bitet is the ligand in structure 1 with R'''=mesityl (FIG. 1).

A selection of some additional results using substrates $S_3$-$S_9$ are shown in Table 2. (See Example 2 for more extensive lists.) Note that $7_{Mo}$ and $3_w$ perform equally well for $S_7$, although a direct comparison of Mo and W is not possible since W 1-adamantyl imido species are generally not known. It should be noted also that although high conversion is usually desirable, it is not necessary required in view of the relative ease of separation of starting material from product.

TABLE 2

Select screening results of substrates $S_3$-$S_9$.

| $S_n$ | | Catalyst | T (h) | % Conv. | % Z |
|---|---|---|---|---|---|
| $S_3$ | $3_W$ | W(NAr)(Pyr)(CHR$_2$)(OHIPT)[b] | 3 | 40 | 91 |
| $S_3$ | $4_W$ | W(NAr)(Pyr)(C$_3$H$_6$)(OHIPT) (2%) | 14 | 52 | 94 |
| $S_3$ | $6_W$ | N(NAr$^{Cl}$)(Pyr)(CHR$_2$)(Mes$_2$Bitet)*[b] | 3 | 62 | 93 |
| $S_4$ | $7_{Mo}$ | Mo(NAd)(Me$_2$Pyr)(CHR$_2$)(Br$_2$Bitet)[b] | 3 | 33 | 98 |
| $S_5$ | $8_W$ | W(NAr')(Pyr)(CHR$_2$)(Mes$_2$BitetOMe)*[b] | 1.5 | 69 | 92 |
| $S_6$ | $9_W$ | W(NAr')(Pyr)(CHR$_2$)(OHIPT)*[b] | 3 | 33 | 90 |
| $S_7$ | $3_W$ | W(NAr)(Pyr)(CHR$_2$)(OHIPT)[b] | 3 | 30 | 94 |
| $S_7$ | $10_W$ | W(NAr$^{Cl}$)(Pyr)(CHR$_3$)(OHIPT)* | 1.5 | 70 | 96 |
| $S_7$ | $7_{Mo}$ | Mo(NAd)(Me$_2$Pyr)(CHR$_2$)(Br$_2$Bitet)[b] | 3 | 24 | 98 |
| $S_8$ | $11_W$ | W(NAr$^{Cl}$)(Pyr)(CHR$_3$)(Mes$_2$Bitet)*[b] | 1.5 | 70 | 96 |
| $S_9$ | $11_W$ | W(NAr$^{Cl}$)(Pyr)(CHR$_2$)(Mes$_2$Bitet)*[b] | 3 | 52 | 98 |

In Table 2, (a) 4 mol % cat in C$_6$D$_6$ at 22° C. (b) Prepared in situ; see Example 2 (*new catalyst). R$_2$=CMe$_2$Ph. Ar$^{Cl}$=2,6-Cl$_2$C$_6$H$_3$. Ar'=2,6-Me$_2$C$_6$H$_3$. Br$_2$Bitet is the ligand in structure 1 with R'''=Br (FIG. 1). Mes$_2$BitetOMe is the methyl-protected analog of the ligand in structure 1 with R'''=Mesityl; R$_3$=t-Bu (FIG. 1).

In order to determine what, if any, effect the presence of ethylene has on the Z-selectivity of the reactions, reactions were explored which involved several of the higher boiling substrates under a good to moderate vacuum (0.5 or 10 mmHg) with 1% catalyst on larger scales, and these findings were compared with those obtained at 1 atm of nitrogen. Some loss of monomer at ~0.5 mm naturally was observed over long reaction times, in some cases. The results shown in Table 3 suggest that the effects of carrying out reactions at reduced pressure are not dramatic.

TABLE 3

The effect of reduced pressure on Z content (1% cat).

| Substrate | Cat | Press (mmHg) | T (h) | % Conv. | % Z |
|---|---|---|---|---|---|
| $S_5$ | $8_W$ | ~0.5 | 0.2 (15) | 25 (>98) | >98 (>98[b]) |
| $S_5$ | $8_W$ (2%) | ~760 | 1.5 (15) | 84 (86) | 97 (88) |
| $S_5$ | $12_{Mo}{}^c$ | ~0.5 | 0.6 (16) | 36 (34) | 61 (61) |
| $S_5$ | $12_{Mo}{}^c$ | ~760 | 0.6 (16) | 24 (24) | 61 (59) |
| $S_5$ | $4_W$ | ~0.5 | 5 (21) | 7 (22) | >98 (>98) |
| $S_5$ | $4_W$ | ~760 | 5 (21) | 10 (27) | >98 (>98) |
| $S_5$ | $3_{Mo}$ | 10 | 19 | 62 | 88 |
| $S_5$ | $3_{Mo}$ | ~760 | 19 | 42 | 90 |
| $S_7$ | $3_{Mo}$ | ~0.5 | 2 | 64 | 94 |
| $S_7$ | $3_{Mo}$ | ~760 | 2 | 52 | 96 |
| $S_{10}$ | $12_{Mo}$(2%) | ~0.5 | 14 | 70 | 95 |

In Table 3, (a) Reaction scale ~200 mg, neat substrate, catalyst added as a solid. (b) [b] 86% yield. (c) $12_{Mo}$=Mo(NAr)(Pyr)(CHR$_2$)(Mes$_2$BitetOMe).

The results of reactions carried out at elevated temperatures, including refluxing temperature for suitable substrates, larger scales, and lower % catalyst are shown in Table 4. In several cases the remaining monomer was removed in vacuo and the Z product yields were established. Several reactions afforded products with >90% Z content in good yield. Higher temperatures and lower catalyst loadings appear to give the best results.

TABLE 4

Reactions carried out at elevated temperatures.[a]

| Substrate | Catalyst | % | time (h) | ° C. (B ath) | % Conv. | % Z | % Yield |
|---|---|---|---|---|---|---|---|
| $S_1$ | $4_W$ | 0.4 | 48 | 80 | 72 | 95 | 58 |
| $S_2$ | $4_W$ | 0.4 | 24 | 120 | 94 | 86 | 78 |
| | $10_W$ | 0.2 | 3 | 120 | >98 | 77 | 77 |
| $S_3$ | $4_W$ | 0.2 | 4 | 120 | 63 | 93 | 56 |
| | $10_{Wb}$ | 0.2 | 24 | 100 | 94 | 88 | 65 |
| $S_4$ | $13_{Wb}$ | 0.2 | 18 | 90 | 28 | 86 | 26 |
| $S_5$ | $13_{Wb}$ | 2 | 23 | 100 | >97 | 95 | |
| $S_6$ | $13_W$ | 1 | 16 | 100 | 97 | 87 | 80 |
| $S_7$ | $4_W$ | 0.2 | 1 | 100 | 46 | 91 | |
| | $10_W$ | 0.2 | 18 | 100 | 74 | 94 | |
| $S_8$ | $5_W$ | 4 | 24 | 100 | 46 | >98 | 42 |
| $S_9$ | $4_W$ | 4 | 18 | 100 | 95 | 91 | 90 |
| | $10_W$ | 4 | 24 | 90 | 50 | 94 | 36 |

In Table 4, (a) Reaction scale ~0.5 g to ~4 g; catalyst was dissolved in ~1 mL of benzene and substrate was added in one portion. The mixture was refluxed with a condenser at elevated temperatures under an atmosphere of N$_2$. (b) W(NAr')(Pyr)(C$_3$H$_6$)(OHIPT).

It may be postulated that the mechanism of formation of Z product is that shown in FIG. 2, and that a ligand combination may be selected such that the majority of the intermediate forms is an alpha,R$_1$/beta,R$_1$ metallacyclobutane intermediate from a syn alkylidene. Thus, in some embodiments, a large OR''' ligand may be required in order to form Z product with high selectivity. In addition, a "small" imido group may not be required, as the steric demands of the required syn-alpha, R$_1$/beta, R$_1$ metallacyclobutane intermediate are not as pronounces as the steric demands of an all cis, trisubstituted metallacyclobutane.

Three possible modes of "direct" formation (e.g., not isomerization of the Z product) of an E product may be considered: (i) approach of monomer to the syn alkylidene to yield a metallacycle with R$_1$ pointed toward OR'''; (ii) reaction of monomer with a highly reactive (unobservable) anti alkylidene (in equilibrium with a syn alkylidene) to give a trans disubstituted metallacyclobutane intermediate; or (iii) approach of the monomer in a manner different from that shown in FIG. 2 to yield a different type of metallacyclobutane intermediate. A significant amount of E product, in most cases, is not formed through a "direct" method if OR''' is sufficiently large.

One possible "indirect" mode of formation E product is isomerization of the Z-product through reaction with an M=CHR$_1$ species to give a trisubstituted metallacycle intermediate that contains two adjacent trans R$_1$ substituents. This reaction is likely to be relatively slow in many circumstances for steric reasons because two R$_1$ groups must point toward the large OR''' group in the metallacyclobutane intermediate. A second, non-limiting, indirect mode is for the reverse of the reaction shown in FIG. 1 to be fast. If the monomer is reformed and recoupled many times in the presence of ethylene, then a "mistake" that results in formation of E product in any single step (equation 1 and immediately above) is greatly magnified. On the basis of the results shown in Table 3, rapid ethenolysis, in most embodiments, is likely not the main mechanism of forming E product with the catalysts and substrates explored in this example.

Example 2

The following example outlines synthetic procedures and method employed in Example 1, as well as additional examples of reaction substrates and catalysts.

Abbreviations. Ar: 2,6-diisopropylphenyl; Ar$^{Cl}$:2,6-dichlorophenyl; Ar': 2,6-dimethyphenyl; Ad: 1-admantyl; Mes: mesityl; Me$_2$Pyr: 2,5-dimethylpyrrolide; Pyr: pyrrolide; TBS: dimethyl-t-butylsilyl; Ts: tosyl; OTf: triflate; Trip: 2,4,6-triisopropylphenyl; HIPTO: hexaisopropylterphenolate; OSi(TMS)$_3$: 1,1,1,3,3,3-hexamethyl-2-(trimethylsilyl)trisilan-2-olate; Biphen: 3,3'-di-tert-butyl-5,5',6,6'-tetramethylbiphenyl-2,2'-diol; BiphenTMS: 3,3'-di-tert-butyl-5,5',6,6'-tetramethyl-2'-(trimethylsilyloxy)biphenyl-2-olate; Bitet: 5,5',6,6',7,7',8,8'-octahydro-1,1'-binaphthyl-2,2'-diol; Trip$_2$Bitet: 3,3'-bis(2,4,6-triisopropylphenyl)-5,5',6,6',7,7',8,8'-octahydro-1,1'-binaphthyl-2,2'-diol; Trip$_2$BitetTMS: 3,3'-bis(2,4,6-triisopropylphenyl)-2'-(trimethylsilyloxy)-5,5',6,6',7,7',8,8'-octahydro-1,1'-binaphthyl-2-olate; Br$_2$Bitet: 3,3'-dibromo-2'-(tert-butyldimethylsilyloxy)-5,5',6,6',7,7',8,8'-octahydro-1,1'-binaphthyl-2-olate; MesBitet: 2'-(tert-butyldimethylsilyloxy)-3-mesityl-5,5',6,6',7,7',8,8'-octahydro-1,1'-binaphthyl-2-olate; Mes$_2$Bitet: 3,3'-dimesityl-2'-(tert-butyldimethylsilyloxy)-5,5',6,6',7,7',8,8'-octahydro-1,1'-binaphthyl-2-olate; Mes$_2$BitetOMe: 3,3'-dimesityl-2'-methoxy-5,5',6,6',7,7',8,8'-octahydro-1,1'-binaphthyl-2-olate Substrates. S1-CH$_2$=CH(CH$_2$)$_3$CH$_3$; S2-CH$_2$=CH(CH$_2$)$_5$CH$_3$; S3-CH$_2$=CHCH$_2$Ph; S4-CH$_2$=CHCH$_2$(Bpin); S8-CH$_2$=CHCH$_2$OBn; S9-CH$_2$=CHCH$_2$NHTs; S10-CH$_2$CHCH$_2$NHPh; S11-CH$_2$=CHCH$_2$(OTBs); S12-CH$_2$=CHCH$_2$Cy.

General Comments. Glassware was oven-dried at 175° C. and purged with nitrogen on a dual-manifold Schlenk line or cooled in the evacuated antechamber of a nitrogen-filled glovebox. Experiments were either conducted in a nitrogen drybox or an air free dual-manifold Schlenk line. NMR spectra were obtained from Varian 300 or 500 MHz spectrometer, reported in δ (parts per million) relative to tetramethylsilane, and referenced to the residual $^1$H/$^{13}$C signals of the deuterated solvent ($^1$H (δ): benzene 7.16; chloroform 7.27; methylene chloride 5.32. $^{13}$C (δ): benzene 128.39; chloroform 77.23; methylene chloride 54.00). Midwest Microlab, LLC. provided the elemental analyses results. All reagents were used without further purification unless noted otherwise. Pentane was washed with H$_2$SO$_4$, followed by water, and saturated aqueous NaHCO$_3$, and dried over CaCl$_2$ pellets over at least two weeks prior to use in the solvent purification system. HPLC grade diethyl ether, toluene, tetrahydrofuran, pentane, and methylene chloride were sparged with nitrogen and passed through activated alumina; in addition, benzene was passed through a copper catalyst; organic solvents were then stored over activated 4 Å Linde-type molecular sieves. Benzene-d$_6$ was dried over sodium ketal, degassed, vacuum-transferred and stored over activated 4 Linde-type molecular sieves. LiMe$_2$Pyr was synthesized by treating n-BuLi to freshly distilled 2,5-dimethylpyrrole in Et$_2$O chilled at −27° C., filtering off the salt and drying it in vacuo provided the desired LiMe$_2$Pyr. LiPyr was isolated in following similar procedures. N-allyl-4-methylbenzenesulfonamide (S$_9$) was prepared from allylic amine and tosyl chloride, and recrystallized from a concentrated solution of hexanes and diethyl ether. 1-hexene, 1-octene, allylbenzene, allyltrimethylsilane, allylboronic acid pincol ester, allylcyclohexane, and allyloxy(tert-butyl)dimethylsilane were dried over CaH$_2$ and vacuum transferred. Allylbenzylether was dried over CaH$_2$ and distilled. Methyl-10-undecenoate was dried over P$_2$O$_5$ and vacuum transferred. 2,3,5,6-tetraphenylphenol (HOPhPh$_4$), Br$_2$BitetOH, BiphenOH, Trip$_2$BitetOH, and HIPTOH were prepared according to literature procedures. W(NAr)(CHMe$_2$Ph)(Me$_2$Pyr)$_2$, W(NAr)(CHCMe$_2$Ph)(Pyr)$_2$DME, W(NAr$^{Cl}$)(CHCMe$_3$)(Pyr)$_2$DME, Mo(NAr)(CHCMe$_2$Ph)(Me$_2$Pyr)$_2$, and Mo(NAr)(CHCMe$_2$Ph)(Pyr)$_2$ were also prepared according to published procedures.

Experimental Details on Ligand Preparation.

Figure 4A:
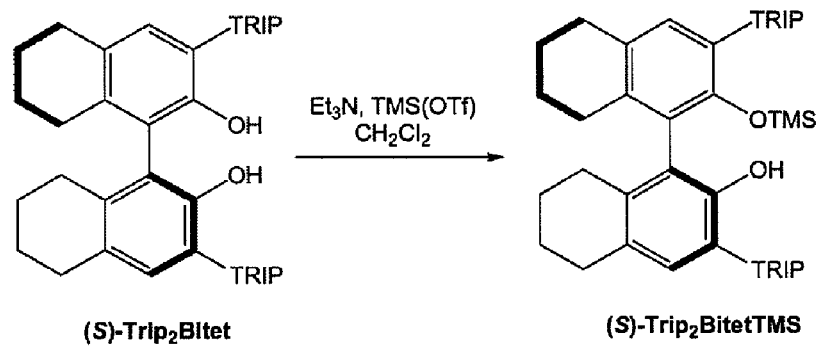
FIGS. 4A-4G illustrate the synthesis of some oxygen-containing ligands, according to some embodiments.

Trip$_2$BitetTMS (see FIG. 4A for reaction equation). A 50 mL flask was charged with a stir bar, (S)-Trip$_2$Bitet (0.782, 1.118 mmol), and methylene chloride (~15 mL). Triethyl amine (0.24 mL, 1.342 mmol, 1.2 equiv) was added to the mixture followed by trimethylsilyltriflate (0.19 mL, 1.342 mmol, 1.2 equiv). The mixture was allowed to stir for an hour, and NaHCO$_3$ (concentrated aqueous solution, ~10 mL) added. The organic layer was separated, and the aqueous layer was extracted twice with dichloromethane (~20 mL). All organic layers were combined and dried over MgSO$_4$, filtered through a bed of Celite. The filtrate was dried to give a white solid, which was dried in vacuo over night. The solid was then redissolved in methylene chloride and stirred over 4 Linde type molecular sieves in the glove box over night. The mixture was filtered through Celite and the filtrate was dried in vacuo, affording the alcohol in quantitative yield. $^1$H NMR (500 MHz, C$_6$D$_6$) δ 7.26 (d, 2, Ar—H, J$_{HH}$=8 Hz), 7.22 (d, 2, Ar—H, J$_{HH}$=8 Hz), 7.12 (s, 1, Ar—H), 6.90 (s, 1, Ar—H), 4.66 (s, 1, OH), 3.13 (m, 2), 3.02 (m, 3), 2.89 (m, 3), 2.70 (m, 4), 2.48 (m, 2), 1.68 (m, 8), 1.50 (d, 3, CHMe$_2$, J$_{HH}$=7 Hz), 1.25 (m, 33, CHMe$_2$), −0.24 (s, 9, SiMe$_3$).

Figure 4B:
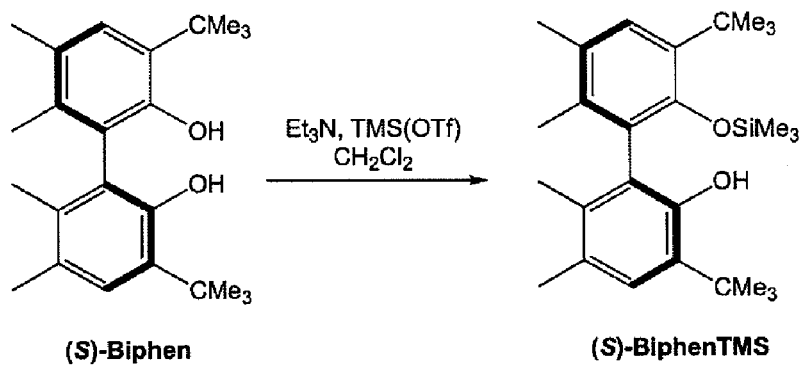

(S)-BiphenTMS (see FIG. 4B for reaction equation). Same procedure as (S)-Trip$_2$BitetTMS was carried starting with (S)-BiphenOH (1.289 g, 3.635 mmol), trimethylsilyltriflate (0.79 mL, 4.362 mmol, 1.2 equiv), and triethyl amine (0.608 g, 4.362 mmol, 1.2 equiv). The desired product was isolated in quantitative yield as a white powder. $^1$H NMR (500 MHz, C$_6$D$_6$) δ 7.24 (s, 1, Ar—H), 7.19 (s, 1, Ar—H), 4.90 (s, 1, OH), 2.17 (s, 3, Me), 2.09 (s, 3, Me), 2.88 (s, 3, Me), 1.78 (sm 3, Me), 1.60 (s, 9, t-butyl), 1.47 (s, 9, t-butyl), −0.07 (s, 9, SiMe$_3$).

Figure 4C:
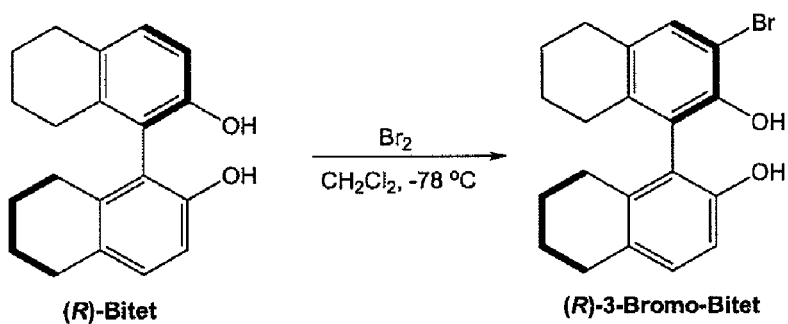
Figure 4D:
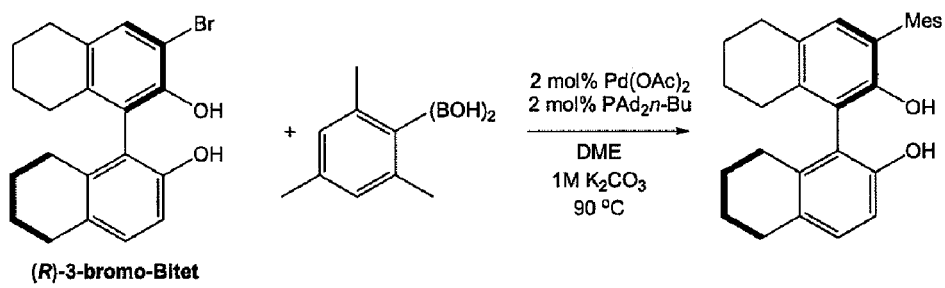

3-Bromo-Bitet (see FIG. 4C for reaction equation). Bitet (2.94 g, 10.0 mmol) was dissolved in 60 mL CH$_2$Cl$_2$ and cooled to −78° C. with dry ice and acetone bath. Bromine in 20 mL CH$_2$Cl was added through an addition funnel drop wise. After the addition was complete, the reaction mixture was allowed to stir for another 10 min and quenched with slow addition of 80 mL sat. NaHSO$_3$. The mixture was then allowed to warm to ambient temperature and stir for 1 h. The two layers were separated. The organic layer was washed with 2×30 mL sat. NaHSO$_3$, dried over MgSO$_4$, filtered and concentrated to yield the crude reaction mixture. NMR showed a mixture of starting diol:desired product:bis-bromo-bitet in a ratio of 1:4.2:3.7. Purification by silica gel chromatography (hexanes to 1:1 hexanes: CH$_2$Cl$_2$) yielded the pure desired product as a white solid (1.10 g, 30%). $^1$H NMR (500 MHz, C$_6$D$_6$): δ 7.12 (1H, s, Ar—H), 6.86 (1H, d, J=8.5 Hz, Ar—H), 6.83 (1H, d, J=8.5 Hz, Ar—H), 5.02 (1H, s, OH), 4.19 (1H, s, OH), 2.58-2.46 (2H, m, ArCH$_2$), 2.40-2.16 (4H, m, ArCH$_2$), 2.13-2.00 (2H, m, ArCH$_2$), 1.54-1.28 (8H, m, ArCH$_2$CH$_2$). 3-Mesityl-Bitet (see FIG. 4D for reaction equation). This ligand was prepared using a closely related procedure to Collazo, L. R.; Guziec, Jr., F. S. J. Org. Chem. 1993, 58, 43. Pd(OAc)$_2$ (9 mg, 0.04 mmol) and (adamantyl)$_2$-butylphosphine (18 mg, 0.05 mmol) were added in an inert atmosphere to a solution of 3-bromo-Bitet (0.75 g, 2.0 mmol) and mesityl boronic acid (0.49 g, 3.0 mmol) in 10 mL 1,2-dimethoxyethane and 10 mL 1 M K$_2$CO$_3$ solution. The mixture was heated up to 90° C. for 16 h. After cooling down the organic phase was separated, diluted with CH$_2$Cl$_2$, washed with saturated NH$_4$Cl solution as well as with H$_2$O and dried with MgSO$_4$. Then the solvent was evaporated and the solid residue was purified by column chromatography (3/1 hexanes/CH$_2$Cl$_2$) to yield 3-mesityl-Bitet as a white solid (0.71 g, 86%). $^1$H NMR (500 MHz, C$_6$D$_6$): δ 6.97 (1H, d, J=8.5 Hz, Ar—H), 6.90 (1H, d, J=8.5 Hz, Ar—H), 6.85 (1H, s, Mes-H), 6.84 (1H, s, Mes-H), 6.77 (1H, s, Ar—H), 4.69 (1H, s, OH), 4.56 (1H, s, OH), 2.66-2.26 (8H, m, ArCH$_2$), 2.17 (3H, s, Me), 2.16 (3H, s, Me), 2.09 (3H, s, Me), 1.64-1.44 (8H, m, ArCH$_2$CH$_2$).

Figure 4E:
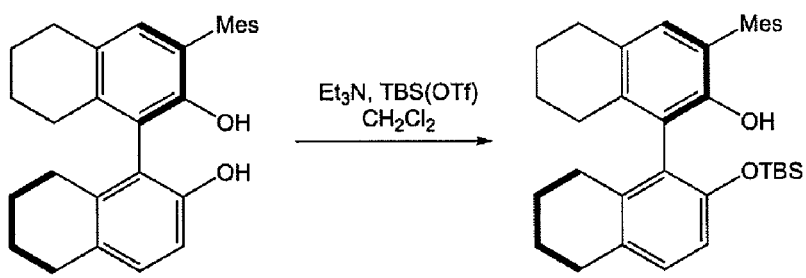

3-Mesityl-Bitet (see FIG. 4E for reaction equation, 0.2 g, 0.5 mmol) was dissolved in 2 mL CH$_2$Cl$_2$. Et$_3$N (84 mL, 0.5 mmol) was added to the reaction, followed by TBSOTf (138 mL, 0.6 mmol). The reaction mixture was allowed to stir at ambient temperature for 16 h. TLC showed complete consumption of the starting material. The reaction was quenched by the addition of 5 mL 1N HCl and extracted with 3×30 mL CH$_2$Cl$_2$. The combined organic layer was dried over MgSO$_4$, filtered and concentrated to yield a yellow solid. Purification by column chromatography (5% Et$_2$O in hexanes) yielded the desired product as an off white solid (220 mg, 84%). $^1$H NMR (500 MHz, C$_6$D$_6$): δ 6.90 (1H, d, J=8.0 Hz, Ar—H), 6.88 (1H, s, Mes-H), 6.84 (1H, s, Mes-H), 6.79 (1H, d, J=8.5 Hz, Ar—H), 6.76 (1H, s, Ar—H), 4.46 (1H, s, OH), 2.78-2.38 (8H, m, ArCH$_2$), 2.30 (3H, s, Me), 2.18 (3H, s, Me), 2.16 (3H, s, Me), 1.76-1.10 (8H, m, ArCH$_2$CH$_2$), 0.84 (9H, s, SitBu), 0.13 (3H, s, SiMe), 0.04 (3H, s, SiMe); $^{13}$C NMR (125 MHz, CDCl$_3$): δ 151.41, 147.44, 138.05, 137.54, 137.31, 136.99, 135.53, 134.44, 130.51, 130.04, 129.88, 129.04, 128.50, 128.33, 126.09, 123.88, 123.65, 116.41, 29.59, 27.38, 27.35, 25.66, 23.56, 23.50, 23.45, 23.26, 21.33, 21.04, 20.72, 18.02, −4.09, −4.22.

Figure 4F:
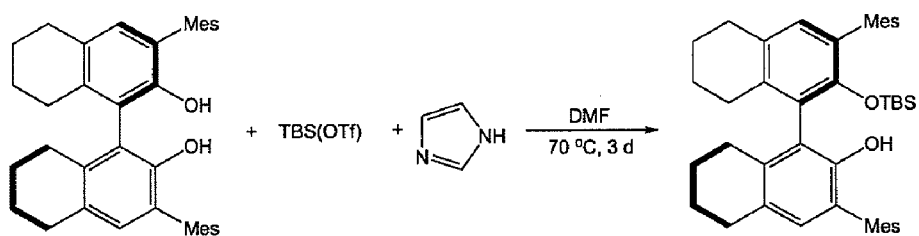

3,3'-bis-mesityl-bitet (see FIG. 4F for reaction equation) was prepared using the same Suzuki coupling as 3-mesityl-Bitet. 3,3'-bis-mesityl-Bitet (2.65 g, 5.00 mmol) was dissolved in 5 mL DMF under N$_2$. Imidazole (0.82 g, 12 mmol) was added in one portion. TBSOTf (1.4 mL, 6.0 mmol) was added to the reaction via syringe. The reaction mixture was heated to 70° C. and allowed to stir for three days. TLC showed incomplete conversion. The reaction was quenched by the addition of 10 mL 1N HCl and extracted with 3×30 mL CH$_2$Cl$_2$. The combined organic layer was washed with 4×40 mL H$_2$O (to get rid of DMF), dried over MgSO$_4$, filtered and concentrated to yield a brown solid. Crude NMR showed 80% conversion. Purification by column chromatography (20% CH$_2$Cl$_2$ in hexanes) yielded the desired product as a white solid (2.4 g, 75%). $^1$H NMR (500 MHz, CDCl$_3$): δ 6.97 (1H, s, Ar—H), 6.96 (1H, s, Ar—H), 6.89 (1H, s, Ar—H), 6.88 (1H, s, Ar—H), 6.78 (1H, s, Ar—H), 6.75 (1H, s, Ar—H), 4.54 (1H, s, OH), 2.80-2.68 (4H, m, ArCH$_2$), 2.66-2.58 (2H, m, ArCH$_2$), 2.46-2.39 (2H, m, ArCH$_2$), 2.33 (3H, s, Me), 2.30 (3H, s, Me), 2.16 (3H, s, Me), 2.12 (3H, s, Me), 2.10 (3H, s, Me), 2.07 (3H, s, Me), 1.84-1.60 (8H, m, ArCH$_2$CH$_2$), 0.46 (9H, s, SitBu), −0.47 (3H, s, SiMe), −0.56 (3H, s, SiMe). $^{13}$C NMR (125 MHz, CDCl$_3$): δ 149.1, 148.0, 137.7, 137.5, 137.1, 137.0, 136.8, 136.6, 136.57, 136.54, 136.3, 134.2, 132.7, 130.9, 130.5, 130.3, 129.6, 128.6, 128.5, 128.3, 128.1, 126.8, 124.34, 124.31, 29.5, 29.4, 27.4, 27.3, 25.7, 23.5, 23.4, 23.3, 23.1, 21.4, 21.3, 21.2, 21.1, 20.61, 20.60, 18.1, −4.49, −5.18. Anal. Calcd for C$_{44}$H$_{56}$O$_2$Si: C, 81.93; H, 8.75. Found: C, 82.21; H, 8.61.

Figure 4G:
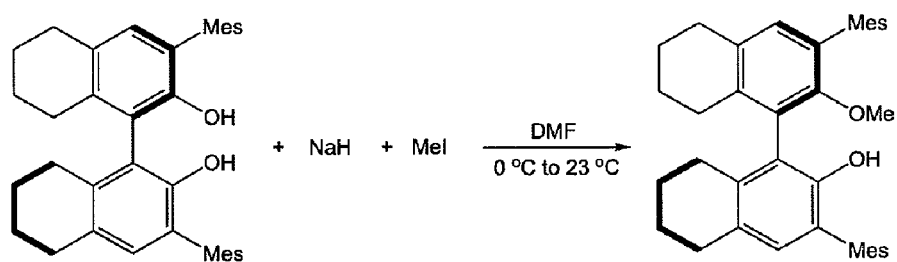

3,3-Mes$_2$bitet (see FIG. 4G for reaction equation, 0.53 g, 1.0 mmol) was dissolved in 5 mL DMF in a 100 mL round bottom flask and cooled to 0° C. using an ice bath. NaH (48 mg, 1.2 mmol) was added to the reaction in one portion. The resulting mixture was allowed to stir for half an hour. MeI (187 mL, 3.0 mmol) was added to the reaction using a syringe. The mixture was warmed to ambient temperature and allowed to stir for 36 h. The reaction was quenched by the addition of 20 mL sat. NaHCO$_3$. 20 mL of ether was added and the two layers were separated. The aqueous layer was extracted by 2×20 mL Et$_2$O. The combined organic layer was washed with 3×20 mL H$_2$O (to wash away DMF), dried over MgSO$_4$, filtered and concentrated to yield a yellowish solid. Purification was performed by silica gel chromatography (hexanes to 20% CH2Cl2 in hexanes). The desired product was collected in 0.40 g (74%). $^1$H NMR (500 MHz, CDCl$_3$): δ 6.97 (1H, s, Ar—H), 6.95 (1H, s, Ar—H), 6.93 (1H, s, Ar—H), 6.92 (1H, s, Ar—H), 6.82 (1H, s, Ar—H), 6.76 (1H, s, Ar—H), 4.40 (1H, s, OH), 3.12 (3H, s, OMe), 2.84-2.72 (4H, m, ArCH$_2$), 2.46-2.20 (4H, m, ArCH$_2$), 2.32 (6H, s, Me), 2.11 (3H, s, Me), 2.10 (3H, s, Me), 2.08 (3H, s, Me), 2.04 (3H, s, Me), 1.82-1.62 (8H, m, ArCH$_2$CH$_2$). $^{13}$C NMR (125 MHz, CDCl$_3$): d 153.6, 147.0, 137.37, 137.36, 137.2, 137.0, 136.5, 136.4, 136.0, 135.7, 135.5, 133.9, 133.3, 131.8, 131.6, 129.9, 129.3, 128.8, 128.4, 128.3, 128.1, 128.0, 124.0, 123.5, 60.0, 29.6, 29.4, 27.4, 27.0, 23.4, 23.34, 23.32, 23.1, 21.25, 21.23, 21.20, 20.7, 20.66, 20.58. Anal. Calcd for C$_{39}$H$_{44}$O$_2$: C, 85.99; H, 8.14. Found: C, 85.85; H, 8.20.

Experimental Details on Catalyst Preparations

W(NAr')(CHCMe$_2$Ph)(Me$_2$Pyr)$_2$ (1). To a 100 mL flask equipped with a stir bar was added W(NAr')(CHCMe$_2$Ph)(OTf)$_2$DME (1.64 g, 2.00 mmol), LiMe$_2$Pyr (0.404 g, 4.00 mmol), and 40 mL of toluene. The solution was allowed to stir for 16 h at which time, the solution was filtered through a bed of Celite. The filtrate was dried in vacuo to give a yellow powder. Pentane (~5 mL) was added and the mixture was filtered off. Off yellow powder was collected and dried in vacuo for 1 h, affording 0.98 g (79% yield). $^1$H NMR (500 MHz, C$_6$D$_6$) δ 10.83 (s, 1, CHCMe$_2$Ph), 7.31 (d, 2, Ar—H, $J_{HH}$=8 Hz), 7.09 (t, 2, Ar—H, $J_{HH}$=8 Hz), 6.98 (t, 1, Ar—H, $J_{HH}$=8 Hz), 6.92 (m, 3, Ar—H), 5.90 (br s, 4, Pyr-H), 2.17 (s, 6, Me), 2.11 (s, 12, Me), 1.59 (s, 6, Me).

W(NAr')(CHCMe$_2$Ph)(Pyr)$_2$DME (2). To a 100 mL flask equipped with a stir bar was added W(NAr')(CHCMe$_2$Ph)(OTf)$_2$DME (10.284 g, 12.489 mmol), LiPyr (2.280 g, 31.222 mmol, 2.5 equiv), and 50 mL of toluene. The solution was allowed to stir for 3 h at which time, the solution was filtered through a bed of Celite. The filtrate was dried in vacuo to give a yellow powder. Pentane (~10 mL) was added and the mixture was filtered off Off yellow powder was collected and dried in vacuo for 1 h, affording 4.711 g (57% yield). $^1$H NMR (500 MHz, $C_6D_6$) δ 10.78 (br s, 1, CHCMe$_2$Ph), 7.56 (d, 2, Ar—H, $J_{HH}$=8 Hz), 7.18 (t, 2, Ar—H, $J_{HH}$=8 Hz), 7.00 (t, 1, Ar—H, $J_{HH}$=8 Hz), 6.84 (br s, 4, Pyr-H), 6.80 (m, 2, Ar—H), 6.73 (m, 1, Ar—H), 6.54 (br s, 4, Pyr-H), 2.87 (s, 6, DME), 2.35 (s, 4, DME), 2.26 (s, 6, Me), 1.75 (s, 6, Me); $^{13}$C NMR (125 MHz, $C_6D_6$): δ 278.6 (CHCMe$_2$Ph), 153.6, 151.7, 137.7, 134.2, 128.4, 128.3, 127.8, 126.6, 126.3, 126.0, 109.0, 70.8, 61.8, 53.5, 32.6, 18.2. Anal. Calcd for $C_{30}H_{39}N_3O_2W$: C, 54.80; H, 5.98; N, 6.39. Found: C, 54.57; H, 5.68; N, 6.17.

W(NAr')($C_3H_6$)(Pyr)(OHIPT) (3). A 25 mL Schlenk flask was charged with a stir bar, W(NAr')(CHCMe$_2$Ph)(Pyr)$_2$DME (0.554 g, 0.842 mmol), HOHIPT (0.420 g, 0.842 mmol), and 5 mL of benzene. The reaction was stirred at 65° C. over night. The solution was then cooled to room temperature and then filtered through a glass wool. The filtrate was concentrated in vacuo. The residue was dissolved in ~5 mL of 1:1 Et$_2$O and pentane. The solution was degassed via three freeze-pump-thaw cycles, and it was exposed to 1 atm of ethylene. Off white solids precipitated out after a few minutes of stirring. The white solid was filtered off, affording 0.331 g (43% yield). $^1$H NMR (500 MHz, $C_6D_6$) δ 7.40 (br s, 2, Pyr-H), 7.28 (d, 2, Ar—H, $J_{HH}$=8 Hz), 7.21 (s, 4, Ar—H), 6.90 (t, 1, Ar—H, $J_{HH}$=8 Hz), 6.73 (d, 2, Ar—H, $J_{HH}$=8 Hz), 6.56 (t, 1, Ar—H, $J_{HH}$=8 Hz), 6.23 (s, 2, Pyr-H), 4.14 (br s, 2, WCH$_□$), 3.49 (br s, 2, WCH$_α$), 3.36 (v br s, 2, CHMe$_2$), 2.89 (sept, 2, CHMe$_2$), 2.67 (v br s, CHMe$_2$), 2.13 (s, 6, Me), 1.32 (d, 12, CHMe$_2$, $J_{HH}$=7 Hz), 1.18 (v br s, 24, CHMe$_2$), −0.85 (br s, 1, WCH$_α$), −1.23 (br s, 1, WCH$_α$); $^{13}$C NMR (125 MHz, $C_6D_6$) δ 160.22, 148.9, 148.16 (br), 138.72, 136.18, 132.47, 131.88, 131.75, 129.55 (br), 127.98, 127.00, 121.33 (br), 119.93, 110.73, 98.88 (WC$_a$), 35.16, 31.59, 26.80, 24.85, 23.32, 19.28, −4.18 (WC$_a$). Anal. Calcd for $C_{51}H_{68}N_2OW$: C, 67.39; H, 7.54; N, 3.08. Found: C, 67.31; H, 7.36; N, 3.29.

W(NAr$^{Cl}$)(CHCMe$_3$)(Pyr)(OHIPT) (4). A 20 mL flask was charged with a stir bar, W(NAr$^{Cl}$)(CHCMe$_3$)(Pyr)$_2$(DME)1/2 (0.405 g, 0.685 mmol), HOHIPT (0.342 g, 0.685 mmol), and 5 mL of benzene. The reaction was stirred at room temperature over night. The solution was then cooled to room temperature and then filtered through a bed of Celite. The filtrate was concentrated in vacuo to an oily residue. Pentane was added to the oil and yellow powder precipitated out. The yellow solid was filtered off, affording 0.381 g (56% yield). $^1$H NMR (500 MHz, $C_6D_6$) δ 9.47 (s, 1, syn-CHCMe$_3$, $J_{CH}$=119 Hz, $J_{CW}$=17 Hz), 7.24 (d, 4, Ar—H, $J_{HH}$=8 Hz), 7.11 (d, 2, Ar—H, $J_{HH}$=8 Hz), 6.87 (m, 3, Ar—H), 6.43 (s, 2, Pyr-H), 6.29 (s, 2, Pyr-H), 6.22 (t, 1, Ar—H, $J_{HH}$=8 Hz), 3.05 (sept, 2, CHMe$_2$), 2.90 (sept, 2, CHMe$_2$), 2.83 (sept, 2, CHMe$_2$), 1.35(3) (d, 6, CHMe$_2$), 1.34 (7) (d, 6, CHMe$_2$), 1.33 (d, 6, CHMe$_2$), 1.17 (d, 6, CHMe$_2$), 1.11 (d, 6, CHMe$_2$), 1.09 (d, 6, CHMe$_2$), 1.00 (s, 9, CHCMe$_3$); $^{13}$C NMR (125 MHz, $C_6D_6$) δ 269.22 (CHCMe$_3$), 158.99, 151.57, 149.08, 147.71, 135.95, 133.79, 132.30, 131.98, 131.96, 125.35, 123.29, 122.60, 121.30, 111.76, 46.53, 35.12, 33.17, 31.78, 31.66, 26.17, 25.35, 24.76, 24.75, 24.62, 23.80. Anal. Calcd for $C_{51}H_{66}Cl_2N_2OW$: C, 62.64; H, 6.80; N, 2.86. Found: C, 63.08; H, 6.76; N, 2.89.

W(NAr)(CHCMe$_2$Ph)(Pyr)(Mes$_2$Bitet). A 25 mL flask was charged with a stir bar, W(NAr)(CHCMe$_2$Ph)(Pyr)$_2$DME (0.357 g, 0.500 mmol), Mes$_2$Bitet-OH (0.323 g, 0.500 mmol), and 5 mL of benzene. The reaction was stirred at room temperature in the glovebox over night. The solution was concentrated in vacuo to yield a bright yellow powder (0.560 g, 93%). $^1$H NMR (500 MHz, $C_6D_6$) δ 10.07 ((br s, 1, CHCMe$_2$Ph), 7.30 (d, 2H, Ar—H, $J_{HH}$=4.0 Hz), 7.17 (t, 2H, Ar—H, $J_{HH}$=8.0 Hz), 7.03 (m, 2, Ar—H), 6.97 (m, 2, Ar—H), 6.87 (d, 2, Ar—H, $J_{HH}$=9.0 Hz), 6.82 (m, 2, Ar—H), 6.68 (s, 2, Ar—H), 6.57 (s, 2, pyr-H), 6.22 (s, 2, Ar—H), 3.33 (m, 2, CHCMe$_2$), 2.27(1) (s, 3, Me), 2.26(8), 2.21 (s, 3, Me), 2.19 (s, 3, Me), 2.04 (s, 3, Me), 2.01 (s, 3, Me), 1.68 (s, 3, Me), 1.46 (s, 3, Me), 1.22 (d, 6, CHMe$_2$, $J_{HH}$=8.5 Hz), 1.08 (d, 6, CHMe$_2$, $J_{HH}$=8.5 Hz), 0.66 (s, 9, t-Bu), −0.24 (s, 3, SiMe), −0.36 (s, 3, SiMe), 3.0-2.4 (m, 8), 1.8-1.3 (m, 8); $^{13}$C NMR (125 MHz, $C_6D_6$) δ 266.29 (WC$_α$), 157.19, 152.44, 151.32, 149.54, 138.12, 137.85, 137.68, 137.65, 137.55, 137.38, 137.25, 136.91, 136.88, 135.81, 133.59, 133.20, 131.64, 131.30, 131.26, 130.09, 130.06, 129.93, 129.58, 129.36, 129.25, 129.00, 128.97, 128.94, 128.72, 128.61, 126.75, 126.56, 126.31, 123.33, 111.86, 53.49, 34.82, 34.31, 32.61, 30.22, 30.06, 28.50, 28.41, 28.30, 26.48, 26.44, 25.26, 24.32, 24.10, 23.93, 23.68, 23.24, 23.12, 22.99, 22.28, 22.08, 21.46, 18.74, 14.68, −3.66, −4.06. Anal. Calcd for $C_{70}H_{80}N_2O_2SiW$: C, 69.98; H, 7.38; N, 2.33. Found: C, 69.58; H, 7.28; N, 2.13.

Mo(NAr)(CHCMe$_2$Ph)(Pyr)(OTf)DME. To an orange cloudy solution of Mo(NAr)(CHCMe$_2$Ph)(OTf)$_2$DME (1.837 g, 2.307 mmol) in 30 mL of toluene was added 0.186 g (2.538 mmol) of Li(NC$_4$H$_4$) as a solid in one portion. The reaction mixture became viscous and dark yellow. The solution was filtered through Celite after stirring it at room temperature for 2½ h, at which time the solution was less glutinous. The filtrate was dried in vacuo and to the residual was added Et$_2$O (~5 mL). The mixture was stirred and the volatiles were removed in vacuo until the mixture became a yellow solid. Light yellow powder was isolated from an Et$_2$O/pentane (1:1, ~10 mL), affording 0.885 g (54%). $^1$H NMR (500 MHz, $C_6D_6$) δ 13.91 (s, 1, syn MoCH$_α$, $J_{CH}$=119 Hz), 7.55 (d, 2, ArH), 7.23 (t, 2, ArH), 7.07 (t, 1, ArH), 6.97 (m, 3, ArH), 6.57 (br s, 2, NC$_4$H$_4$), 6.37 (t, 2, NC$_4$H$_4$), 4.22 (sept, 1, CHMe$_2$), 3.59 (br s, 1, DME-CH$_2$), 3.24 (sept, 1, CHMe$_2$), 3.08 (s, 3, DME-CH$_3$), 2.98 (s, 3, DME-CH$_3$), 2.83 (br s, 1, DME-CH$_2$), 2.32 (br d, 2, DME-CH$_2$), 1.97 (s, 3, CHCMe$_2$Ph), 1.89 (s, 3, CHCMe$_2$Ph), 1.50 (d, 3, CHMe$_2$), 1.32 (d, 3, CHMe$_2$), 1.11 (br s, 6, CHMe$_2$); $^{13}$C NMR (125 MHz, CD$_2$Cl$_2$) d 316.31 (MoC$_α$), 152.92, 152.01, 150.73, 149.44, 129.95, 129.21, 128.69, 127.01, 126.74 124.66, 124.60, 124.51, 122.14, 119.60, 117.07, 108.66, 72.42 (DME), 70.35 (DME), 63.23 (DME), 62.33 (DME), 57.89 (DME), 31.86, 30.69, 28.46, 27.61, 26.91, 25.55, 24.26, 24.17; $^{19}$F NMR (282 MHz, CD$_2$Cl$_2$) δ −78.15. Anal. Calcd for $C_{31}H_{43}F_3MoN_2O_5S$: C, 52.54; H, 6.12; N, 3.95. Found: C, 52.44; H, 6.25; N, 3.86.

Mo(NAd)(CHCMe$_3$)(Pyr)(HIPTO). Preparation of the catalyst was similar to that of Mo(NAd)(CHCMe$_2$Ph)(Pyr)(HIPTO), and Mo(NAd)(CHCMe$_3$)(Pyr)$_2$ (H$_α$ at d 13.87 and 12.88 ppm in a 1:1 ratio as broad singlets) was prepared similar to methods used to prepare Mo(NAd)(CHCMe$_2$Ph)(Pyr)$_2$. Mo(NAd)(CHCMe$_3$)(Pyr)$_2$ (0.567 g, 1.267 mmol) and HIPTOH (0.632 g, 1.267 mmol) were mixed as a solids in a 50 mL flask charged with a stirbar. Benzene (~20 mL) was added to the mixture. The dark orange solution was allowed to stir for 1 h, at which time, the mixture was filtered through a bed of Celite. The filtrate was dried in vacuo to give a dark residue. Pentane was added and the vacuo was applied to remove the volatiles; this process was repeated three more times. Yellow solids were observed. Pentane/Et$_2$O (1:1, ~5 mL) was added to the mixture. The solution was left in the fridge (−30° C.) for 1 d. Yellow needle-like crystals were isolated, affording 0.275 g (1$^{st}$ crop). The remaining filtrate was allowed to sit at −30° C. for 1 d, affording 0.632 g (2$^{nd}$ crop), and the total yield 84%. $^1$H NMR (500 MHz, $C_6D_6$) δ 11.89 (s, 1, syn MoCH$_α$, $J_{CH}$=121 Hz), 7.24 (s, 4, ArH), 7.05 (d, 2, ArH, $J_{HH}$=8 Hz), 6.87 (t, 1, ArH, $J_{HH}$=8 Hz), 6.58 (m, 2, NC$_4$H$_4$), 6.43 (m, 2, NC$_4$H$_4$), 3.06 (sept, 2, CHMe$_2$), 2.97 (sept, 4, CHMe$_2$), 1.81 (br s, 3, NAd-H), 1.78 (br s, 1, NAd- H), 1.76 (br s, 2, NAd-H), 1.72 (br s, 2, NAd-H), 1.70 (br s, 1, NAd-H), 1.36 (m, 18, CHMe$_2$ and NAd-H), 1.28 (d, 6, CHMe$_2$, J$_{HH}$=8 Hz), 1.21 (m, 15, CHMe$_2$ and CHCMe$_3$), 1.15 (d, 6, CHMe$_2$, J$_{HH}$=8 Hz), 1.13 (d, 6, CHMe$_2$, J$_{HH}$=8 Hz); $^{13}$C NMR (125 MHz, CD$_2$Cl$_2$) δ 293.44 (MoC$_a$), 159.54, 148.24, 147.66, 147.62, 135.12, 134.44, 132.14, 131.51, 121.81, 121.78, 121.61, 110.16, 44.67, 36.25, 32.67, 31.77, 31.70, 30.20, 25.40, 25.07, 24.92, 24.72, 24.66, 24.08. Anal. Calcd for C$_{55}$H$_{78}$MoN$_2$O: C, 75.14; H, 8.94; N, 3.19. Found: C, 75.24; H, 9.05; N, 3.20.

Selected characterization and synthetic procedures for numerous catalyst are given in Table 5.

Catalysts Prepared in-situ: Method 1—A weighed amount of the bipyrrolide complex and the alcohol were mixed as a solid in a Teflon seal J-Young tube. ~0.6 mL of benzene-d$_6$ was added. The reaction was monitored by $^1$H NMR. In some cases, the mixture was heated. Method 2—A weighed amount of the bispyrrolide complex and alcohol were transferred to a 5 mL vial, benzene-d$_6$ was added. The reaction progress was monitored by taking an aliquot of the mixture for $^1$H NMR. Method 3—In the case of Mo(NAr)(CHCMe$_2$Ph)(Pyr)((Trip)$_2$BitetTMS), a weighed amount Mo(NAr)(CHCMe$_2$Ph)(Pyr)(OTf)DME was mixed with Li[(Trip)$_2$BitetTMS] in a J-Young tube and benzene-d$_6$ was added. Li[(Trip)$_2$BitetTMS] was prepared by adding 1 equiv. of n-BuLi to Trip$_2$BitetTMS phenol in ether. The mixture was monitored by $^1$H NMR. After heating the mixture at 60° C. for 24 h, it was filtered through a bed of Celite to remove Li(OTf).

TABLE 5

Select characterization and synthetic procedures for numerous catalyst.

| entry | cat. | temp. (° C.) | time (h) | % conv. | alkylidene $^1$H (ppm) |
|---|---|---|---|---|---|
| 1 | W(NAr)(CHCMe$_2$Ph)(Pyr)(BiphenTMS) | 22 | 3 | >98 | 10.87, 9.93 (1:1) |
| 2 | W(NAr)(CHCMe$_2$Ph)(Me$_2$Pyr)(MesBitet) | 60 | 4 d | >95 | 9.25, 9.16 (1:4) |
| 3 | W(NAr)(CHCMe$_2$Ph)(Me$_2$Pyr)(OSi(TMS)$_3$) | 22 | 20 | >98 | 9.64 |
| 4 | W(NAr')(CHCMe$_2$Ph)(Me$_2$Pyr)(OPhPh$_4$) | 22 | 2 | >98 | 10.81 |
| 5 | W(NAr')(CHCMe$_2$Ph)(Me$_2$Pyr)(HIPTO) | 60 | 4 d | 30 | 9.62 |
| 6 | W(NAr')(CHCMe$_2$Ph)(Pyr)(HIPTO) | 22 | 15 | >98 | 9.77 |
| 7 | W(NAr')(CHCMe$_2$Ph)(Me$_2$Pyr)(Br$_2$Bitet) | 22 | 2 | >98 | 9.95, 9.84 (dr 3:1) |
| 8 | W(NAr')(CHCMe$_2$Ph)(Pyr)(MesBitet) | 22 | 15 | >98 | 9.25, 9.00 (1.5:1) |
| 9 | W(NAr')(CHCMe$_2$Ph)(Me$_2$Pyr)(MesBitet) | 60 | 2 d | >98 | 8.92, 8.79 (1:3) |
| 10 | W(NAr')(CHCMe$_2$Ph)(Pyr)(Mes$_2$BitetOMe) | 22 | 2 | >98 | 8.79 |
| 11 | W(NAr')(CHCMe$_2$Ph)(Me$_2$Pyr)(Mes$_2$Bitet) | 22 | 15 | >98 | 9.39 |
| 12 | W(NAr$^{Cl}$)(CHCMe$_3$)(Pyr)(BiphenTMS) | 22 | 3 | >98 | 10.14, 9.80, 9.43 (0.05:1:0.05) |
| 13 | W(NAr$^{Cl}$)(CHCMe$_3$)(Me$_2$Pyr)(OSi(TMS)$_3$) | 22 | 20 | >98 | 9.62 |
| 14 | W(NAr$^{Cl}$)(CHCMe$_3$)(Me$_2$Pyr)(OPhPh$_4$) | 22 | 2 | >98 | 11.04 |
| 15 | W(NAr$^{Cl}$)(CHCMe$_3$)(Me$_2$Pyr)(HIPTO) | 60 | 4 d | >98 | 9.42 |
| 16 | W(NAr$^{Cl}$)(CHCMe$_3$)(Me$_2$Pyr)(Br$_2$Bitet) | 22 | 2 | >98 | 9.80, 9.63 (1:3) |
| 17 | W(NAr$^{Cl}$)(CHCMe$_3$)(Me$_2$Pyr)(MesBitet) | 60 | 23 | >98 | 8.82, 8.64 (3:1) |
| 18 | W(NAr$^{Cl}$)(CHCMe$_3$)(Pyr)(Mes$_2$Bitet) | 22 | 16 | >98 | 9.95 |
| 19 | Mo(NAr)(CHCMe$_2$Ph)(Pyr)((Trip)$_2$BitetTMS) | 60 | 24 | >98 | 13.03, 12.92 (2:1) |
| 20 | Mo(NAd)(CHCMe$_2$Ph)(Me$_2$Pyr)(OSi(TMS)$_3$) | 22 | 20 | >98 | 9.64 |
| 21 | Mo(NAd)(CHCMe$_2$Ph))(Me$_2$Pyr)(HIPTO) | 60 | 4 d | 72 | 12.16 |
| 22 | Mo(NAd)(CHCMe$_2$Ph))(Me$_2$Pyr)(MesBitet) | 60 | 2 d | 92 | 11.27, 11.11 (1:4) |
| 23 | Mo(NAd)(CHCMe$_2$Ph)(Me$_2$Pyr)(Mes$_2$Bitet) | 90 | 2 d | 75 | 11.20 |

Screening Results: General Procedures for Screening Reactions

For 1-hexene: A weighed amount of the catalyst is transferred to a Teflon seal J-young tube, 0.6 mL of benzene-d$_6$ is delivered via syringe to dissolve the sample, then the substrate is added via syringe. Catalysts that are generated in-situ are prepared by mixing the bispyrrolide metal complex with the alcohol in 0.6 mL of benzene-d$_6$ in a Teflon seal J-young tube. Generally, after 3 h of sitting at room temperature, the substrate is then delivered, and the reaction mixture is sealed. In the cases of high reaction temperatures, the samples were heated in a closed system. The conversion and selectivity were monitored by $^1$H NMR and $^{13}$C NMR.

For 1-octene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl)dimethyl silane, and allylcyclohexane: In an N$_2$-filled glove box, a 4-mL vial was charged with the olefin substrate (0.05 mmol) and 150 μL of C$_6$H$_6$. A solution of different catalyst in C$_6$H$_6$ (50 μL, 4 mol %) was added to the vial in one portion. The mixture was allowed to stir at 22° C. for a certain time and an aliquot of the reaction was then transferred to a NMR tube and taken outside the box. The aliquot was thus quenched by exposure to air, diluted in CDCl$_3$. The conversion and selectivity of the reactions were monitored by $^1$H NMR.

TABLE 6

Selected results for the homo-metathesis of 1-hexene, $CH_2=CH(CH_2)_3CH_3$ ($S_1$)

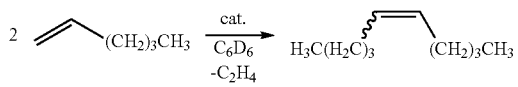

| entry | catalyst | mol % | sub. conc. (M) | time. (h) | temp. (°C.) | % conv. | % cis |
|---|---|---|---|---|---|---|---|
| 1 | W(NAr)(C$_3$H$_6$)(Me$_2$Pyr)(Br$_2$Bitet) | 5 | 0.31 | 0.5 | 22 | 63 | 33 |
|   |   |   |   | 24 | 60 | 85 | 20 |
| 2 | W(NAr')(CHCMe$_2$Ph)(Me$_2$Pyr)(Br$_2$Bitet)[†] | 5 | 0.27 | 0.5 | 22 | 49 | 77 |
| 3 | W(NAr$^{Cl}$)(CHCMe$_3$)(Me$_2$Pyr)(Br$_2$Bitet)[†] | 5 | 0.28 | 1 | 22 | 60 | 15 |
| 4 | W(NAr)(C$_3$H$_6$)(Me$_2$Pyr)(OPhPh$_4$) | 5 | 0.37 | 0.5 | 22 | 59 | 33 |
|   |   |   |   | 24 | 60 | 75 | 33 |
| 5 | W(NAr')(CHCMe$_2$Ph)(Me$_2$Pyr)(OPhPh$_4$)[†] | 5 | 0.27 | 1 | 22 | 65 | 25 |
| 6 | W(NAr$^{Cl}$)(CHCMe$_3$)(Me$_2$Pyr)(OPhPh$_4$)[†] | 5 | 0.28 | 1.5 | 22 | 66 | 22 |
| 8 | W(NAr)(CHCMe$_2$Ph)(Pyr)(BiphenTMS)[†] | 2 | 0.86 | 0.5 | 22 | 46 | 42 |
|   |   |   |   | 20 | 22 | 59 | 38 |
| 8 | W(NAr$^{Cl}$)(CHCMe$_3$)(Pyr)(BiphenTMS)[†] | 2 | 0.86 | 0.5 | 22 | 85 | 68 |
|   |   |   |   | 16 | 22 | 79 | 21 |
| 9 | W(NAr)(C$_3$H$_6$)(Pyr)(OHIPT) | 4 | 0.66 | 3 d | 22 | 35 | 95 |
|   |   |   |   | 24 | 60 | 58 | 95 |
|   |   |   |   | 24 | 90 | 79 | 95 |
| 10 | W(NAr$^{Cl}$)(CHMe$_3$)(Pyr)(OHIPT) | 4 | 0.62 | 1 | 22 | 41 | 85 |
|   |   |   |   | 24 | 70 | 97 | 71 |
| 11 | Mo(NAr)(CHCMe$_2$Ph)(Pyr)(OHIPT)[†] | 4 | 0.22 | 7 | 22 | 68 | 38 |

[†]Catalyst was generated in-situ.

TABLE 7

Selected results for the homo-metathesis 1-octene, $CH_2=CH(CH_2)_5CH_3$ ($S_2$).

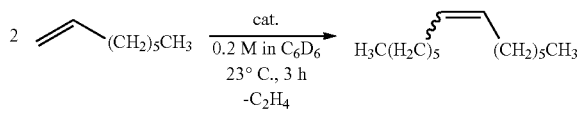

| entry | cat. | mol % | time (h) | % conv. | % cis |
|---|---|---|---|---|---|
| 1 | W(NAr)(CHCMe$_2$Ph)(Me$_2$Pyr)(Br$_2$Bitet) | 5 | 7 | 79 | 21 |
| 2 | W(NAr)(CHCMe$_2$Ph)(Me$_2$Pyr)(OPhPh$_4$) | 5 | 3 | 81 | 21 |
| 3 | W(NAr)(CHCMe$_2$Ph)(Me$_2$Pyr)(MesBitet)[†] | 5 | 3.5 | 65 | 83 |
|   |   |   | 24 | 90 | 66 |
| 4 | W(NAr$^{Cl}$)(CHCMe$_3$)(Me$_2$Pyr)(OSi(TMS)$_3$)[†] | 5 | 3 | 65 | 63 |
| 5 | W(NAr$^{Cl}$)(CHCMe$_3$)(Me$_2$Pyr)(HIPTO)[†] | 5 | 3 | 65 | 21 |
| 6 | W(NAr$^{Cl}$)(CHCMe$_3$)(Me$_2$Pyr)(MesBitet)[†] | 5 | 0.5 | 55 | 50 |
| 7 | W(NAr')(CHCMe$_2$Ph)(Me$_2$Pyr)(OSi(TMS)$_3$)[†] | 5 | 3 | 74 | 20 |
| 8 | W(NAr')(CHCMe$_2$Ph)(Me$_2$Pyr)(HIPTO)[†] | 5 | 3 | 68 | 54 |
| 9 | W(NAr')(CHCMe$_2$Ph)(Me$_2$Pyr)(MesBitet)[†] | 5 | 0.5 | 16 | 90 |
|   |   |   | 2.5 | 55 | 83 |
|   |   |   | 18 | 64 | 61 |
| 10 | Mo(NAd)(CHCMe$_2$Ph)(Me$_2$Pyr)(OSi(TMS)$_3$)[†] | 5 | 3 | 69 | 19 |
| 11 | Mo(NAd)(CHCMe$_2$Ph))(Me$_2$Pyr)(HIPTO)[†] | 5 | 3 | 43 | 68 |
| 12 | Mo(NAd)(CHCMe$_2$Ph))(Me$_2$Pyr)(MesBitet)[†] | 5 | 3 | 61 | 79 |
| 13 | Mo(NAr)(CHCMe$_2$Ph)(Pyr)((Trip)$_2$Bitet(TMS))[†] | 4 | 2 | 78 | 28 |
| 14 | W(NAr)(C$_3$H$_6$)(Pyr)(HIPTO) | 4 | 3 | 33 | 95 |
|   |   |   | 26 | 88 | 88 |
| 15 | W(NAr)(CHCMe$_2$Ph)(Pyr)(Mes$_2$Bitet)[†] | 4 | 0.5 | 38 | 93 |
|   |   |   | 2 | 72 | 88 |
| 16 | W(NAr$^{Cl}$)(CHCMe$_3$)(Pyr)(HIPTO) | 4 | 3 | 71 | 82 |
| 17 | W(NAr')(CHCMe$_2$Ph)(Pyr)(HIPTO)[†] | 4 | 2 | 50 | 86 |
| 18 | W(NAr')(CHCMe$_2$Ph)(Pyr)(MesBitet)[†] | 4 | 2 | 83 | 50 |
| 19 | W(NAr')(CHCMe$_2$Ph)(Pyr)(Mes$_2$Bitet)[†] | 4 | 2 | 64 | 93 |

[†]Catalyst was generated in-situ.

TABLE 8

Selected results for the homo-metathesis allylbenzene, $CH_2=CHCH_2Ph$ ($S_3$).

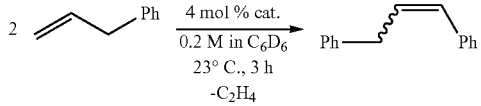

| entry | cat. | % conv. | % cis |
|---|---|---|---|
| 1 | W(NAr)(C$_3$H$_6$)(Pyr)(HIPTO) | 40 | 91 |
| 2 | W(NAr)(CHCMe$_2$Ph)(Pyr)(Mes$_2$Bitet)† | 30 | 83 |
| 3 | W(NAr')(CHCMe$_2$Ph)(Pyr)(HIPTO)† | 33 | 91 |
| 4 | W(NAr')(CHCMe$_2$Ph)(Pyr)(Mes$_2$Bitet)† | 33 | 81 |
| 5 | W(NAr$^{Cl}$)(CHCMe$_3$)(Pyr)(HIPTO) | 63 | 84 |
| 6 | W(NAr$^{Cl}$)(CHCMe$_3$)(Pyr)(Mes$_2$Bitet)† | 62 | 93 |

TABLE 8-continued

Selected results for the homo-metathesis allylbenzene, $CH_2=CHCH_2Ph$ ($S_3$).

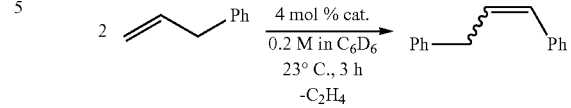

| entry | cat. | % conv. | % cis |
|---|---|---|---|
| 7 | Mo(NAd)(CHCMe$_2$Ph)(Me$_2$Pyr)(Br$_2$Bitet)† | 78 | 44 |
| 8 | Mo(NAd)(CHCMe$_2$Ph)(Me$_2$Pyr)(Mes$_2$Bitet)† | 16 | 59 |
| 9 | Mo(NAd)(CHCMe$_3$)(Pyr)(HIPTO), 2 mol %, J-Young tube | 27 (23 h) | 90 |

†Catalyst was generated in-situ.

TABLE 9

Selected results for the homo-metathesis allyltrimethylsilane, $CH_2=CHCH_2SiMe_3$ ($S_4$).

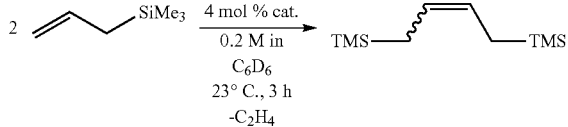

| entry | cat. | % conv. | % cis |
|---|---|---|---|
| 1 | W(NAr)(C$_3$H$_6$)(Pyr)(HIPTO) | 30 | 73 |
| 2 | W(NAr)(CHCMe$_2$Ph)(Pyr)(Mes$_2$Bitet)† | 32 | 54 |
| 3 | W(NAr')(CHCMe$_2$Ph)(Pyr)(HIPTO)† | 33 | 82 |
| 4 | W(NAr')(CHCMe$_2$Ph)(Pyr)(Mes$_2$Bitet)† | 30 | 69 |
| 5 | W(NAr$^{Cl}$)(CHCMe$_3$)(Pyr)(HIPTO) | 48 | 87 |
|   |   | 58 | 80 |
| 6 | W(NAr$^{Cl}$)(CHCMe$_3$)(Pyr)(Mes$_2$Bitet)† | 26 | 86 |
|   |   | 52 | 84 |
| 7 | Mo(NAd)(CHCMe$_2$Ph)(Me$_2$Pyr)(Br$_2$Bitet)† | 33 | >98 |
|   |   | 68 | 83 |
| 8 | Mo(NAd)(CHCMe$_2$Ph)(Me$_2$Pyr)(Mes$_2$Bitet)† | 18 | 52 |
| 9 | Mo(NAd)(CHCMe$_3$)(Pyr)(HIPTO), 1 mol % | <2 (24 h) | — |

†Catalyst was generated in-situ.

TABLE 10

Selected results for the homo-metathesis methyl-9-decenoate, $CH_2=CH(CH)_7CO_2Me$ ($S_6$).

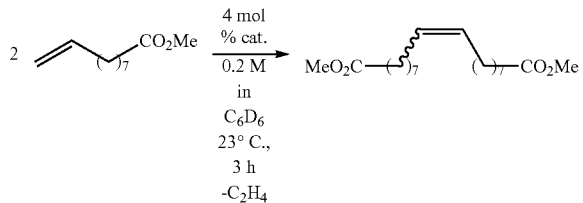

| entry | cat. | % conv. | % cis |
|---|---|---|---|
| 1 | W(NAr)(C$_3$H$_6$)(Pyr)(HIPTO) | 26 | 77 |
| 2 | W(NAr)(CHCMe$_2$Ph)(Pyr)(Mes$_2$Bitet)† | 40 | 69 |
| 3 | W(NAr')(CHCMe$_2$Ph)(Pyr)(HIPTO)† | 33 | 90 |
| 4 | W(NAr')(CHCMe$_2$Ph)(Pyr)(Mes$_2$Bitet)† | 39 | 88 |
|   |   | 60 | 75 |
| 5 | W(NAr$^{Cl}$)(CHCMe$_3$)(Pyr)(HIPTO) | 65 | 79 |
| 6 | W(NAr$^{Cl}$)(CHCMe$_3$)(Pyr)(Mes$_2$Bitet)† | 73 | 62 |
| 7 | Mo(NAd)(CHCMe$_2$Ph)(Me$_2$Pyr)(Br$_2$Bitet)† | 75 | 50 |
| 8 | Mo(NAd)(CHCMe$_2$Ph)(Me$_2$Pyr)(Mes$_2$Bitet)† | 13 | 70 |

†Catalyst was generated in-situ.

TABLE 11

Selected results for the homo-metathesis allylboronic acid pinacol ester, CH$_2$=CHCH$_2$(Bpin) (S$_7$).

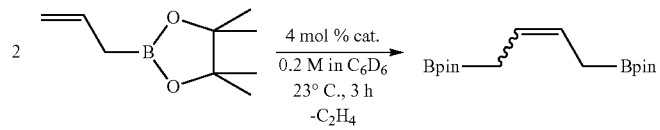

| entry | cat. | % conv. | % cis |
|---|---|---|---|
| 1 | W(NAr)(C$_3$H$_6$)(Pyr)(HIPTO) | 30 | 94 |
| 2 | W(NAr)(CHCMe$_2$Ph)(Pyr)(Mes$_2$Bitet)[†] | 50 | 81 |
| 3 | W(NAr')(CHCMe$_2$Ph)(Pyr)(HIPTO)[†] | 31 | 94 |
| 4 | W(NAr')(CHCMe$_2$Ph)(Pyr)(Mes$_2$Bitet)[†] | 34 | 92 |
| 5 | W(NAr$^{Cl}$)(CHCMe$_3$)(Pyr)(HIPTO) | 66 | 82 |
| 6 | W(NAr$^{Cl}$)(CHCMe$_3$)(Pyr)(Mes$_2$Bitet)[†] | 69 | 80 |
| 7 | Mo(NAd)(CHCMe$_2$Ph)(Me$_2$Pyr)(Br$_2$Bitet)[†] | 32 | >98 |
|   |   | 40 | 77 |
| 8 | Mo(NAd)(CHCMe$_2$Ph)(Me$_2$Pyr)(Mes$_2$Bitet)[†] | 17 | 62 |

Reactions carried out in a Teflon sealed J-Young tube.

| entry | cat. | sub. conc. (M) | time (h) | temp (° C.) | % conv. | % cis |
|---|---|---|---|---|---|---|
| 8 | W(NAr)(C$_3$H$_6$)(Pyr)(HIPTO) | 0.43 | 0.25 | 22 | 15 | 99 |
|   |   |   | 20 | 70 | 76 | 82 |
| 9 | W(NAr$^{Cl}$)(CHCMe$_3$)(Pyr)(HIPTO) | 0.54 | 0.25 | 22 | 70 | 96 |
|   |   |   | 1.5 | 22 | 70 | 96 |
|   |   |   | 20 | 70 | 87 | 84 |

[†]Catalyst was generated in-situ.

TABLE 12

Selected results for the homo-metathesis allylbenzylether, CH$_2$=CHCH$_2$OBn (S$_8$).

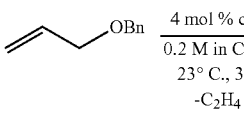

| entry | cat. | % conv. | % cis |
|---|---|---|---|
| 1 | W(NAr)(C$_3$H$_6$)(Pyr)(HIPTO) | 10 | >98 |
| 2 | W(NAr)(CHCMe$_2$Ph)(Pyr)(Mes$_2$Bitet)[†] | 24 | >98 |
| 3 | W(NAr')(CHCMe$_2$Ph)(Pyr)(HIPTO)[†] | <2 | — |
| 4 | W(NAr')(CHCMe$_2$Ph)(Pyr)(Mes$_2$Bitet)[†] | 13 | >98 |
| 5 | W(NAr$^{Cl}$)(CHCMe$_3$)(Pyr)(HIPTO) | <2 | — |
| 6 | W(NAr$^{Cl}$)(CHCMe$_3$)(Pyr)(Mes$_2$Bitet)[†] | 24 | >98 |
| 7 | Mo(NAd)(CHCMe$_2$Ph)(Me$_2$Pyr)(Br$_2$Bitet)[†] | >90 | 14 |
| 8 | Mo(NAd)(CHCMe$_2$Ph)(Me$_2$Pyr)(Mes$_2$Bitet)[†] | <2 | — |

[†]Catalyst was generated in-situ.

TABLE 13

Selected results for the homo-metathesis N-allyl-4-methylbenzene-sulfonamide, CH$_2$=CHCH$_2$NHTs (S$_9$).

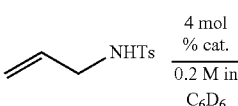

| entry | cat. | % conv. | % cis |
|---|---|---|---|
| 1 | W(NAr)(C$_3$H$_6$)(Pyr)(HIPTO) | 16 | >98 |
| 2 | W(NAr)(CHCMe$_2$Ph)(Pyr)(Mes$_2$Bitet)[†] | 10 | >98 |
| 3 | W(NAr')(CHCMe$_2$Ph)(Pyr)(HIPTO)[†] | 21 | >98 |

TABLE 13-continued

Selected results for the homo-metathesis N-allyl-4-methylbenzene-sulfonamide, CH$_2$=CHCH$_2$NHTs (S$_9$).

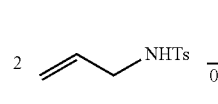

| entry | cat. | % conv. | % cis |
|---|---|---|---|
| 4 | W(NAr')(CHCMe$_2$Ph)(Pyr)(Mes$_2$Bitet)[†] | 19 | >98 |
| 5 | W(NAr$^{Cl}$)(CHCMe$_3$)(Pyr)(HIPTO) | 22 | >98 |
| 6 | W(NAr$^{Cl}$)(CHCMe$_3$)(Pyr)(Mes$_2$Bitet)[†] | 52 | >98 |
| 7 | Mo(NAd)(CHCMe$_2$Ph)(Me$_2$Pyr)(Br$_2$Bitet)[†] | 23 | 75 |
| 8 | Mo(NAd)(CHCMe$_2$Ph)(Me$_2$Pyr)(Mes$_2$Bitet)[†] | <2 | — |

[†]Catalyst was generated in-situ.

TABLE 14

Selected results for the homo-metathesis N-allylaniline, CH=CHCH$_2$(NHPh), (S$_{10}$).

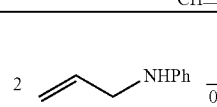

| entry | cat. | % conv. | % cis |
|---|---|---|---|
| 1 | W(NAr')(CHCMe$_2$Ph)(Pyr)(Mes$_2$Bitet)[†] | <5 | >98 |
| 2 | W(NAr')(CHCMe$_2$Ph)(Pyr)(HIPTO)[†] | <5 | 67 |

TABLE 14-continued

| | | | |
|---|---|---|---|
| 3 | W(NAr')(CHCMe$_2$Ph)(Pyr)(Mes$_2$Bitet)[†] | 6 | >98 |
| 4 | W(NAr')(CHCMe$_2$Ph)(Pyr)(Mes$_2$BitetOMe)[†] | 12 | >98 |
| 5 | W(NAr$^{Cl}$)(CHCMe$_3$)(Pyr)(HIPTO) | 20 | >98 |
| 6 | Mo(NAr)(CHCMe$_2$Ph)(Pyr)(Mes$_2$Bitet)[†] | 65 | 94 |

[†]Catalyst was generated in-situ.

TABLE 15

Selected results for the homo-metathesis allyloxy(tert-butyl)dimethyl-silane, CH=CHCH$_2$(OTBs) (S$_{11}$).

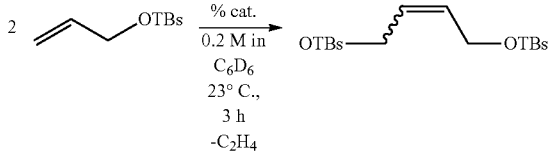

| entry | cat. | % conv. | % cis |
|---|---|---|---|
| 1 | W(NAr)(C$_3$H$_6$)(Pyr)(HIPTO) | <2 | — |
| 2 | W(NAr)(CHCMe$_2$Ph)(Pyr)(Mes$_2$Bitet)[†] | <2 | — |
| 3 | W(NAr')(CHCMe$_2$Ph)(Pyr)(HIPTO)[†] | <2 | — |
| 4 | W(NAr')(CHCMe$_2$Ph)(Pyr)(Mes$_2$Bitet)[†] | <2 | — |
| 5 | W(NAr$^{Cl}$)(CHCMe$_3$)(Pyr)(HIPTO) | 30 | >98 |
| 6 | W(NAr$^{Cl}$)(CHCMe$_3$)(Pyr)(Mes$_2$Bitet)[†] | 20 | >98 |

TABLE 15-continued

Selected results for the homo-metathesis allyloxy(tert-butyl)dimethyl-silane, CH=CHCH$_2$(OTBs) (S$_{11}$).

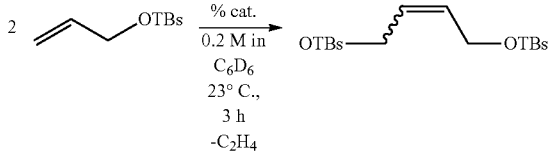

| entry | cat. | % conv. | % cis |
|---|---|---|---|
| 7 | Mo(NAd)(CHCMe$_2$Ph)(Me$_2$Pyr)(Br$_2$Bitet)[†] | 12 | >98 |
| 8 | Mo(NAd)(CHCMe$_2$Ph)(Me$_2$Pyr)(Mes$_2$Bitet)[†] | 12 | >98 |

[†]Catalyst was generated in-situ.

TABLE 16

Selected results for the homo-metathesis allylcyclohexane, CH$_2$=CHCH$_2$Cy (S$_{12}$).

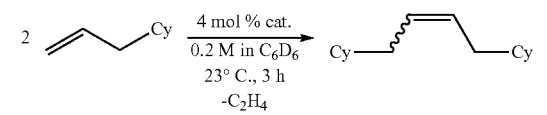

| entry | cat. | % conv. | % cis |
|---|---|---|---|
| 1 | W(NAr)(C$_3$H$_6$)(Pyr)(HIPTO) | 16 | 63 |
| 2 | W(NAr)(CHCMe$_2$Ph)(Pyr)(Mes$_2$Bitet)[†] | 50 | 50 |
| 3 | W(NAr')(CHCMe$_2$Ph)(Pyr)(HIPTO)[†] | 31 | 75 |
| 4 | W(NAr')(CHCMe$_2$Ph)(Pyr)(Mes$_2$Bitet)[†] | 20 | 63 |
| 5 | W(NAr$^{Cl}$)(CHCMe$_3$)(Pyr)(HIPTO) | 57 | 72 |
| 6 | W(NAr$^{Cl}$)(CHCMe$_3$)(Pyr)(Mes$_2$Bitet)[†] | 50 | 79 |
| 7 | Mo(NAd)(CHCMe$_2$Ph)(Me$_2$Pyr)(Br$_2$Bitet)[†] | 35 | 84 |
| 8 | Mo(NAd)(CHCMe$_2$Ph)(Me$_2$Pyr)(Mes$_2$Bitet)[†] | 14 | 50 |

[†]Catalyst was generated in-situ.

TABLE 17

Comparison of Mo and W Catalysts.

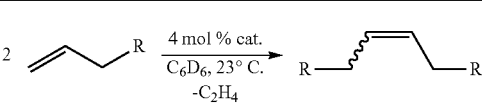

| entry | substrate | cat. | time (h) | % conv. | % cis |
|---|---|---|---|---|---|
| 1 | S$_2$ | Mo(NAr)(Pyr)(CHCMe$_2$Ph)(HIPTO)[†] | 0.33 | 80 | 40 |
| 2 | | W(NAr)(Pyr)(C$_3$H$_6$)(HIPTO) | 26 | 88 | 88 |
| 3 | | Mo(NAr)(Pyr)(CHCMe$_2$Ph)(Mes$_2$Bitet)[†] | 0.25 | 58 | 70 |
| 4 | | W(NAr)(Pyr)(CHCMe$_2$Ph)(Mes$_2$Bitet)[†] | 2 | 72 | 88 |
| 5 | S$_3$ | Mo(NAr)(Pyr)(CHCMe$_2$Ph)(Mes$_2$Bitet)[†] | 0.33 | 24 | 62 |
| 6 | | W(NAr)(Pyr)(CHCMe$_2$Ph)(Mes$_2$Bitet)[†] | 14 | 30 | 83 |
| 7 | S$_4$ | Mo(NAr)(Pyr)(CHCMe$_2$Ph)(Mes$_2$Bitet)[†] | 0.33 | 12 | 50 |
| 6 | | W(NAr)(Pyr)(CHCMe$_2$Ph)(Mes$_2$Bitet)[†] | 2 | 30 | 84 |
| 8 | S$_{11}$ | Mo(NAr)(Pyr)(CHCMe$_2$Ph)(Mes$_2$Bitet)[†] | 0.33 | 13 | 61 |
| 9 | | W(NAr)(Pyr)(CHCMe$_2$Ph)(Mes$_2$Bitet)[†] | 14 | <5 | — |
| 10 | S$_6$ | Mo(NAr)(Pyr)(CHCMe$_2$Ph)(Mes$_2$Bitet)[†] | 0.33 | 85 | 26 |
| 11 | | W(NAr)(Pyr)(CHCMe$_2$Ph)(Mes$_2$Bitet)[†] | 14 | 40 | 69 |

[†]Catalyst was generated in-situ.

TABLE 18

Screening Results of Catalysts Derived from Mes$_2$BitetOMe Supported by NAr and NAr'

2 ⇌ R $\xrightarrow[\text{C}_6\text{D}_6, 23°\text{C.}]{\text{4 mol \% cat.}}$ R⁀R
$-\text{C}_2\text{H}_4$

| entry | substrate | time (h) | % conv. | % cis |
|---|---|---|---|---|
| Cat: W(NAr)(CHCMe$_2$Ph)(Pyr)(Mes$_2$BitetOMe)† | | | | |
| 1 | S$_2$ | 1.5 | 62 | 66 |
| 2 | S$_3$ | 1.5 | 54 | 84 |
| 3 | | 23 | 66 | 83 |
| 4 | S$_{12}$ | 1.5 | 44 | 74 |
| 5 | | 23 | 40 | 74 |
| 6 | S$_4$ | 1.5 | 70 | 74 |
| 7 | | 23 | 76 | 60 |
| 8 | S$_5$ | 1.5 | 76 | 90 |
| 9 | | 23 | 66 | 75 |
| 10 | S$_{11}$ | 1.5 | <5 | — |
| 11 | | 23 | <5 | — |
| 12 | S$_8$ | 1.5 | 14 | >98 |
| 13 | | 23 | 15 | >98 |
| 14 | S$_9$ | 1.5 | 32 | >98 |
| 15 | | 23 | 44 | 87 |
| Cat: W(NAr')(CHCMe$_2$Ph)(Pyr)(Mes$_2$BitetOMe)† | | | | |
| 16 | S$_2$ | 1.5 | 73 | 73 |
| 17 | S$_3$ | 1.5 | 73 | 92 |
| 18 | | 23 | — | 94 |
| 19 | S$_{12}$ | 1.5 | 70 | 83 |
| 20 | | 23 | 60 | 85 |
| 21 | S$_4$ | 1.5 | 84 | 81 |
| 22 | | 23 | — | 87 |
| 23 | S$_5$ | 1.5 | 69 | 92 |
| 24 | | 23 | 75 | 83 |
| 25 | S$_{11}$ | 1.5 | 5 | >98 |
| 26 | | 23 | 8 | >98 |
| 27 | S$_8$ | 1.5 | 8 | >98 |
| 28 | | 23 | 8 | >98 |
| 29 | S$_9$ | 1.5 | 25 | >98 |
| 30 | | 23 | 53 | >98 |

†Catalyst was generated in-situ.

General Experimental Comments on Olefin Metathesis Reactions at Elevated Temperatures: A weighed sample of the catalysts was dissolved in ~1 mL of benzene in a 25 mL Schlenk flask charged with a stir bar. Substrate (liquid) was then delivered via a syringe, and in the case of solid substrate, it was weighed out and delivered as a solid to the catalysts solution in one portion. The sample was then refluxed under nitrogen at the temperature noted. The homo-coupled product was isolated as described below, and the percentage of Z-content depends on the catalyst. Only the data for the Z-product are reported since the E-analog is a small percentage of the mixture. The % Z in each isolated case was confirmed by $^{13}$C NMR.

TABLE 19

Reactions carried out at elevated temperatures.

2 ⇌ R $\xrightarrow[\text{C}_6\text{D}_6]{\text{cat.}}$ R⁀R
$-\text{C}_2\text{H}_4$

| entry | sub. | mol % | sub. conc. (M) | time (h) | temp. (°C.) | % conv. | % cis | % yield |
|---|---|---|---|---|---|---|---|---|
| catalyst: W(NAr)(C$_3$H$_6$)(Pyr)(HIPTO) | | | | | | | | |
| 1 | S$_1$ | 0.2 | 6.7 | 6 | 80 | 26 | >98 | — |
| | | | | 3 d | 80 | 50 | 82 | 24 |
| catalyst: W(NAr)(C$_3$H$_6$)(Pyr)(HIPTO) (continued) | | | | | | | | |
| 2 | S$_1$ | 0.4 | 5.7 | 18 | 80 | 62 | 98 | — |
| | | | | 2d | 80 | 72 | 95 | 58 |
| 3 | S$_2$ | 0.4 | 4.7 | 24 | 120 | 94 | 86 | 78 |
| 4 | S$_2$ | 0.2 | 5.1 | 24 | 120 | 56 | 82 | 46 |
| 5 | S$_3$ | 1 | 6.0 | 13 | 22 | 22 | 95 | — |
| | | | | 9 | 80 | 53 | 95 | — |
| | | | | 24 | 110 | 87 | 92 | 54 |
| 6 | S$_3$ | 0.2 | 6.0 | 1.5 | 110 | 28 | 97 | — |
| | | | | 1.5 | 120 | 60 | 96 | — |
| | | | | 4 | 120 | 63 | 93 | 56 |
| 7 | S$_7$ | 0.2 | 4.1 | 1 | 100 | 46 | 91 | — |
| | | | | 24 | 100 | 61 | 90 | — |
| 8 | S$_9$ | 4 | 1.2 | 18 | 100 | 95 | 91 | 90 |
| 9 | S$_8$ | 4 | 1.6 | 15 | 100 | <5 | >98 | — |
| 10 | S$_5$ | 1 | neat | 21 | 22 | 27 | >98 | — |
| | | | | 21 | 70 | 50 | >98 | — |
| catalyst: W(NAr$^{Cl}$)(CHCMe$_3$)(Pyr)(HIPTO) | | | | | | | | |
| 11 | S$_1$ | 0.5 | 6.7 | 4 | 80 | 88 | 86 | — |
| | | | | 24 | 80 | >98 | 80 | 88 |

TABLE 19-continued

Reactions carried out at elevated temperatures.

$$2 \diagup\!\!\!\diagup R \xrightarrow[-C_2H_4]{cat.\ C_6H_6} R\diagup\!\!\!\sim\!\!\!\diagup R$$

| entry | sub. | mol % | sub. conc. (M) | time (h) | temp. (° C.) | % conv. | % cis | % yield |
|---|---|---|---|---|---|---|---|---|
| 12 | S₁ | 0.1 | 7.2 | 5 | 80 | 74 | 96 | — |
|  |  |  |  | 20 |  | 89 | 95 | 26 |
| 13 | S₂ | 0.2 | 5.5 | 1 | 120 | 85 | 80 | — |
|  |  |  |  | 3 | 120 | >98 | 77 | 77 |
| 14 | S₃ | 0.2 | 5.8 | 2 | 100 | 65 | 88 | — |
|  |  |  |  | 24 | 100 | 94 | 88 | 65 |
| 15 | S₇ | 0.2 | 1.7 | 18 | 100 | 74 | 94 | — |
| 16 | S₉ | 1 | 1.2 | 24 | 80 | 21 | >98 | — |
| 17 | S₉ | 4 | 0.6 | 24 | 90 | 50 | 94 | 36 |
| 18 | S₈ | 0.2 | 3.2 | 18 | 100 | <2 | — | — |
| catalyst: W(NAr')(C₃H₆)(Pyr)(HIPTO) | | | | | | | | |
| 19 | S₄ | 0.2 | 4.7 | 18 | 90 | 28 | 26 | 86 |
| 20 | S₅ | 2 | 2.0 | 23 | 100 | >97 | 95 | — |
| 21 | S₆ | 1 | 1.0 | 16 | 100 | 97 | 87 | 80 |
| catalyst: W(NAr')(CHCMe₂Ph)(Pyr)(Mes₂Bitet) | | | | | | | | |
| 22 | S₂ | 0.2 | 5.0 | 16 | 90 | 56 | 86 | — |
| 23 | S₈ | 4 | 2.0 | 24 | 100 | 46 | >98 | 42 |
| catalyst: W(NAr')(CHCMe₂Ph)(Pyr)(Mes₂BitetOMe)‡ | | | | | | | | |
| 24 | S₉ | 2 | 0.5 | 22 | 80 | 58 | 90 | 55 |

‡Catalysts prepared in situ.

Experimental Details on Reactions Carried Out Under Vacuum: A weighed amount of the catalyst was transferred to vial. In the cases where the catalysts were generated in-situ, the solvent was removed prior to adding the substrate. Under partial vacuum, the substrate was delivered via syringe in portion. The reaction was allowed to sit in vacuo, and was monitored by $^1$H NMR.

TABLE 20

The Effect of a Vacuum on Z Content.$^a$

| entry | Pressure (Torr) | sub. | mol % | time (h) | % conv. | % cis |
|---|---|---|---|---|---|---|
| catalyst: W(NAr')(CHCMe₂Ph)(Pyr)(Mes₂BitetOMe) | | | | | | |
| 1 | high vac (~0.5) | S₅ | 1 | 0.17 | 25 | >98 |
|  |  |  |  | 1.5 | 88 | >98 |
|  |  |  |  | 13 | 98$^b$ | >98 (86% isolated) |
| 2 | 10 | S₅ | 1 |  |  |  |
| 3 | 760 N₂ | S₅ | 2 | 1.5 | 84 | 97 |
|  |  |  |  | 15 | 86 | 88 |
| catalyst: Mo(NAr)(CHCMe₂Ph)(Pyr)(Mes₂BitetOMe)$^c$ | | | | | | |
| 4 | high vac (~0.5) | S₅ | 0.5 | 2 | 31 | 66 |
| 5 | 760 N₂ | S₅ | 0.5 | 2 | 10 | 74 |
| 6 | high vac (~0.5) | S₅ | 1 | 0.6 | 36 | 61 |
|  |  |  |  | 16 | 34 | 61 |
| 7 | 760 N₂ | S₅ | 1 | 0.6 | 24 | 61 |
|  |  |  |  | 16 | 24 | 59 |
| catalyst: W(NAr')(C₃H₆)(Pyr)(HIPTO) | | | | | | |
| 8 | high vac (~0.5) | S₅ | 1 | 5 | 7 | >98 |
|  |  |  |  | 21 | 22 | >98 |
| 9 | 760 N₂ | S₅ | 1 | 5 | 10 | >98 |
|  |  |  |  | 21 | 27 | >98 |
| catalyst: Mo(NAr)(CHCMe₂Ph)(Pyr)(HIPTO)$^c$ | | | | | | |
| 10 | 10 | S₅ | 1 | 19 | 62 | 88 |
| 11 | 760 N₂ | S₅ | 1 | 0.33 | 31 | 90 |
|  |  |  |  | 19 | 42 | 90 |
| 12 | high vac (~0.5) | S₇ | 1 | 2 | 64 | 94 |
| 13 | 760 N₂ | S₇ | 1 | 2 | 52 | 96 |
| catalyst: Mo(NAd)(CHCMe₃)(Pyr)(HIPTO) | | | | | | |
| 14 | high vac (~1) | S₅ | 1 | 2 | 13 | >98 |
| 15 | 760 N₂ | S₅ | 1 | 2 | 11 | >98 |

$^a$Typical reaction scale is 200 mg.
$^b$10% loss of substrate to vacuum.
$^c$Catalyst was generated in-situ.

5-decene ([CH₃(CH₂)₃(CH)]₂). After the reaction was cooled to room temperature, the mixture was filtered through a 100 mL silica gel plug with hexanes to remove the metal complex. The filtrate was dried via rotavap to remove the solvent and also the substrate, 1-hexene, affording the product as colorless liquid. The scale of a typical reaction was 5 mL of the substrate, 1-hexene. (Z)-5-decene: $^1$H NMR (500 MHz, CDCl₃) δ 5.38 (m, 2, CH), 2.06 (m, 4, CH₂), 1.35 (m, 8, CH₂), 0.93 (m, 6, CH₃); $^{13}$C NMR (125 MHz, CDCl₃) δ 130.06, 32.31, 27.21, 22.66, 14.33.

7-tetradecene ([CH₃(CH₂)₅(CH)]₂). Isolation of this product was the same as (Z)-5-decene, affording the product as colorless liquid. The scale of a typical reaction was 3 mL of the substrate, 1-ocetene. (Z)-tetradec-7-ene: $^1$H NMR (500 MHz, CDCl₃) δ 5.38 (m, 2, CH), 2.06 (m, 4, CH₂), 1.34 (m, 16, CH₂), 0.92 (m, 6, CH₃); $^{13}$C NMR (125 MHz, CDCl₃) δ 130.16, 32.10, 27.50, 22.96, 14.33.

1,4-diphenylbut-2-ene ([Ph(CH₂)CH]₂). After the reaction was cooled to room temperature, the product was purified by silica column chromatography using hexanes as the eluant. The fraction containing the product was dried via rotavap to remove the solvent, affording the product as colorless liquid. The scale of a typical reaction was 2 mL of the substrate, allyl benzene. (Z)-1,4-diphenylbut-2-ene: $^1$H NMR (500 MHz, CDCl₃) δ 7.30 (m, 10, Ar—H), 5.76 (m, 2, CH), 3.57 (d, 4, CH₂, J$_{HH}$=6 Hz); $^{13}$C NMR (125 MHz, CDCl₃) δ 141.03, 129.31, 138.73, 128.63, 126.22, 33.74.

1,4-bis(trimethylsilyl)but-2-ene (CHCH₂SiMe₃)₂. The reaction mixture was filtered though a plug of silica using hexanes as the eluant. The filtrate was dried via rotavap to remove the solvent and the starting material. The desired product was collected as a colorless liquid. The typical scale of the reaction was 2 mL of the starting material, allyltimethylsilane. (Z)-1,4-bis(trimethylsilyl)but-2-ene: $^1$H NMR (500 MHz, CDCl₃) δ 5.31 (m, 2, CH), 1.41 (d, 4, CH₂, J$_{HH}$=7 Hz), 0.00 (s, 18, SiMe₃); $^{13}$C NMR (125 MHz, CDCl₃) δ 123.34, 18.02, −1.48.

Dimethyl icos-10-enedioate. The reaction mixture was purified through a silica gel plug using 1:9 Et₂O:hexanes. The desired product was obtained as colorless oil, which solidified upon standing. (Z)-Dimethyl icos-10-enedioate: $^1$H NMR (500 MHz, CDCl₃) δ 5.34 (m, 2, CH), 3.66 (s, 6, CH₃), 2.30 (t, 4, MeO₂CCH₂, J$_{HH}$=7.5 Hz), 2.00 (m, 2, CH₂CH=CH), 1.61 (m, 2, CH₂CH=CH), 1.28 (m, 24, CH₂); $^{13}$C NMR (125 MHz, CDCl₃) δ 174.57, 130.09, 51.69, 34.35, 29.97, 29.58, 29.47, 29.38, 27.43, 25.19. Anal. Calcd for C₂₂H₄₀O₄: C, 71.70; H, 10.94. Found: C, 71.85; H 10.87.

Dimethyl octadec-9-enedioate. The desired product was isolated using the same method as dimethyl icos-10-enedioate. (Z)-Dimethyl octadec-9-enedioate: $^1$H NMR (500 MHz, CDCl₃) δ 5.34 (m, 2, CH), 3.66 (s, 6, CH₃), 2.30 (t, 4, MeO₂CCH₂, J$_{HH}$=7.5 Hz), 2.00 (m, 4, CH₂CH=CH), 1.61 (m, 4, CH₂), 1.30 (m, 16, CH₂); $^{13}$C NMR (125 MHz, CDCl₃)

δ 174.50, 130.02, 51.63, 34.28, 29.85, 29.34, 29.30, 29.27, 27.34, 25.12. Selected peaks for (E)-Dimethyl octadec-9-enedioate: $^1$H NMR (500 MHz, CDCl$_3$) δ 5.37 (m, 2, CH); $^{13}$C NMR (125 MHz, CDCl$_3$) δ 130.49, 32.73, 29.72, 29.12.

1,4-bis(benzyloxy)but-2-ene. The reaction mixture was purified through a silica gel plug using hexanes to 1:1 Et$_2$O: hexanes. The desired product was obtained as slightly yellow oil. (Z)-1,4-bis(benzyloxy)but-2-ene: $^1$H NMR (500 MHz, CDCl$_3$) δ 7.38-7.32 (m, 10, Ar—H), 5.82 (m, 2H, CH), 4.52 (s, 4, PhCH$_2$), 4.09 (d, 4, OCH$_2$CH, $J_{HH}$=5.0 Hz; $^{13}$C NMR (125 MHz, CDCl$_3$) δ 138.29, 129.70, 128.59, 127.98, 127.96, 72.43, 65.93.

N,N'-(but-2-ene-1,4-diyl)bis(4-methylbenzenesulfonamide) ([tosyl(NH)(CH$_2$CH)]$_2$). After the reaction was cooled to room temperature, the product was purified by silica column chromatography using 1:1 ethyl ether/hexanes and increasing to pure ethyl ether as the eluant.

(Note: load the crude mixture with a small amount of ethyl acetate to dissolve the desired product.) The fraction containing the product was dried via rotavap to remove the solvent. The product was collected as colorless liquid, which solidified to give a white solid upon standing at room temperature overnight. The scale of a typical reaction is 0.5 g of the substrate, allyl tosylamide. (Z)-N,N'-(but-2-ene-1,4-diyl)bis(4-methylbenzenesulfonamide): $^1$H NMR (500 MHz, CDCl$_3$) δ 7.72 (d, 4, Ar—H, $J_{HH}$=8 Hz), 7.30 (d, 4, Ar—H, $J_{HH}$=8 Hz), 5.43 (m, 2, CH), 5.07 (br s, 2, NH), 3.50 (t, 4, CH$_2$, $J_{HH}$=6 Hz), 2.44 (s, 6, CH$_3$); $^{13}$C NMR (125 MHz, CDCl$_3$) δ 143.84, 136.95, 129.99, 128.50, 127.34, 127.31, 39.72, 21.76.

$N^1,N^4$-diphenylbut-2-ene-1,4-diamine ([CHCH$_2$(NHPh)]$_2$). The reaction mixture was purified through a silica gel column using hexanes and increasing to 5:95 Et$_2$O:hexanes. The desired product was obtained as slightly yellow oil, which solidified upon standing. (Z)—$N^1,N^4$-diphenylbut-2-ene-1,4-diamine: $^1$H NMR (500 MHz, CDCl$_3$) δ 7.20 (t, 4, Ar—H, $J_{HH}$=8.0 Hz), 6.76 (t, 2, Ar—H, $J_{HH}$=7.5 Hz), 6.65 (d, 4, Ar—H, $J_{HH}$=7.5 Hz), 5.76 (m, 2, CH═CH), 3.88 (d, 4, CH$_2$, $J_{HH}$=5.0 Hz), 3.72 (br s, 2, NH); $^{13}$C NMR (125 MHz, CDCl$_3$) δ 148.08, 130.01, 129.47, 117.99, 113.22, 41.52. Anal. Calcd for C$_{16}$H$_{18}$N$_2$: C, 80.63; H, 7.61; N, 11.75. Found: C, 80.74; H, 7.63; N, 11.59.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method, comprising:
reacting a first molecule comprising a terminal double bond and a second, identical molecule via a homo-metathesis reaction to produce a product comprising an internal double bond,
wherein the internal double bond of the product comprises one carbon atom from the terminal double bond of the first molecule and one carbon atom from the terminal double bond of the second carbon atom, and
wherein at least about 60% of the internal double bond of the product is formed as the Z-isomer.

2. A method, comprising:
providing a catalyst having the structure:

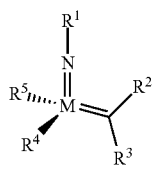

wherein M is Mo or W;
$R^1$ is aryl, heteroaryl, alkyl, heteroalkyl, optionally substituted;
$R^2$ and $R^3$ can be the same or different and are hydrogen, alkyl, alkenyl, heteroalkyl, heteroalkenyl, aryl, or heteroaryl, optionally substituted; and
$R^4$ and $R^5$ can be the same or different and are alkyl, heteroalkyl, aryl, heteroaryl, silylalkyl, or silyloxy, optionally substituted, wherein at least one of $R^4$ or $R^5$ is a ligand containing oxygen bound to M; and
reacting a first molecule comprising a terminal double bond and a second, identical molecule in the presence of the catalyst to produce a product comprising an internal double bond,
wherein the internal double bond of the product comprises one carbon atom from the terminal double bond of the first molecule and one carbon atom from the terminal double bond of the second carbon atom, and
wherein at least about 30% of the internal double bond of the product is formed as the Z-isomer.

3. The method of claim 1, wherein the reacting step is carried out in the presence of a transition metal catalyst.

4. The method of claim 2, wherein at least about 50% of the internal double bond of the product is formed as the Z-isomer.

5. The method of claim 1, wherein at least about 70% of the internal double bond of the product is formed as the Z-isomer.

6. The method of claim 1, wherein at least about 80% of the internal double bond of the product is formed as the Z-isomer.

7. The method of claim 1, wherein at least about 90% of the internal double bond of the product is formed as the Z-isomer.

8. The method of claim 1, wherein at least about 95% of the internal double bond of the product is formed as the Z-isomer.

9. The method of claim 1, wherein at least about 98% of the internal double bond of the product is formed as the Z-isomer.

10. The method of claim 1, wherein the reaction proceeds with a conversion of at least about 30%.

11. The method of claim 1, wherein the reaction proceeds with a conversion of at least about 50%.

12. The method of claim 1, wherein the reaction proceeds with a conversion of at least about 60%.

13. The method of claim 1, wherein the reaction proceeds with a conversion of at least about 70%.

14. The method of claim 1, wherein the reaction proceeds with a conversion of at least about 80%.

15. The method of claim 1, wherein the reaction proceeds with a conversion of at least about 90%.

16. The method of claim 1, wherein the first and second molecules have the formula:

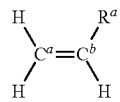

wherein $R^a$ is H, alkyl, alkenyl, heteroalkyl, heteroalkenyl, aryl, heteroaryl, or acyl, optionally substituted.

17. The method of claim 2, wherein one of $R^4$ and $R^5$ is a ligand containing oxygen bound to M, optionally substituted, and the other is a ligand containing nitrogen bound to M, optionally substituted.

18. The method of claim 17, wherein the at least one ligand containing oxygen bound to M lacks a plane of symmetry.

19. The method of claim 17, wherein the ligand containing nitrogen bound to M is selected from the group consisting of pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, and oxazinyl, all optionally substituted.

20. The method of claim 17, wherein the ligand containing nitrogen bound to M is pyrrolyl, optionally substituted.

21. The method of claim 17, wherein the ligand containing oxygen bound to M comprises a group having the formula —OSi($R^{22}$)$_3$, wherein each $R^{22}$ can be the same or different and is aryl or alkyl, optionally substituted.

22. The method of claim 17, wherein $R^1$ and $R^2$ are the same or different and are aryl or alkyl, optionally substituted, and $R^3$ is hydrogen.

23. The method of claim 17, wherein the ligand containing nitrogen bound to M has the structure:

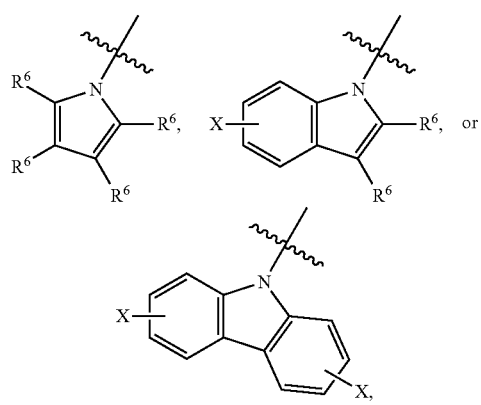

wherein each $R^6$ can be the same or different and is hydrogen, alkyl, heteroalkyl, aryl, or heteroaryl, optionally substituted; and
X may be present or absent and is any non-interfering group.

24. The method of claim 17, wherein the ligand containing oxygen bound to M has the following structure:

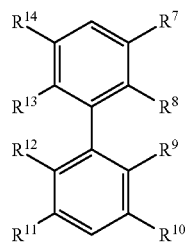

wherein $R^7$ is aryl, heteroaryl, alkyl, or heteroalkyl, optionally substituted;

$R^8$ is

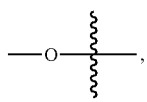

hydrogen, —OH, halogen, alkyl, heteroalkyl, aryl, heteroaryl, acyl, acyloxy, or —OP, optionally substituted; or, together $R^7$ and $R^8$ are joined to form a ring, optionally substituted;

$R^9$ is

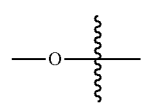

when $R^8$ is not

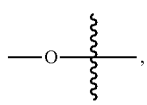

or —OH, —OP, or amino, optionally substituted;

$R^{10}$ is hydrogen, halogen, alkyl, heteroalkyl, aryl, heteroaryl, or acyl, optionally substituted;

each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or together $R^{13}$ and $R^{14}$ are joined to form a ring, optionally substituted; and P is a protecting group.

25. The method as in claim 17, wherein $R^4$ is a derivative of the following structure:

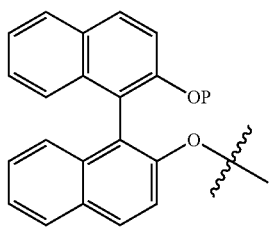

wherein P is a silyl protecting group.

26. The method as in claim 2, wherein $R^1$ is:

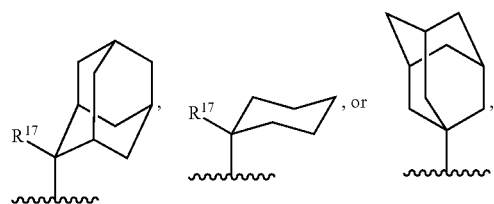

wherein each $R^{17}$ can be the same or different and is hydrogen, halogen, alkyl, heteroalkyl, aryl, acyl, or —OP, optionally substituted; and P is a protecting group.

27. The method as in claim 2, wherein $R^1$ is:

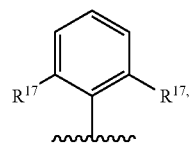

wherein each $R^{17}$ can be the same or different and is hydrogen, halogen, alkyl, heteroalkyl, aryl, acyl, or —OP, optionally substituted; and P is a protecting group.

28. The method as in claim 2, wherein $R^2$ is alkyl.

29. The method as in claim 2, wherein $R^1$ is

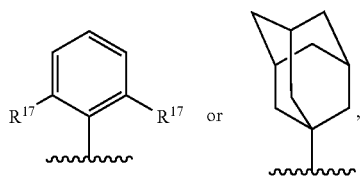

wherein each $R^{17}$ can be the same or different and is hydrogen, halogen, alkyl, heteroalkyl, aryl, acyl, or —OP, optionally substituted;

$R^2$ is $CMe_2Ph$ or $CMe_3$;

$R^3$ is H; and $R^4$ is an enantiomer of the following structure,

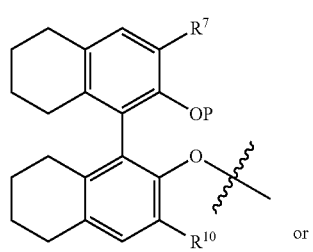

or

-continued

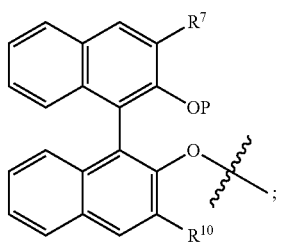

wherein each R⁷ and R¹⁰ is the same or different and is halogen, methyl, t-butyl, CF₃, or aryl, optionally substituted; and P is a protecting group.

30. The method as in claim 29, wherein R⁵ has the following structure:

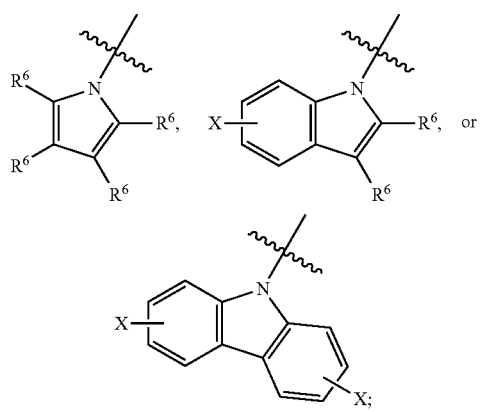

wherein each R⁶ can be the same or different and is hydrogen, alkyl, heteroalkyl, aryl, heteroaryl, optionally substituted; and X may be present or absent and is any non-interfering group.

31. The method of claim 17, wherein the ligand containing oxygen or nitrogen bound to M has the following structure:

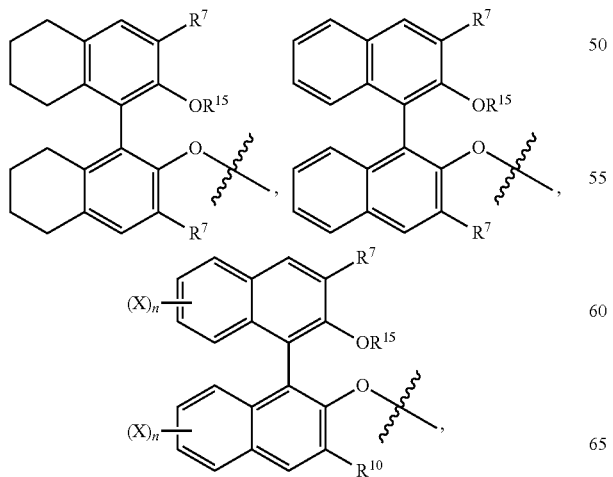

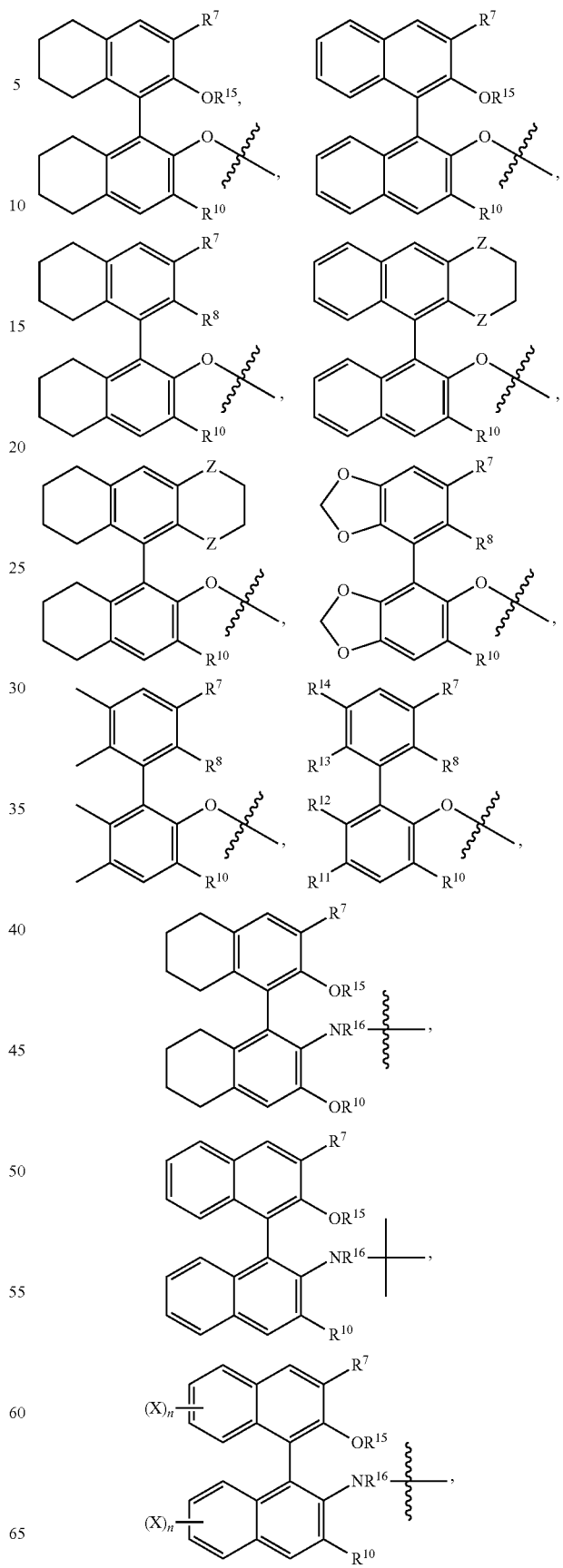

-continued

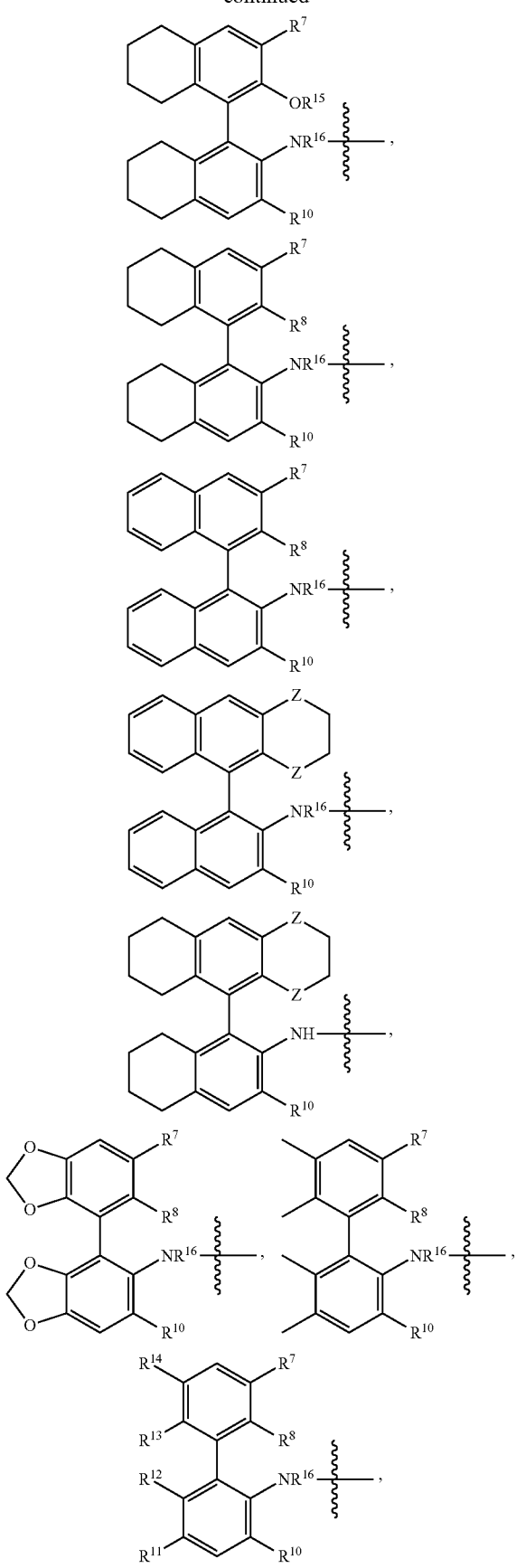

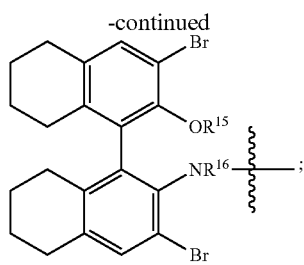

wherein each $R^7$ and $R^8$ can be the same or different and is hydrogen, halogen, alkyl, alkoxy, aryl, acyl, or a protecting group, optionally substituted;

$R^{10}$ is hydrogen, halogen, alkyl, heteroalkyl, aryl, heteroaryl, or acyl, optionally substituted;

each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted;

$R^{15}$ is alkyl, aryl, or a protection group, optionally substituted;

$R^{16}$ is hydrogen or an amine protecting group;

X can be any non-interfering group;

each Z can be the same or different and is $(CH_2)_m$, N, O, optionally substituted;

n is 0-5; and m is 1-4.

32. The method of claim 31, wherein $R^7$ and $R^{10}$ are the same or different and is selected from the group consisting of F, Cl, Br, or I.

33. The method of claim 2, wherein $R^2$ is $CMe_2Ph$ or $CMe_3$ and $R^3$ is hydrogen.

34. The method of claim 2, wherein M is W and $R^1$ is not:

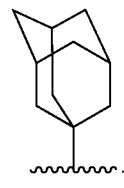

35. The method of claim 2, wherein M is W and $R^1$ is:

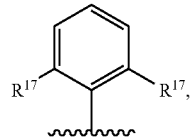

wherein each $R^{17}$ can be the same or different and is hydrogen, halogen, alkyl, heteroalkyl, aryl, acyl, or —OP, optionally substituted, and P is a protecting group.

36. The method of claim 2, wherein the ligand containing oxygen bound to M is hexaisopropylterphenolate.

37. The method of claim 2, wherein the catalyst has a structure selected from the group consisting of M(NAr)(Pyr)(CHR$_2$)(OHIPT), M(NAr)(Pyr)(C$_3$H$_6$)(OHIPT), M(NAr)(CHCMe$_2$Ph)(Pyr)(BiphenTMS), M(NAr)(CHCMe$_2$Ph)

(Me₂Pyr)(Br₂Bitet), M(NAr)(CHCMe₂Ph)(Me₂Pyr)(MesBitet), W(NAr)(CHCMe₂Ph)(Me₂Pyr)(OPhPh₄), M(NAr)(CHCMe₂Ph)(Pyr)((Trip)₂BitetTMS), M(NAr$^{Cl}$)(CHCMe₃)(Pyr)(BiphenTMS), M(NAr$^{Cl}$)(CHCMe₃)(Me₂Pyr)(OSi(TMS)₃), M(NAr$^{Cl}$)(CHCMe₃)(Me₂Pyr)(OPhPh₄), M(NAr$^{Cl}$)(CHCMe₃)(Me₂Pyr)(HIPTO), M(NAr$^{Cl}$)(CHCMe₃)(Me₂Pyr)(HIPTO), M(NAr$^{Cl}$)(CHCMe₃)(Me₂Pyr)(Br₂Bitet), M(NAr$^{Cl}$)(CHCMe₃)(Me₂Pyr)(MesBitet), M(NAr$^{Cl}$)(CHCMe₃)(Pyr)(Mes₂Bitet), M(NAd)(Me₂Pyr)(CHR₂)(Br₂Bitet), M(NAr')(Pyr)(CHR₂)(Mes₂BitetOMe), M(NAd)(CHCMe₂Ph)(Me₂Pyr)(OSi(TMS)₃), M(NAd)(CHCMe₂Ph))(Me₂Pyr)(HIPTO), M(NAd)(CHCMe₂Ph)(Me₂Pyr)(MesBitet), M(NAr')(Pyr)(CHR₂)(OHIPT), M(NAr')(CHCMe₂Ph)(Me₂Pyr)(OSi(TMS)₃), M(NAr')(CHCMe₂Ph)(Me₂Pyr)(OPhPh₄), M(NAr')(CHCMe₂Ph)(Me₂Pyr)(HIPTO), M(NAr')(CHCMe₂Ph)(Me₂Pyr)(Br₂Bitet), M(NAr')(CHCMe₂Ph)(Pyr)(MesBitet), M(NAr')(CHCMe₂Ph)(Me₂Pyr)(MesBitet), M(NAr')(CHCMe₂Ph)(Pyr)(Mes₂BitetOMe), or M(NAr')(CHCMe₂Ph)(Pyr)(Mes₂Bitet), wherein M is Mo or W, Ar is 2,6-diisopropylphenyl, Ar$^{Cl}$ is 2,6-dichlorophenyl, Ar' is 2,6-dimethyphenyl, Ad is 1-admantyl, Mes is mesityl, Me₂Pyr is 2,5-dimethylpyrrolide, Pyr is pyrrolide, TBS is dimethyl-t-butylsilyl, Ts is tosyl, OTf is triflate, Trip is 2,4,6-triisopropylphenyl, HIPTO is hexaisopropylterphenolate, OSi(TMS)₃ is 1,1,1,3,3,3-hexamethyl-2-(trimethylsilyl)trisilan-2-olate, Biphen is 3,3'-di-tert-butyl-5,5',6,6'-tetramethylbiphenyl-2,2'-diol, BiphenTMS is 3,3'-di-tert-butyl-5,5',6,6'-tetramethyl-2'-(trimethylsilyloxy)biphenyl-2-olate, Bitet is 5,5',6,6',7,7',8,8'-octahydro-1,1'-binaphthyl-2,2'-diol, Trip₂Bitet is 3,3'-bis(2,4,6-triisopropylphenyl)-5,5',6,6',7,7',8,8'-octahydro-1,1'-binaphthyl-2,2'-diol, Trip₂BitetTMS is 3,3'-bis(2,4,6-triisopropylphenyl)-2'-(trimethylsilyloxy)-5,5',6,6',7,7',8,8'-octahydro-1,1'-binaphthyl-2-olate, Br₂Bitet is 3,3'-dibromo-2'-(tert-butyldimethylsilyloxy)-5,5',6,6',7,7',8,8'-octahydro-1,1'-binaphthyl-2-olate, MesBitet is 2'-(tert-butyldimethylsilyloxy)-3-mesityl-5,5',6,6',7,7',8,8'-octahydro-1,1'-binaphthyl-2-olate, Mes₂Bitet is 3,3'-dimesityl-2'-(tert-butyldimethylsilyloxy)-5,5',6,6',7,7',8,8'-octahydro-1,1'-binaphthyl-2-olate, and Mes₂BitetOMe is 3,3'-dimesityl-2'-methoxy-5,5',6,6',7,7',8,8'-octahydro-1,1'-binaphthyl-2-olate.

\* \* \* \* \*